United States Patent
Gharibans et al.

(10) Patent No.: US 12,336,824 B2
(45) Date of Patent: Jun. 24, 2025

(54) GASTROINTESTINAL DIAGNOSTIC AID

(71) Applicant: Alimetry Limited, Auckland (NZ)

(72) Inventors: Armen A. Gharibans, Auckland (NZ); Gabriel Schamberg, Auckland (NZ); Gregory B. O'Grady, Auckland (NZ); Stefan Sam Scott Calder, Auckland (NZ); Chris Varghese, Auckland (NZ); Gayl Humphrey, Auckland (NZ)

(73) Assignee: Alimetry Limited, Auckland (NZ)

( * ) Notice: Subject to any disclaimer, the term of this patent is extended or adjusted under 35 U.S.C. 154(b) by 0 days.

(21) Appl. No.: 18/893,635

(22) Filed: Sep. 23, 2024

(65) Prior Publication Data
US 2025/0152066 A1    May 15, 2025

Related U.S. Application Data

(63) Continuation-in-part of application No. 18/389,450, filed on Nov. 14, 2023.
(Continued)

(51) Int. Cl.
*A61B 5/273* (2021.01)
*A61B 5/00* (2006.01)
(Continued)

(52) U.S. Cl.
CPC ............ *A61B 5/279* (2021.01); *A61B 5/42* (2013.01); *G16H 40/67* (2018.01)

(58) Field of Classification Search
CPC ........... A61B 5/279; A61B 5/42; A61B 5/273; A61B 5/392; A61B 5/24; A61B 5/25;
(Continued)

(56) References Cited

U.S. PATENT DOCUMENTS 8,417,342 B1 * 4/2013 Abell ................. A61N 1/0509
607/40
9,474,482 B2   10/2016 Devanaboyina
(Continued)

FOREIGN PATENT DOCUMENTS

WO    2017070700 A1    4/2017
WO    2017201538 A1    11/2017

OTHER PUBLICATIONS

Gharibans et al., "A Novel Scalable Electrode Array and System for Non-Invasively Assessing Gastric Function Using Flexible Electronics", Neurogastroenterology & Motility, vol. 35, No. 2, Jun. 14, 2022, pp. 1-11.
(Continued)

*Primary Examiner* — Adam Z Minchella
(74) *Attorney, Agent, or Firm* — Kilpatrick Townsend & Stockton LLP

(57) ABSTRACT

The present invention discloses systems and methods for mapping gastric activity with an electrode array patch disposed over an abdomen skin surface of a patient. A method may include measuring electrical signals associated with gastric activity of the patient with the electrode array patch over a predetermined time period and concurrently receiving patient symptom information, determining one or more normalized biometrics from the measured electrical signals, correlating the one or more normalized biometrics and the patient symptom information, determining a measure of correlation, determining a measure of temporal association, and determining a gastrointestinal phenotype of the patient based at least in part on the measure of correlation and the measure of temporal association. The present invention advantageously enables mapping of gut motility patterns at high spatial resolution for the identification of gastric disorders and provides biomarkers of pathophysiology which include correlations with symptom severity profiles.

25 Claims, 35 Drawing Sheets
(24 of 35 Drawing Sheet(s) Filed in Color)

Related U.S. Application Data

(60) Provisional application No. 63/642,417, filed on May 3, 2024.

(51) Int. Cl.
*A61B 5/279* (2021.01)
*A61B 5/392* (2021.01)
*G16H 40/67* (2018.01)

(58) Field of Classification Search
CPC ............... A61B 5/4255; A61B 5/6833; A61B 2562/225; G16H 40/67
See application file for complete search history.

(56) References Cited

U.S. PATENT DOCUMENTS

| | | | |
|---|---|---|---|
| 10,285,617 | B2 | 5/2019 | Toth et al. |
| 10,485,444 | B2 | 11/2019 | Axelrod |
| 10,512,414 | B2 | 12/2019 | Axelrod et al. |
| 10,898,099 | B2 | 1/2021 | Coleman et al. |
| 11,006,838 | B2 | 5/2021 | Coleman et al. |
| 11,284,831 | B2 | 3/2022 | Toth et al. |
| 11,432,759 | B2 | 9/2022 | Devanaboyina |
| 11,826,157 | B2 | 11/2023 | Axelrod |
| 11,826,170 | B2 | 11/2023 | Navalgund et al. |
| 2013/0035576 | A1 | 2/2013 | O'Grady et al. |
| 2018/0317800 | A1* | 11/2018 | Coleman ............... A61B 5/296 |
| 2019/0008442 | A1 | 1/2019 | O'Grady et al. |
| 2019/0350484 | A1* | 11/2019 | Coleman ............... A61B 5/296 |
| 2022/0192580 | A1 | 6/2022 | Toth et al. |
| 2022/0249022 | A1 | 8/2022 | Toth et al. |
| 2023/0083795 | A1 | 3/2023 | O'Grady et al. |
| 2024/0057928 | A1 | 2/2024 | Axelrod |

OTHER PUBLICATIONS

Humphrey et al., "Designing, Developing, and Validating a Set of Standardized Pictograms to Support Pediatric-Reported Gastroduodenal Symptoms", The Journal of Pediatrics, vol. 267, No. 113922, Jan. 17, 2024, pp. 1-9.

O'Grady et al., "Principles and Clinical Methods of Body Surface Gastric Mapping: Technical Review", Neurogastroenterology & Motility, vol. 35, No. 10, Mar. 29, 2023, pp. 1-17.

Schamberg et al., "Physiology-Guided Quantitative Symptom Analysis for Gastroduodenal Disorders", Available Online at: https://www.medrxiv.org/content/10.1101/2023.06.07.23291112v1.full.pdf, Jun. 12, 2023, 11 pages.

Schamberg et al., "Revised Spectral Metrics for Body Surface Measurements of Gastric Electrophysiology", Neurogastroenterology & Motility, vol. 35, No. 3, Nov. 21, 2022, pp. 1-11.

Sebaratnam et al., "It's a Helluva Journey: A Qualitative Study of Patient and Clinician Experiences of Nausea and Vomiting Syndromes", Frontiers in Psychology, vol. 14, No. 1232871, Aug. 11, 2023, pp. 1-9.

Sebaratnam et al., "Standardized System and App for Continuous Patient Symptom Logging in Gastroduodenal Disorders: Design, Implementation, and Validation", Neurogastroenterology & Motility, vol. 34, No. 8, Feb. 13, 2022, pp. 1-10.

Varghese et al., "Normative Values for Body Surface Gastric Mapping Evaluations of Gastric Motility Using Gastric Alimetry: Spectral Analysis", The American Journal of Gastroenterology, vol. 118, No. 6, Jul. 26, 2022, 37 pages.

Varghese et al., "Standardized Mechanism-Based Digital Profiling of Gastroduodenal Symptoms", Available Online at: https://papers.ssrn.com/sol3/papers.cfm?abstract_id=4517181, Jul. 25, 2023, 51 pages.

Xu et al., "Characterisation of Post-Fundoplication Gastric Dysfunction Using Gastric Alimetry", Available Online at: https://www.medrxiv.org/content/10.1101/2023.11.05.23297357v1.full.pdf, Nov. 6, 2023, 44 pages.

Xu et al., "Defining and Phenotyping Gastric Abnormalities in Long-Term Type 1 Diabetes Using a Novel Body Surface Gastric Mapping Device", Gastro Hep Advances, vol. 2, No. 8, Aug. 17, 2023, pp. 1120-1132.

Xu et al., "Defining and phenotyping gastric abnormalities in long-term type 1 diabetes using body surface gastric mapping", Available online at: medRxiv preprint doi: https://doi.org/10.1101/2022.08.10.22278649, Aug. 11, 2022, 29 pages.

* cited by examiner

Gastric Emptying Test

Gastric Alimetry Spectral

GASTRIC ALIMETRY SYMPTOM AXIS

GASTROINTESTINAL DIAGNOSTIC AID

CROSS-REFERENCES TO RELATED APPLICATIONS

The present application claims the benefit of U.S. Provisional Application Ser. No. 63/642,417 filed May 3, 2024, and is a Continuation-in-Part of U.S. patent application Ser. No. 18/389,450 filed Nov. 14, 2023; the disclosures which are incorporated herein by reference in their entirety for all purposes.

BACKGROUND

Chronic gastro-duodenal symptoms affect more than 10% of the global population and have a significant healthcare burden, resulting in a significant economic impact. Functional gastrointestinal (GI) disorders are among the most prominent causes of chronic ill-health in both adults and children. Chronic gastroduodenal diagnosis paradigms rely on symptom-based criteria which group nausea, vomiting, abdominal pain, early satiety, and/or excessive fullness into disorders such as chronic nausea and vomiting syndromes (CNVS), functional dyspepsia (FD), and when gastric emptying is delayed, gastroparesis. However, these classifications substantially overlap, limiting their clinical utility and ability to effectively inform individual patient management.

Functional gastrointestinal disorders (FGIDs, or disorders of gut-brain interaction) place an economic burden on healthcare systems and reduce patient quality of life. Functional gastrointestinal disorders generally affect 35% to 70% of people at some point in life, women more often than men. For example, more than 70% of patients indicate that their symptoms interfere with everyday life and 46% report missing work or school. A recent review of 26 studies found that between 10-29% of school children reported symptoms consistent with a functional GI disorder. The symptoms are frequently distressing and may be severe and debilitating, encompassing chronic abdominal pain, abdominal distension, anorexia, and chronic nausea and vomiting. These disorders collectively extract a major illness burden, including a significantly reduced quality of life, and are common reasons for adults and children missing work or school.

Current GI diagnosis include gastroparesis and functional dyspepsia disorders. Gastroparesis is defined by symptoms of nausea and vomiting, typically with other symptoms e.g., abdominal pain, bloating, burning, excessive fullness, early satiation, and/or documented presence of delayed gastric emptying. Functional dyspepsia is defined by chronic symptoms such as distress after eating, indigestion, abdominal pain, bloating, burning, excessive fullness, and/or early satiation. Gastric emptying may also be delayed in up to 25% of patients identified with functional dyspepsia, and therefore overlaps with gastroparesis, however nausea and vomiting are not considered the dominant feature. Because these disorders overlap significantly, or at least many patients are on the same disease spectrum, there is a state of confusion in the clinical field. For example, clinicians are often unsure how to define, distinguish and diagnose such patients, and therefore are unable to provide appropriate patient specific management plans, typically reverting to trial and error type therapies.

Objectively evaluating and treating adults and children with chronic upper GI symptoms is a major clinical challenge, owing to a lack of routine tests that may reliably and safely distinguish specific underlying disorders. Relying on symptom-based diagnoses often results in less than ideal and potentially hazardous attempts at trial and error treatments. Currently, both adult and pediatric patients with chronic GI symptoms frequently undergo a protracted diagnostic process that may include endoscopies, biopsies, lab tests, nuclear medicine studies, manometry and radiology exams, often over numerous years. Many of these tests are invasive and involve radiation, yet the diagnostic results are often inconclusive. For example, gastric scintigraphy and antroduodenal manometry are two tests that are commonly performed in adult and pediatric gastroenterology, as they may distinguish myopathic or neuropathic functional disorders, and may impact diagnosis and treatment in 15-20% of patients with chronic upper GI symptoms. However, the interpretation of these tests may be uncertain, especially in pediatric applications due to a lack of diagnostic norms in children. Furthermore, these tests typically involve long wait times and high cost as these tests are generally only available in specialist referral centers.

There is a pressing need for improved and less invasive diagnostic tests that have clinical utility, offer actionable and objective biomarkers that improve both adult and pediatric diagnostic and treatment efficacy, reduce patient harm from negative invasive or unnecessary testing, and directly impact clinical care decisions and treatment. The advent of a less invasive and technically safer diagnostic test for adults and children would broaden availability and access and reduce the high healthcare expenses of motility testing. An optimal diagnostic solution would be non-invasive, user-friendly, easy to apply and interpret, and provide meaningful results that correlate with symptoms and inform clinical care.

SUMMARY

The present invention is directed to user-friendly methods and systems for mapping gastric activity for objective symptom profiling and gastrointestinal phenotyping, thereby providing efficacious and reliable diagnosis and appropriate therapeutic options for both adult and pediatric patients. Various embodiments of the present invention include non-invasive gastric activity detection systems, such as an electrode array patch and data acquisition/connector device for mapping gastric activity. Embodiments described herein may be used in the diagnosis and therapy of adults and children presenting with functional upper GI symptoms by monitoring, analyzing and optimizing measured electrical signals from the non-invasive electrode array patch to provide meaningful results that correlate with symptoms and inform clinical/patient care.

Embodiments include utilizing real-time patient reported symptoms as a component of the gastrointestinal system for clinical assessment and diagnosis of gastro-duodenal disorders. Embodiments of the present invention have been shown to provide superior results over the Rome diagnostic questionnaire. At least some embodiments of the present invention advantageously avoid the classification of the presence or absence of symptoms over a long timeframe (typically months) and/or avoid significant overlap between symptoms and/or diagnoses (e.g., gastroparesis, functional dyspepsia, and/or chronic nausea and vomiting) and/or provide insight into patient specific symptom etiology and appropriate patient specific treatment plans.

Various embodiments are directed to identifying abnormal gastric motility in a significant subgroup of patients with chronic gastric conditions. In some embodiments, the teachings herein are directed to identifying gastric motility that affects only a subset of people falling within a group in the overall population that are less than, greater than, or equal to 1, 2, 3, 4, 5, 6, 7, 8, 9, 10, 11, 12, 13, 14, 15, 16, 17, 18, 19 or 20% or any value or range of values therebetween in 1% increments. Embodiments of the present invention provide a reliable and objective method for assessing gastric motor function in clinical practice. Embodiments have been shown to provide correct assessment at least a 75, 80, 85, 90, 91, 92, 93, 94, 95, 96, 97, 98 or 99% or greater rate or any value or range of values therebetween in 1% increments out of at least 50, 100, 200, 300, 400 or 500 or more random patients.

At least some of the embodiments described herein provide a standardized system for quantitative assessment of an individual patient. The system may include continuous or semi-continuous assessment of symptom severity particularly after a meal stimulus for the purposes of diagnostic data collection. Systems described herein use Body Surface Gastric Mapping (BSGM) employing multi-electrode array patches, as described in further detail in U.S. Patent Application No. US 2023-0083795 A1, which is incorporated herein by reference in its entirety for all purposes, to measure and map gastric myoelectrical activity. BSGM may be used in some embodiments of the presentation invention to provide high-quality and high-resolution information non-invasively. Embodiments may also include semi-automated digital and/or analogue tools developed for receiving standardized gastric symptom profiling. These tools may also be used simultaneously during testing to further aid in the identification/refinement of specific disease phenotypes.

According to one embodiment, a method for mapping gastric activity with an electrode array patch disposed over an abdomen skin surface of a patient include measuring electrical signals associated with gastric activity of the patient with the electrode array patch over a predetermined time period, concurrently receiving patient symptom information over the predetermined time period, determining one or more normalized biometrics over at least a portion of the predetermined time period from the measured electrical signals, correlating the one or more normalized biometrics and the patient symptom information, determining a measure of correlation over the predetermined time period, determining a measure of temporal association in at least one time interval over the predetermined time period between the one or more normalized biometrics and patient symptom information, and determining a gastrointestinal phenotype of the patient based at least in part on the measure of correlation and the measure of temporal association.

The method may include various optional embodiments. The gastrointestinal phenotype may include at least one of a normal Body Surface Gastric Mapping (BSGM) phenotype, a delayed onset phenotype, a low stability and/or low amplitude phenotype, or a high amplitude phenotype. The normal BSGM phenotype may be associated with no measure of correlation and a measure of temporal association between −0.25 and +0.25 over a predetermined pre-prandial and post-prandial time period. The delayed onset phenotype may be associated with a measure of temporal association less than −0.25 over a predetermined pre-prandial and post-prandial time period. The low stability and/or low amplitude phenotype may be associated with no measure of correlation and a measure of temporal association between −0.25 and +0.25 over a predetermined pre-prandial and post-prandial time period. The low stability and/or low amplitude phenotype may be associated with neuromuscular disorders. The neuromuscular disorder may include at least one of gastric dysrhythmias, interstitial cell of Cajal disorders, antral hypomotility, smooth muscle disorders, or gastroparesis. The normal BSGM phenotype may be associated with a gut-brain axis disorder. The gut-brain axis disorder may include at least one of irritable bowel syndrome, reflux hypersensitivity, or functional dyspepsia. The delayed onset phenotype may be associated with gastroparesis. The one or more normalized biometrics may include at least one of a principal gastric frequency (PGF), a body mass index (BMI)-adjusted amplitude, Gastric Alimetry Rhythm Index (GA-RI), fed-fasted amplitude ratio (ff-AR), and meal response ratio. The method may include providing the patient a predetermined standardized meal prior to or during the predetermined time period. Measuring electrical signals with the electrode array patch over the predetermined time period may include generating spatial information associated with gastric activity of the patient. The method may include outputting a recommendation based at least in part on the phenotype associated with the patient. The patient symptom information may be received at predetermined intervals over the predetermined time period. The predetermined interval may include 15 minutes. The predetermined time period may be between 2 hours and 6 hours. The predetermined time period may be 4 hours. The patient symptom information may be input as symptoms occur. The patient symptom information may be received for a set of symptoms comprising nausea, vomiting, bloating, upper gut pain, heartburn, stomach burn, or excessive fullness. Receiving patient symptom information may include receiving a perceived symptom burden for each symptom of the set of symptoms over the predetermined time period. The patient symptom information may be received for a set of psychological symptoms comprising depression, excessive fatigue, cognitive difficulty, or anxiety. Receiving patient symptom information may include receiving a perceived symptom burden for each psychological symptom of the set of psychological symptoms. The gastrointestinal phenotype may include at least one of a sensorimotor phenotype, a neuromuscular phenotype, a post-gastric phenotype, an activity-alleviated phenotype, or a continuous phenotype. The post-gastric phenotype may be associated with a measure of temporal association greater than +0.25 over a predetermined pre-prandial and post-prandial time period.

According to another embodiment, a system for mapping gastric activity of a patient includes an electrode array patch having a plurality of electrodes configured to measure electrical signals associated with gastric activity of the patient over a predetermined time period and a processor to receive the measured electrical signals from the electrode array patch over a predetermined time period, concurrently receive patient symptom information over the predetermined time period, determine one or more normalized biometrics over at least a portion of the predetermined time period from the measured electrical signals, correlating the one or more normalized biometrics and the patient symptom information, determine a measure of correlation over the predetermined time period, determine a measure of temporal association in at least one time interval over the predetermined time period between the one or more normalized biometrics and patient symptom information, and determine a gastrointestinal phenotype of the patient based at least in part on the measure of correlation and the measure of temporal association. The processor further generates a report comprising at least the determination of the gastrointestinal phenotype.

The system may include various optional embodiments. The system may include a connector device coupled to the electrode array patch and wirelessly coupled to the processor. The connector device is for transmission of the measured electrical signals to the processor. The system may further include a patient mobile device for patient symptom information input where the patient mobile device is in wireless communication with the processor for transmission of patient symptom information. The system may include a display for displaying the generated report. The gastrointestinal phenotype may include at least one of a normal Body Surface Gastric Mapping (BSGM) phenotype, a delayed onset phenotype, a low stability and/or low amplitude phenotype, or a high amplitude phenotype. The normal BSGM phenotype may be associated with no measure of correlation and a measure of temporal association between −0.25 and +0.25 over a predetermined pre-prandial and post-prandial time period. The delayed onset phenotype may be associated with a measure of temporal association less than −0.25 over a predetermined pre-prandial and post-prandial time period. The low stability and/or low amplitude phenotype may be associated with between −0.25 and +0.25 over a predetermined pre-prandial and post-prandial time period. The low stability and/or low amplitude phenotype may be associated with neuromuscular disorders. The neuromuscular disorder may include at least one of gastric dysrhythmias, interstitial cell of Cajal disorders, antral hypomotility, smooth muscle disorders, or gastroparesis. The normal BSGM phenotype may be associated with a gut-brain axis disorder. The gut-brain axis disorder may include at least one of irritable bowel syndrome, reflux hypersensitivity, or functional dyspepsia. The delayed onset phenotype may be associated with gastroparesis. The one or more normalized biometrics may include at least one of a principal gastric frequency (PGF), a body mass index (BMI)-adjusted amplitude, Gastric Alimetry Rhythm Index (GA-RI), fed-fasted amplitude ratio (ff-AR), and meal response ratio. The patient may ingest a predetermined standardized meal prior to or during the predetermined time period. The measured electrical signals provide spatial information may be associated with gastric activity of the patient. The processor may further output a recommendation based at least in part on the phenotype associated with the patient. The patient symptom information may be received at predetermined intervals over the predetermined time period. The predetermined interval may be 15 minutes. The predetermined time period may be between 2 hours and 6 hours. The predetermined time period may be 4 hours. The patient symptom information may be input as symptoms occur. The patient symptom information may be received for a set of symptoms including nausea, vomiting, bloating, upper gut pain, heartburn, stomach burn, or excessive fullness. The patient symptom information may include a perceived symptom burden for each symptom of the set of symptoms over the predetermined time period. The patient symptom information may be received for a set of psychological symptoms comprising depression, excessive fatigue, cognitive difficulty, or anxiety. The patient symptom information may include a perceived symptom burden for each psychological symptom of the set of psychological symptoms. The gastrointestinal phenotype may include at least one of a sensorimotor phenotype, a neuromuscular phenotype, a post-gastric phenotype, an activity-alleviated phenotype, or a continuous phenotype.

According to another embodiment, a method for mapping gastric activity with an electrode array patch disposed over an abdomen skin surface of a patient includes measuring electrical signals associated with gastric activity of the patient from the electrode array patch over a predetermined time period, determining one or more normalized biometrics over at least a portion of the predetermined time period from the measured electrical signals, determining one or more features of the one or more normalized biometrics over the predetermined time period, and determining a gastrointestinal phenotype of the patient based at least in part on the one or more features.

The method may include various optional embodiments. The gastrointestinal phenotype may include at least one of a dysrhythmic phenotype, a low amplitude phenotype, a high amplitude phenotype, a low frequency phenotype, a high frequency phenotype, or a lagged meal response phenotype. The one or more features may include an amplitude, a frequency, or a temporal association.

According to one embodiment, a system for mapping gastric activity of a patient includes an electrode array patch having a plurality of electrodes configured to measure electrical signals associated with gastric activity of the patient over a predetermined time period and a processor to receive the measured electrical signals from the electrode array patch over a predetermined time period, determine one or more normalized biometrics over at least a portion of the predetermined time period from the measured electrical signals, determining one or more features of the one or more normalized biometrics over the predetermined time period, and determining a gastrointestinal phenotype of the patient based at least in part on the one or more features. The processor generates a report comprising at least the determination of the gastrointestinal phenotype.

The system may include various optional embodiments. The gastrointestinal phenotype may include at least one of a dysrhythmic phenotype, a low amplitude phenotype, a high amplitude phenotype, a low frequency phenotype, a high frequency phenotype, or a lagged meal response phenotype. The one or more features may include an amplitude, a frequency, or a temporal association.

According to another embodiment, a method for mapping gastric activity of a patient post-gastrointestinal surgery with an electrode array patch disposed over an abdomen skin surface of the patient includes measuring electrical signals associated with gastric activity after the gastrointestinal surgery of the patient with the electrode array patch over a predetermined time period, concurrently receiving patient symptom information over the predetermined time period, determining one or more normalized biometrics over at least a portion of the predetermined time period from the measured electrical signals, correlating the one or more normalized biometrics and the patient symptom information, determining a measure of correlation over the predetermined time period, determining a measure of temporal association in at least one time interval over the predetermined time period between the one or more normalized biometrics and patient symptom information, and determining a gastrointestinal phenotype of the patient post-gastrointestinal surgery based at least in part on the measure of correlation and the measure of temporal association.

The method may include various optional embodiments. The gastrointestinal phenotype may include at least one of a low rhythm stability phenotype or a high frequency phenotype. The high frequency phenotype may be associated with vagal injury. The gastrointestinal surgery may be fundoplication.

According to another embodiment of the present invention, a method includes monitoring a patient's gastric activity by receiving data based on spectral gastric activity with an electrode array patch over a predetermined test period, concurrently receiving patient symptom information for a predetermined set of symptoms during at least a portion of the test period, determining a normalized gastric activity amplitude over at least a portion of the test period from the measured gastric activity data, and correlating over at least a portion of the test period said patient symptom information with said normalized gastric activity amplitude. The method further includes determining a measure of said correlation and treating for a gut-brain axis disorder if the measure indicates a correlation is absent, optionally by not satisfying a predetermined correlation threshold, or treating for gastric dysfunction or hypersensitivity if the measure of said correlation indicates a correlation exists, optionally by satisfying a predetermined correlation threshold.

The method may include various to optional embodiments. The method may include a patient ingesting a predetermined standardized meal preferably at a predetermined time during the test period. The method may include receiving data based on measured spectral gastric activity measured with an electrode array patch during a first temporal test period and receiving data based on patient symptom information for a predetermined set of symptoms. The patient symptom information may be received during at least a portion of the first temporal test period. The method may further include determining data indicative of normalized gastric activity amplitude from the received data based on the measured gastric activity data, correlating said patient symptom information with said data indicative of normalized gastric activity amplitude over the test period, evaluating the correlation, and identifying a treatment for a gut-brain axis disorder if the evaluation of the correlation indicates no clinical correlation exists.

Another embodiment of the present invention includes a method including receiving first data based on measured spectral gastric activity measured with an electrode array patch during a first temporal test period and receiving second data based on patient symptom information for a predetermined set of symptoms. The patient symptom information was received during at least a portion of the first temporal test period. The method further includes providing the first and second data, receiving third data, and prescribing a treatment based on the third data. The third data is an evaluation of a correlation of the first data with data indicative of normalized gastric activity amplitude from the second data.

The method may include various optional embodiments. The patient symptom information may be received based on output from a patient who assigned a symptom severity metric at intervals during the test period. The measure of the correlation may be displayed or output in a digital or physical medium. The symptom information may be received for said set of symptoms based on one or more of, or an average of two or more of nausea, bloating, upper gut pain, heartburn, stomach burn, or excessive fullness. The method may include that the measuring of gastric activity with an electrode array patch further includes spatial information of said gastric activity. The method may include that the treating for a gut-brain axis disorder only occurs when said spectral gastric activity is indicated as normal.

According to yet another embodiment, a method includes monitoring a patient's gastric activity by measuring spectral gastric activity with an electrode patch over a predetermined test period, concurrently receiving patient symptom information over at least a portion of the test period, determining a measure of gastric activity amplitude from the measured gastric activity data, and correlating said patient symptom information with said gastric activity amplitude over the at least a portion of the test period. The method further includes determining a measure of said correlation and classifying a patient into one of a predetermined phenotype set based on the determined measure of said correlation.

The method may include various optional embodiments. The method may further include the patient ingesting a predetermined standardized meal, preferably at a predetermined time during the test period. The phenotype may be one or more of a sensorimotor phenotype, if indicative of synchronization between symptom severity and gastric amplitude, a post-gastric phenotype, if indicative of symptom severity following gastric activity, an activity alleviated phenotype, if indicative of symptoms preceding a delayed onset of gastric activity, or a continuous phenotype, if indicative of symptom severity being high and optionally consistent throughout the test and/or a lack of correlation between gastric amplitude and symptom severity and where symptom severity is high and optionally consistent throughout the test. The method may include measuring of gastric activity with an electrode array patch and may further include measuring spatial information of said gastric activity. The portion of the predetermined test period may be at least approximately 45 minutes.

According to yet another embodiment, a system includes electronics including a data input and a data output and an electrode assembly including a plurality of electrodes. The electrode assembly is placed on an abdomen of a human and maintained thereon for at least a predetermined test period. The electrode assembly is in signal communication with the data input and the system includes a second data input configured to receive data related to severity, based on assessment by the human, of a predetermined set of symptoms. The electronics output information based on signals received from the electrode assembly via the data input and the second data input in a temporally correlated and/or correlatable manner. The system executes any of the methods described herein.

According to another embodiment, a system includes an input suite configured to receive data based on data recorded from electrodes on an abdomen of a human and receive data based on a state of human perceptions of predetermined symptoms, memory configured to store, if only in a transitory manner, the received data, and electronics to automatically evaluate the received data and indicate a whether the human suffers from one or more predetermined gastric aliments based on the evaluation. The system executes any of the methods described herein.

According to yet another embodiment, a method includes monitoring a patient's gastric activity by receiving data based on measured spectral gastric activity over a predetermined test period, receiving patient symptom information based on data received from the patient during at least a portion of the test period, and determining a normalized continuous symptom severity function. The method includes determining normalized gastric activity amplitude over at least a portion of the test period based on data the measured gastric activity data and determining a degree of temporal association between the normalized gastric amplitude and normalized continuous symptom severity functions for a symptom selected from a predetermined set of symptoms and/or for an average symptom function for two or more symptoms selected from the predetermined set of symptoms.

The method may include various optional embodiments. The method may include the patient ingesting a predetermined standardized meal preferably at a predetermined time during the test period. The predetermined set of symptoms may be chosen from one or more of, or an average of two or more of nausea, bloating, upper gut pain, heartburn, stomach burn, or excessive fullness. The method may include classifying the patient for example as a sensorimotor phenotype when synchronization between normalized gastric amplitude and normalized symptom severity functions is identified. The method may include calculating a temporal correlation coefficient and assessing based on the coefficient the temporal synchronization of the normalized gastric activity amplitude and a normalized symptom severity curve. The temporal correlation coefficient may be calculated for each symptom severity curve if a standard deviation is above a predetermined standard deviation threshold. The temporal correlation coefficient may be calculated for the average normalized symptom severity curve if a standard deviation is above a predetermined deviation threshold. The method may include calculating an amplitude correlation coefficient if a standard deviation of the gastric amplitude function is above a predetermined gastric amplitude deviation threshold. The temporal correlation coefficient, for example Pearson's r, may be calculated between the normalized gastric amplitude function and normalized symptom severity function for lags of ranging from approximately −10 to +10 minutes, with approximately 1-minute steps, and the correlation is taken as the maximum of these values. A maximum temporal correlation coefficient may be used to determine a phenotype for temporal associations between normalized gastric amplitude and normalized symptom severity. A sensorimotor phenotype may be indicated when the maximum temporal correlation coefficient is greater than 0.5. The method may include measuring of spectral gastric activity with an electrode array patch further includes spatial information of said gastric activity. The method may further include measuring spatial information of the gastric activity and the identification of the treatment and/or ailment and/or symptom is also based on the measured spatial information. A determined sensorimotor phenotype may be used by a clinician to provide targeted therapies to a patient by treating as postprandial distress syndrome.

According to yet another embodiment, a method includes monitoring a patient's gastric activity by measuring spectral gastric activity with an electrode patch over a predetermined test period, concurrently receiving patient symptom information over at least a portion of the test period for one or more predetermined symptoms, and determining a normalized continuous symptom severity function, determining a normalized gastric activity amplitude function from the measured gastric activity data, and identifying a time lag between the gastric amplitude and one or more symptom severity functions.

The method may include various optional embodiments. The method may include the patient ingesting a predetermined standardized meal preferably at a predetermined time during the test period. An average difference between cumulative distribution functions (CDFs) may be used to assess the time lag between normalized gastric amplitude and a normalized continuous symptom severity function. The correlation coefficient may be calculated for one or more respective symptom severity curves if a standard deviation is above a predetermined deviation threshold. The predetermined deviation threshold may be 0.5. The correlation coefficient may be calculated for the average symptom severity function if a standard deviation is above a predetermined deviation threshold. The predetermined deviation threshold may be 0.1. The gastric amplitude function may be normalized by the minimum value of the gastric amplitude function being subtracted from the whole function, and the gastric amplitude function is divided by its sum. The time lag may be quantified as the average difference between the CDF of the normalized gastric amplitude function and the CDF of the normalized symptom severity function. The time lag may be thresholded to determine phenotypes associated with symptoms that either precede or follow gastric activity according to a post-gastric phenotype of symptoms following gastric activity is indicated if said time lag is greater than 0.25, or an activity-alleviated phenotype if symptoms preceding gastric activity is indicated when said time lag is less than −0.25. The post-gastric phenotype may be associated with a measure of temporal association greater than +0.25 over the predetermined pre-prandial and post-prandial time period. The method may include measuring of spectral gastric activity with an electrode array patch, further includes spatial information of said gastric activity. The determined phenotypes may be used by a clinician to provide targeted therapies to patients. The post-gastric phenotype may be treated as having small bowel/biliary causes. The activity-alleviated phenotype may be treated using a neuromodulator such as mirtazapine or a prokinetic such as erythromycin.

According to one embodiment, a method includes monitoring a patient's gastric activity by measuring spectral gastric activity with an electrode patch over a predetermined test period, concurrently receiving patient symptom information over at least a portion of the test period and determining a normalized continuous symptom severity function. The method includes determining a normalized gastric activity amplitude function from the measured gastric activity data and identifying a lack of temporal correlation. The method includes determining that the gastric amplitude function does not follow or precede the normalized symptom severity function and determining a symptom severity score from said continuous symptom severity function.

The method may include various optional embodiments. The method may include the patient ingesting a predetermined standardized meal preferably at a predetermined time during the test period. The patient may be classified as a continuous phenotype when the lack of temporal correlation is identified and said symptom severity score indicates the patient's symptom burden is high and consistent throughout the test period. The method may include measuring of spectral gastric activity with an electrode array patch and measuring spatial information of the gastric activity.

According to one embodiment, a method includes monitoring a patient's gastric activity by measuring spectral gastric activity with an electrode array patch over a predetermined test period, concurrently receiving patient symptom information for a predetermined set of symptoms over at least a portion of the test period, determining a measure of gastric activity amplitude from the measured gastric activity data, and displaying a normalized gastric amplitude curve and at least one normalized symptom severity curve over the at least a portion of the test period, overlaid on the same set of axes. The method includes determining a measure of correlation visually and classifying a patient into one of a predetermined phenotype set based on the visually determined measure of said correlation.

The method may include various optional embodiments. The method may include the patient ingesting a predetermined standardized meal preferably at a predetermined time during the test period. The gastric amplitude and symptom severity curves may be normalized by subtracting the mean and dividing by the standard deviation of each curve, and the normalization only being performed when the curves have a standard deviation larger than zero. The time of the meal may be indicated on the display overlaid on the same set of axes. The determined phenotypes may be used by a clinician to provide targeted therapies to patients. The sensorimotor phenotype may be treated as postprandial distress syndrome.

The post-gastric phenotype may be treated as having small bowel/biliary causes. The activity-alleviated phenotype may be treated using a neuromodulator such as mirtazapine or a prokinetic such as erythromycin. The continuous phenotype may be treated as epigastric pain syndrome or a disorder of gut-brain interaction.

According to one embodiment, a method for mapping gastric activity with an electrode array patch disposed over an abdomen skin surface of a patient includes measuring electrical signals associated with gastric activity of the patient with the electrode array patch over a predetermined time period, concurrently receiving patient gastric emptying breath testing (GEBT) information over the predetermined time period, determining one or more normalized biometrics over at least a portion of the predetermined time period from the measured electrical signals, and determining a gastrointestinal phenotype associated with gastroparesis of the patient based at least in part on the one or more normalized biometrics and the GEBT information.

The method may include various optional embodiments. The method may include that the one or more normalized biometric includes at least one of a principal gastric frequency (PGF), a body mass index (BMI)-adjusted amplitude, Gastric Alimetry Rhythm Index (GA-RI), fed-fasted amplitude ratio (ff-AR), and a meal response ratio (MRR). Where the MRR is greater than 1, the gastrointestinal phenotype may be a normal meal response phenotype. Where the MRR is less than or equal to 1, the gastrointestinal phenotype may be a lagged meal response phenotype. The gastrointestinal phenotype may include at least one of a high frequency phenotype and an unstable phenotype.

Other embodiments and variations thereof will become apparent from the following description which is given by way of example only and with reference to the accompanying drawings.

It is acknowledged that the term 'comprise' may, under varying jurisdictions, be attributed with either an exclusive or an inclusive meaning. For the purpose of this specification, and unless otherwise noted, the term 'comprise' shall have an inclusive meaning, allowing for inclusion of not only the listed components or elements, but also other non-specified components or elements. The terms 'comprises' or 'comprised' or 'comprising' have a similar meaning when used in relation to the system or to one or more steps in a method or process.

As used hereinbefore and hereinafter, the term "and/or" means "and" or "or", or both. As used hereinbefore and hereinafter, "(s)" following a noun means the plural and/or singular forms of the noun. As used hereinbefore and hereinafter, the term "continuous" or "semi-continuous" with respect to the test period is to be interpreted as ongoing throughout the entire or nearly entire test period.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are described by way of example only and with reference to the drawings.

Figure 1:
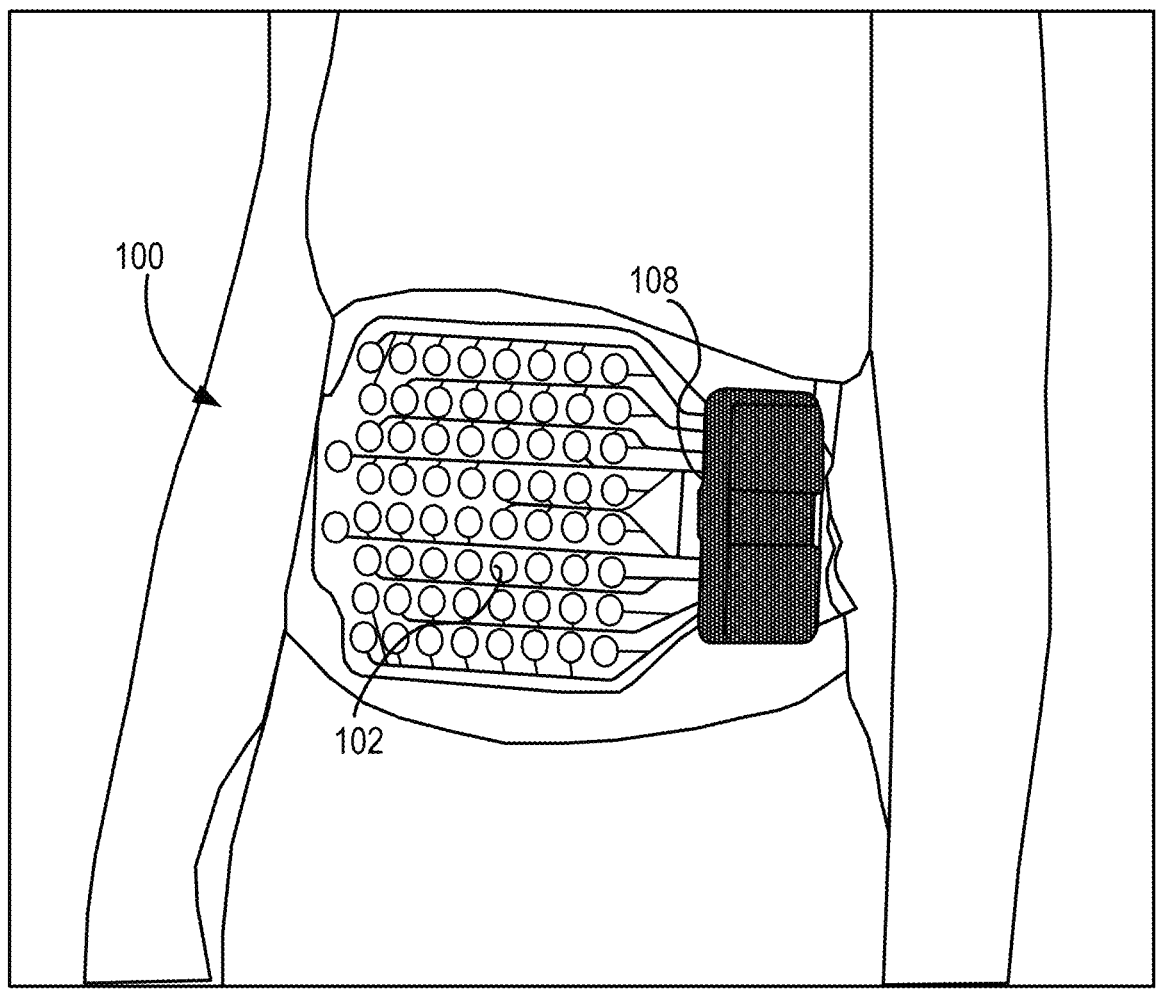
FIG. 1 is an image of a body surface gastric mapping system shown on a patient wearing a sensing electrode array patch and data acquisition device, in accordance with various embodiments of the present invention.

For purposes of the description hereinafter, the terms "upper", "lower", "right", "left", "vertical", "horizontal", "top", "bottom", "lateral", "longitudinal" and derivatives thereof shall relate to the teachings herein as it is oriented in the drawing figures. However, it is to be understood that the variations of the teachings herein may assume various alternative variations, except where expressly specified to the contrary. It is also to be understood that the specific devices illustrated in the attached drawings and described in the following description are simply exemplary embodiments. Hence, specific dimensions and other physical characteristics related to the embodiments disclosed herein are not to be considered as limiting.

DETAILED DESCRIPTION

The present invention provides non-invasive assessment of gastric function using electrophysiological analysis and digital symptom profiling of the gastric conduction system to provide actionable biomarkers that stratify patients into therapeutic groups (e.g., such as groups where gastric dysfunction is present versus absent) to provide a roadmap for personalized (e.g., patient specific) therapy.

Embodiments of the teachings herein may allow for the gathering, combination, and analysis of multiple data sources potentially relevant to understanding gastric dysfunction. In particular, gastric activity data is measured (particularly with respect to post meal stimulus), while concurrently gathering temporally synchronized patient symptom information across a test period. Data associated with various embodiments described herein has shown that Body Surface Gastric Mapping (BSGM) biomarkers, to be described in further detail below, are clinically meaningful, because they achieve correlations with symptom severity, which was not achieved by scintigraphy or other tests. BSGM biomarkers and associated gastrointestinal phenotypes as described herein are ideally suited to applications in pediatrics due to their safe and non-invasive nature, and in view of the limited availability and utility of existing diagnostic tests.

Gastric pathophysiology is complex, with diverse putative mechanisms including impaired fundic accommodation, gastric dysrhythmias, immune activation, abnormal duodenal signaling, autonomic dysfunction, microbiome and psychological (brain-gut) influences, visceral hypersensitivity, pyloric dysfunction, etc. Various embodiments of the present disclosure contribute objective motility diagnostic data, correlating with symptoms, in greater than 60% of patients and, in greater than 90% of those with myenteric/interstitial cell of Cajal (ICC) network pathologies, thereby dramatically improving upon standard of care gastric emptying (~23% detection rate for abnormalities). Such results directly inform clinical management, by stratifying patients into therapeutic groups where gastric dysfunction is present versus absent, as a roadmap to personalize therapy.

Various embodiments of the present disclosure include a medical apparatus for monitoring electrical activity including a sensing device such as an electrode patch or a plurality of patches having one or more electrodes and a connector device (or devices) which may be an electronic device such as a data acquisition device that is in electronic communication with such patch. Advantageously, various embodiments of the present disclosure provide an electrode patch connection system for a non-invasive medical apparatus that may be worn by a subject to monitor the physiological condition in a comfortable and reliable manner, while the subject is engaged in normal daily activities, and/or in a clinical test setting.

Figure 2:
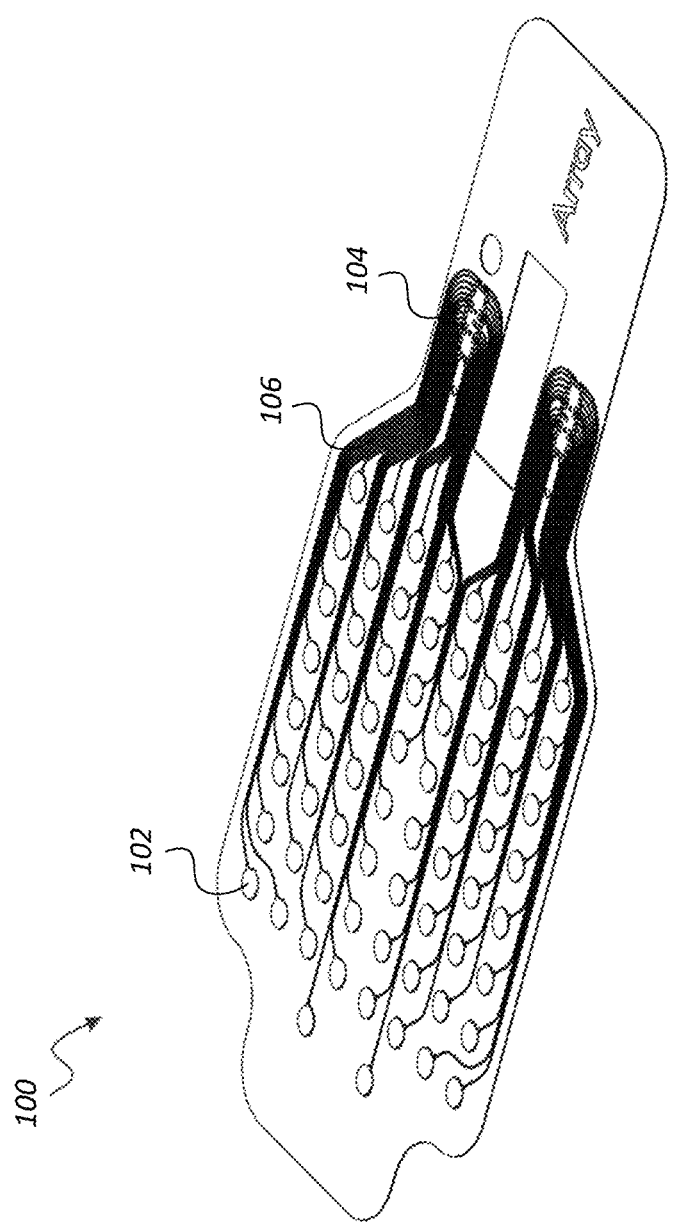
FIG. 2 is a detailed plan view of the sensing electrode array patch of FIG. 1, in accordance with various embodiments of the present invention.

FIGS. 1 and 2 illustrate an exemplary electrode patch 100 for monitoring physiological functions on a subject. According to various embodiments, the subject is a human in some implementations but optionally the subject may be a non-human animal. The electrode patch 100 is configured in some embodiments to be used as part of a system for monitoring gastro-intestinal (GI) electrical activity of a subject. In some embodiments, the electrode patch 100 may be configured to monitor electrical/physiological activity on other regions of the subject such as, but not limited to, colonic regions.

The electrode patch 100 is a sensing device and may include a plurality of spatially arranged surface electrophysiological sensors in the form of electrodes 102 for contacting an outer surface of the skin of the subject to sense and measure electrical potentials at multiple electrodes. Embodiments of the electrode patch 100 are not to be limited by the exemplary embodiment shown in FIG. 1.

As shown in the exemplary embodiment of FIG. 2, there are total of 66 electrodes out of which 64 electrodes are arranged in an array of 8 rows and 8 columns and the remaining two electrodes are the ground and reference electrodes. In use, electrical potentials may be measured as the difference between each of the 64 electrodes and the reference electrode. The ground electrode may be the "driven right leg" or "bias" electrode. The purpose of the ground electrode in some embodiments is to keep voltage level of the subject's body within an acceptable range and to minimize any common-mode in the subject's body (e.g., 50/60 Hz power-line noise). The driven right leg may act as a source or sink. However, the electrode patch 100 may comprise more than 66 electrodes or less than 66 electrodes. The ground and reference electrodes may be different than what is shown in FIG. 2. In an embodiment, the patch may comprise less than, greater than, or equal to 3, 4, 5, 6, 7, 8, 9, 10, 15, 20, 25, 30, 35, 40, 45, 50, 55, 60, 65, 70, 75, 80, 85, 90, 95, 100, 125, 150, 175, 200, 225, 250, 275 or 300 electrodes any value or range of values therebetween in 1 increments (e.g., 33, 94, 44 to 192, etc.).

In some embodiments, the electrode patch 100 is configured to be removably attached to the outer surface of the skin of the subject, such as at or near an abdominal region (as shown in FIG. 1), so that the electrodes 102 contact the outer surface of the skin of the subject at or near the abdominal region to sense and measure electrical signals from the GI tract of the subject. If the electrode patch 100 is for sensing and measuring electrical signals from other regions, then the electrode patch may be configured to be removably attached to the outer surface of the skin of the subject at or near at suitable regions, so that the electrodes 102, contact the outer surface of the skin of the subject at or near such region to sense and measure electrical signals from the that region of subject's body.

In various embodiments, the electrode patch 100 and data acquisition system may be as described in International Patent Application Publication No. WO 2021/130683 which is hereby incorporated by reference in its entirety for all purposes. For example, the electrical traces 106 may connect each electrode 102 and/or to a respective contact pad 104, for operatively coupling with a data acquisition device 108 (interchangeably referred to herein as a connector device, a connection device, etc.). For example, the data acquisition device 108 may be coupled to the electrode patch 100 and wirelessly coupled to a processor. The data acquisition device 108 may be configured for transmission of the measured electrical signals to the processor. Furthermore, the system may include a patient mobile device (e.g., a smart phone, tablet, or the like) for patient symptom information input and the patient mobile device may be in wireless communication (e.g., Bluetooth or the like) with the processor for transmission of patient symptom information. The system may comprise a docking device having a compartment that is configured to receive the data acquisition device of the sensor array. The docking device may be a wireless charging device for facilitating wireless charging of the data acquisition device when docked. The electrode patch and data acquisition system enable body surface gastric mapping (BSGM) information to be received in an autonomous or semi-autonomous manner.

Additionally, the system may include a display for displaying a generated report as described in further detail herein. The display may be part of the patient mobile device or of a separate device used by the health care professional.

BSGM as used herein measures the cutaneous dispersion of gastric myoelectrical potentials (typically μV), arising from extracellular ion current flows during depolarization and repolarization of gastric tissues. This encompasses both gastric slow wave activity, generated and propagated by interstitial cells of Cajal (ICC), and coupled smooth muscle contractions. The underlying sources are complex, because multiple waves (e.g., 3 or 4) simultaneously propagate through the human stomach, traveling at a slow velocity of about 3 mm/s prior to the terminal antral acceleration. In some embodiments, these features correspond to a scenario where gastric potentials recorded at the body surface cannot be definitively related to a single specific wave sequence, as in electrocardiogramstead must be considered as a summation of such sources.

Figure 4:
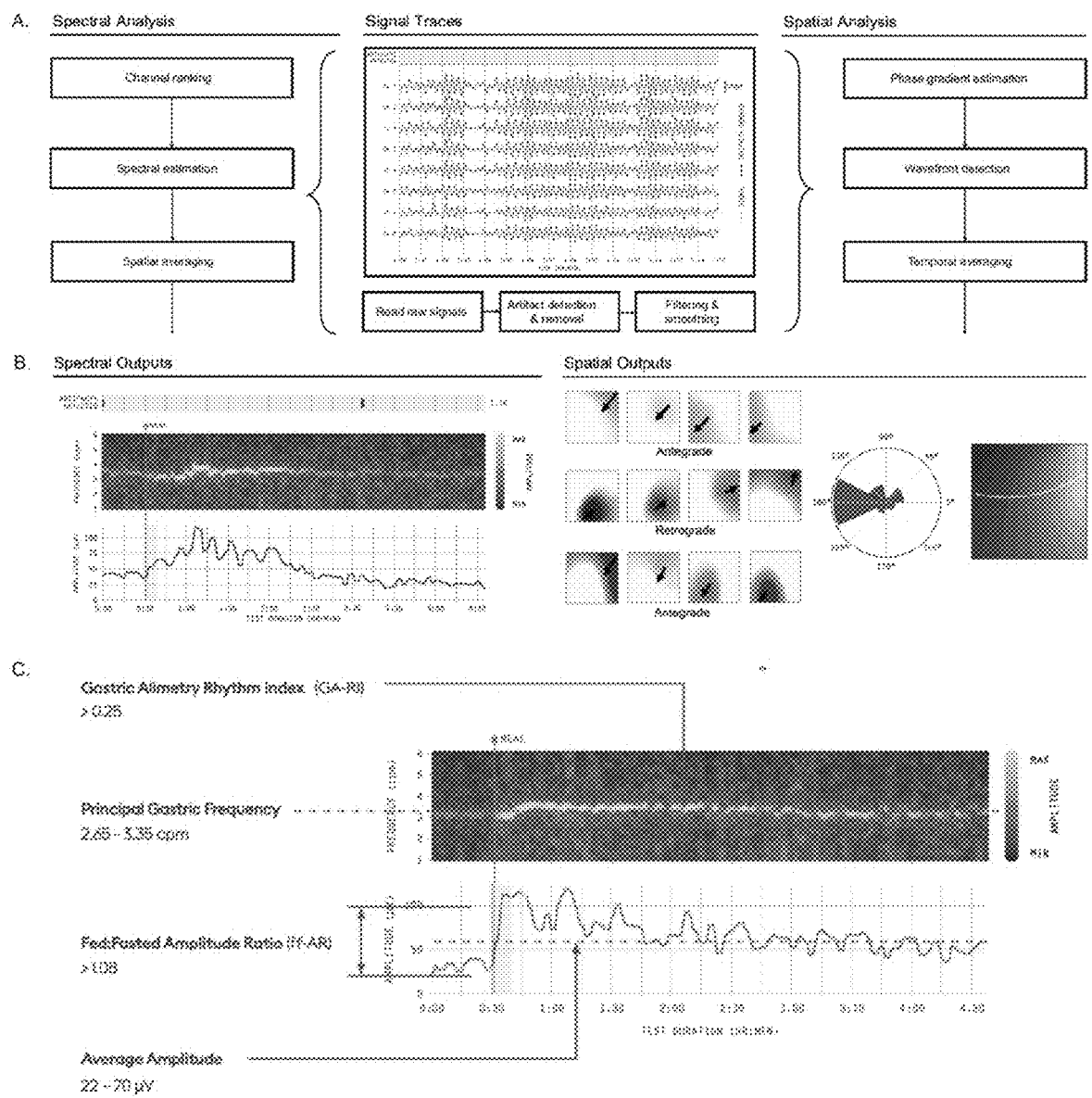
FIG. 4 is a graphic representation of the body surface gastric mapping system, in accordance with various embodiments of the present invention.

Embodiments of the present disclosure may use an electrogastrography (EGG) morphology that provides a distinct 3 cycle per minute (cpm) waveform, for example, when gastric slow waves are entrained to a single frequency, such that dominant frequency is captured in the body-surface potential (FIG. 4).

In some embodiments, an electrode patch according to embodiments described herein may be used to measure gastric activity in response to a meal stimulus. In further embodiments, testing is implemented through a standardized system to output high quality data and data for comparison purposes. A test protocol may include that the participant fast for at least 6 hours and avoid medications modifying gastric function as well as caffeine and nicotine on the day of testing. Embodiments may include fasting for at least 2, 3, 4, 5, 6, 7, 8, 9, 10 hours or more or any value or range of values therebetween in 15-minute increments. Tests may be, in some embodiments, conducted in the morning. The fasting may be linked to the onset of testing (e.g., fasting for at least 2 hours would correspond to starting the testing 120 minutes after food was last consumed).

Figure 3:
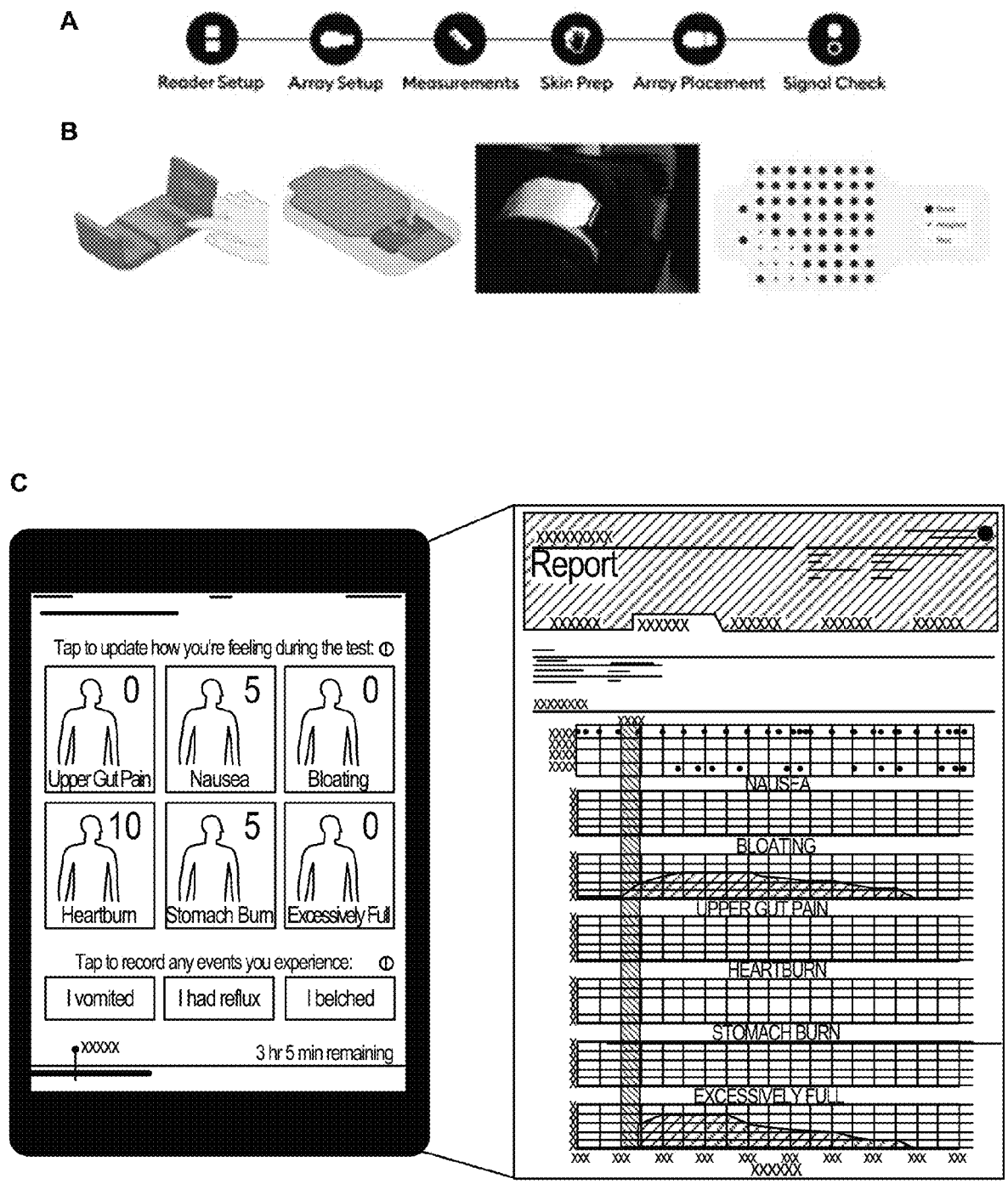
FIG. 3 is a pictographic representation of steps to set up the gastric activity reader system, a display for logging patient symptoms, and an exemplary symptom report page, in accordance with various embodiments of the present invention.

FIG. 3 is a pictographic representation of steps to set up the gastric activity reader system. Part A details basic steps to prepare array on a patient. Part B illustrates coupling of an array with a reader/data acquisition device, and electrode signal check. Part C illustrates an example mobile application used by a patient, for example, to log real time (and concurrent) symptom data and an example report of patient symptom data (e.g., the symptom severity curve) over the time of the test, to be described in further detail below.

Sensor array placement may be preceded by shaving, followed by skin preparation with an exfoliant conductive gel such as NuPrep® (Weaver & Co, CO, USA) to minimize impedance. According to some embodiments, a mobile application for use with electrode array patch and the reader/connection device may be provided for performing an impedance threshold check prior to allowing recording (see FIG. 3, part A). Fasted recordings may be performed for 30 minutes, for example, followed by standardized meal consumed over a predetermined time period (e.g., 10 minutes). In some embodiments, a predetermined test period up to a 4-hr postprandial recording is performed. For example, a 4-hr postprandial recording period may capture a full gastric activity cycle including meal responses that may be delayed with peak BSGM responses occurring 2-4 hrs after a meal. In other embodiments, a predetermined test period may be 30 to 60 minutes, and preferably around 45 minutes. Accordingly, in an embodiment, fasted recordings are performed for less than, greater than, or equal to 10, 15, 20, 25, 30, 35, 40, 45, 50, 55, 60, 65, 70, 75 or more minutes or any value or range of values therebetween in 1-minute increments, contiguous. In some embodiments there is postprandial recording period of less than, greater than, or equal to 0.2, 0.25, 0.5, 0.75, 1, 1.5, 2, 2.5, 3, 3.5, 4, 4.5, 5, 5.5, 6, 6.5 or 7 hours or more or any value or range of values therebetween in 0.5-minute increments. According to an exemplary embodiment, a predetermined time period may include one or more of a 30 minute fasting period, a 10 minute meal window, and a 4 hour post-prandial observation.

In various embodiments, a standard test meal may comprise an off-the-shelf nutrient drink (e.g., Ensure 232 kcal, 250 mL; Abbott Nutrition, IL, USA) and oatmeal energy bar (e.g., a Clif Bar with 250 kcal, 5 g fat, 45 g carbohydrate, 10 g protein, 7 g fiber; Clif Bar & Company, CA, USA). In exemplary embodiments, the calorie consumption of the standard meal is less than, greater than, or equal to 150, 200, 250, 300, 350, 400 or 450 kcal or any value or range of values therebetween in 10 kcal increments. In an embodiment, a standardized meal is consumed within less than, greater than, or equal to 30, 25, 20, 15, 10, 9, 8, 7, 6 or 5 minutes or any value or range of values therebetween in 1-minute increments continuous from beginning to end. In some embodiments, the fat, carbohydrate, protein and/or fiber may have a nutritional value less than, greater than, or equal to 30, 35, 40, 45, 50, 55, 60, 65, 70, 75, 80, 85, 90, 95, 100, 125, 150, 175 or 200% or more or any value or range of values therebetween in 1% increments. The fat, carbohydrate, protein and/or fiber may have varied amounts thereof.

According to various embodiments, meals with similar nutritional composition may be substituted per availability or for patients with specific dietary needs, such as those with diabetes or gluten intolerance. For example, various embodiments described herein may be used in combination with testing for monitoring and managing blood sugars in diabetics during testing as hyperglycemia may induce gastric myoelectrical abnormalities. In various embodiments, the standardized meal is designed to stimulate gastric symptoms in patients with diverse gastric disorders, including milder degrees of functional dyspepsia. In some embodiments, the percent of the standardized meal that is consumed is less than, greater than, or equal to 25, 30, 35, 40, 45, 50, 55, 60, 65, 70, 75, 80, 85, 90, 95, 100, 125, 150, 175 or 200% or more or any value or range of values therebetween in 1% increments.

In various embodiments, nothing is consumed for greater than, or equal to 0.5, 1, 1.5, 2, 2.5, 3, 3.5, 4, 4.5, 5, 5.5 or 6 hours or more or any value or range of values therebetween in 3-minute increments before and/or after the aforementioned timeframe. In an embodiment, only de minimus foods are consumed (e.g., a mint for example) within those times, while in other embodiments, nothing is consumed.

Various embodiments include minimizing movement, talking, sleeping and avoiding touching the electrode array patch to reduce artifact contamination, other than overlying clothes or blankets, etc. In some embodiments, patients are positioned in a comfortable chair that is reclined at 30, 35, 40, 45, 50, 55, 60, 65, 70 or 75 degrees or any value or range of values therebetween in 1-degree increments, and in some embodiments, with their legs elevated, to reduce and/or avoid abdominal wall contractions. In some embodiments the selected chair may be locked in a set reclined position, or at least prevented from moving more than a certain range (e.g., within 1, 2, 3, 4, 5, 6, 7, 8, 9, 10, 11, 12, 13, 14, 15, 16, 17, 18, 19, 20, 21, 22, 23, 24 or 25 degrees or any value or range of values therebetween in 1 degree increments), so as to reduce restless abdominal tensing which may contaminate data with electromyographic noise. During the test, patients may move for comfort adjustments or bathroom breaks with, in at least some embodiments, an on-board accelerometer data being tracked to identify periods of motion.

In some embodiments, patient symptom information is gathered, and symptom profiling occurs substantially concurrently to BSGM testing. Temporal associations between physiological events and symptoms may be used to inform mechanistic interpretations. Accordingly, a patient symptom-logging application (such as shown in FIG. 3, part C) is provided in at least some embodiments to differentiate symptoms with severity lying on a continuum or specific events. In other embodiments, patient symptom information may be collected manually and later entered into the system for quantification and analysis.

For example, gastrointestinal symptoms including one or more of nausea, bloating, upper gut pain, heartburn, stomach burn, excessive fullness, etc., are assessed on a continuum. Discrete events such as episodes of vomiting, reflux, belching, or the like may be time stamped.

Continuous symptoms are assessed during the test at suitably granular intervals. For example less than, greater than, or equal to 2, 3, 4, 5, 6, 7, 8, 9, 10, 11, 12, 13, 14, 15, 16, 17, 18, 19, 20, 21, 22, 23, 24, 25, 26, 27, 28, 29 or 30 or any value or range of values therebetween in 1 increment minute intervals may be used in some implementations. In an embodiment, 10, 15, 20, 25, 30, 35, 40, 45, 50, 55, 60, 70, 80, 90, 100, 125, 150, 175 or 200 or more or any value or range of values therebetween in one increment assessments are made during the test. In an embodiment, the assessments are spaced apart by any one or more the time intervals.

Symptom information may be entered via a pictographic interface (such as on a GUI of a computer or smart phone or smart device, etc.) that aids accurate standardized reporting, for example using a 0-10 visual analog scale (where 0 indicates 'no symptom' and 10 indicates the 'most severe extent' of a symptom). A speech to text system may be used where the patient describes the experience. Any responses may be time stamped. The patient may be prompted by the computer or smart device, such as audibly or in a tactile and/or visual manner, etc.

FIG. 4 is a graphic representation of the body surface gastric mapping system. Part A shows example process steps for analysing raw electrode signal data, into Spectral analysis and/or Spatial analysis. Part B shows example spectral visual outputs from raw data, and example spatial visual outputs from raw data. Part C is a typical gastric activity spectral output graph showing calculated properties for the biomarkers described herein such as rhythm index, principal gastric frequency, fed: fasted amplitude ratio, and average amplitude. Patient symptom inputs may be used to generate a symptom curve (e.g., function) that may be used for data analysis and/or a report that may be standardized, that covers the course of the test meal. According to various embodiments, the data correlates with patients' overall symptom burden and quality of life.

BSGM analytics including the biomarkers, interchangeably referred to as normalized metrics, metrics, or markers, are used, in some embodiments, to generate one or both categories of metrics including spectral metrics which encompass frequency, amplitude, rhythm stability, and meal responses or spatial metrics which describe spatiotemporal dynamics of slow waves projected to the body surface.

An overview of these metrics is provided in FIG. 4. In this example, spectral metrics are derived from the spectrogram, akin to a high resolution EGG for example, generated from those channels with the highest SNR on the array (in an embodiment, it is the highest 50, 55, 60, 65, 70, 75, 80, 85, 86, 87, 88, 89, 90, 91, 92, 93, 94, 95, 96, 97, 98 or 99% or any value or range of values therebetween in 1% increments). Spatial metrics may reflect summated depolarizations across the array which may resolve the predominant direction of wave propagation, and the stability of slow wave patterns. In an exemplary embodiment, the signals from the electrode array patches are sufficiently temporally fine such that the signals may be utilized to identify wave propagation in the patient. In an exemplary embodiment, features associated with the wave propagation are correlated with the symptom indication information from the patient to identify one or more of the phenotype sets disclosed herein. In an exemplary embodiment, a trained neural network is utilized to evaluate the spatial metrics, and, in conjunction with the input from the patient, or otherwise in conjunction with data based on the input from the patient, any one or the analysis and/or determining actions, etc., detailed herein may be executed. In some embodiments, the neural network may be trained on a sufficient number of spatial metrics and other data sets to enable the product of the trained neural network to make determinations based thereon.

Various embodiments include customized BSGM spectral metrics having various reference intervals. The metrics may include principal gastric frequency, body mass index (BMI)-adjusted amplitude, Gastric Alimetry Rhythm Index (GA-RI), fed: fasted amplitude ratio (ff-AR), etc. Principal gastric frequency may be defined as the intrinsic gastric frequency, which is observed as a dominant band in the spectrogram, reported in cycles per minute (cpm). The reference interval for principal gastric frequency may be between 2.65 cpm and 3.35 cpm (e.g., based on a normal adult BSGM analysis). GA-RI may be defined as measure of stability (between 0-1) of the gastric activity. The GA-RI quantifies the extent to which activity is concentrated within a narrow frequency band over time, relative to the residual spectrum. Higher values indicate greater stability, whereas lower values indicate greater spectral scatter. The reference interval for GA-RI may be greater than or equal to 0.25 (e.g., based on a normal adult BSGM analysis). BMI-adjusted amplitude may be defined as amplitude of the gastric signal corrected for the attenuation resulting from increasing BMI, reported in microvolts ($\mu V$). The reference interval for BMI-adjusted amplitude may be between 22 $\mu V$ and 70 $\mu V$ (e.g., based on a normal adult BSGM analysis). The ff-AR may be defined as the increase in signal power arising after a test meal, calculated by taking a ratio of the maximum amplitude in any single 1-hour postprandial period to the amplitude in the pre-prandial period. The reference interval for ff-AR may be greater than 1.08 (e.g., based on a normal adult BSGM analysis).

In some embodiments, frequency measurements are susceptible to contamination by high-amplitude low-frequency transients arising from motion artifacts and by periodic adjacent colonic activity. Accordingly, the principal gastric frequency metric may be used to overcome this pitfall by measuring only the sustained frequency (or weighting the sustained frequency higher than others, such as by at least 2, 3, 4, 5, 6, 7, 8, 9, 10, 15, 20, 25 or 30 or more times or any value or range of values therebetween in 1 increments) within the plausible gastric range, while excluding other transients and irregularities irrespective of their influence on the power spectrum (or weighting those downward, such as by the inverse of any of those weightings).

Furthermore, amplitude measurements may be confounded by BMI due to signal attenuation through abdominal adipose. A BMI-adjusted amplitude metric according to embodiments described herein using a multiplicative regression model, enables comparison of amplitudes across populations up to a current test threshold of BMI 35.9.

Legacy EGG metrics for assessing the stability of gastric rhythm may include 'percentage bradygastria' and 'percentage tachygastria', which conflate frequency with rhythm stability, and the 'instability coefficient', which is often incorrectly motivated due to its dependence on frequency. GA-RI, according to embodiments described herein, provides a metric of stability including a measure of concentrated gastric activity within a narrow gastric frequency band over time relative to the residual spectrum. The GA-RI is scaled between 0 (no rhythm stability) and 1 (maximum rhythm stability) and is independent of frequency.

The gastric meal response, as measured by postprandial amplitude curves, demonstrates considerable temporal variability. For example, a study of 110 control subjects showed that the median time of peak amplitude was 1.6 h (IQR 0.7-2.7 h) after meal completion. EGG power-ratio calculations are typically based on shorter intervals, such as the initial 45-minute postprandial period, potentially underestimating the gastric meal response. Accordingly, the ff-AR metric described herein measures the gastric response based on the maximum amplitude in any single 1-hour period of a 4-hour postprandial window and is therefore adaptive to variable meal response profiles.

Figure 5:
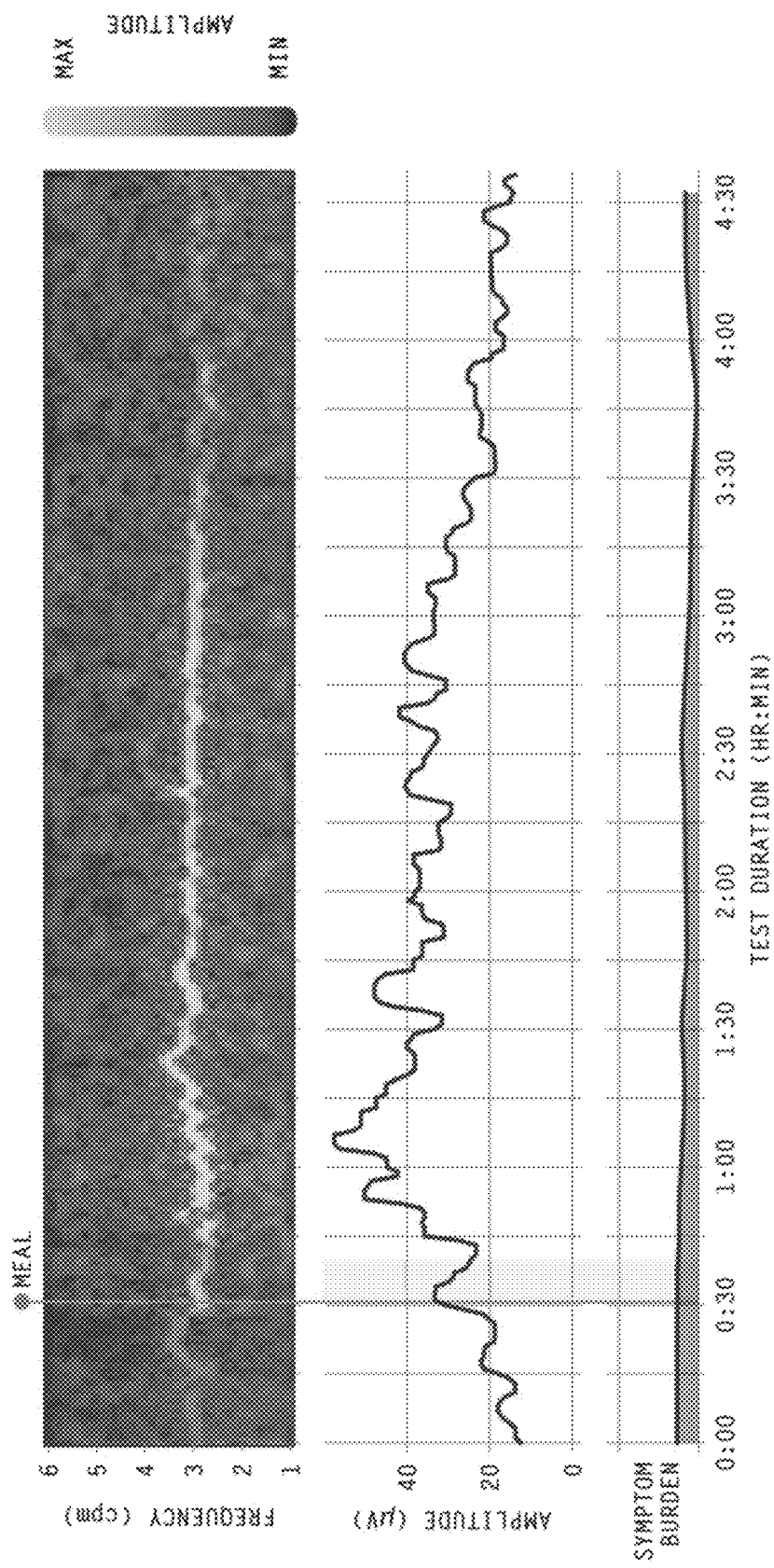
FIG. 5 is an output plot for a normal phenotype, including a spectral plot, a plot of amplitude extracted from the raw electrode data, and a plot of overall symptom burden, in accordance with various embodiments of the present invention.

FIG. 5 presents an example output plot for a typical (normal) patient, showing a spectral plot (top), a plot of amplitude extracted (normalized) from the raw electrode data (middle), and a plot of overall symptom burden extracted from a symptom logging mobile application provided to the patient (bottom). According to some embodiments, the reference intervals for the four BSGM spectral metrics were developed from a cohort of healthy volunteers of diverse age, sex, and ethnicity, with cross-validation analysis demonstrating external validity. These intervals were generated for participants aged≥18 years with BMI<35 kg/m2, where >50% of the meal is consumed during the test and <50% of the test duration is affected by artifacts. These reference intervals, summarized FIG. 4, part C, are used to guide clinical interpretations of BSGM data.

Figure 6:
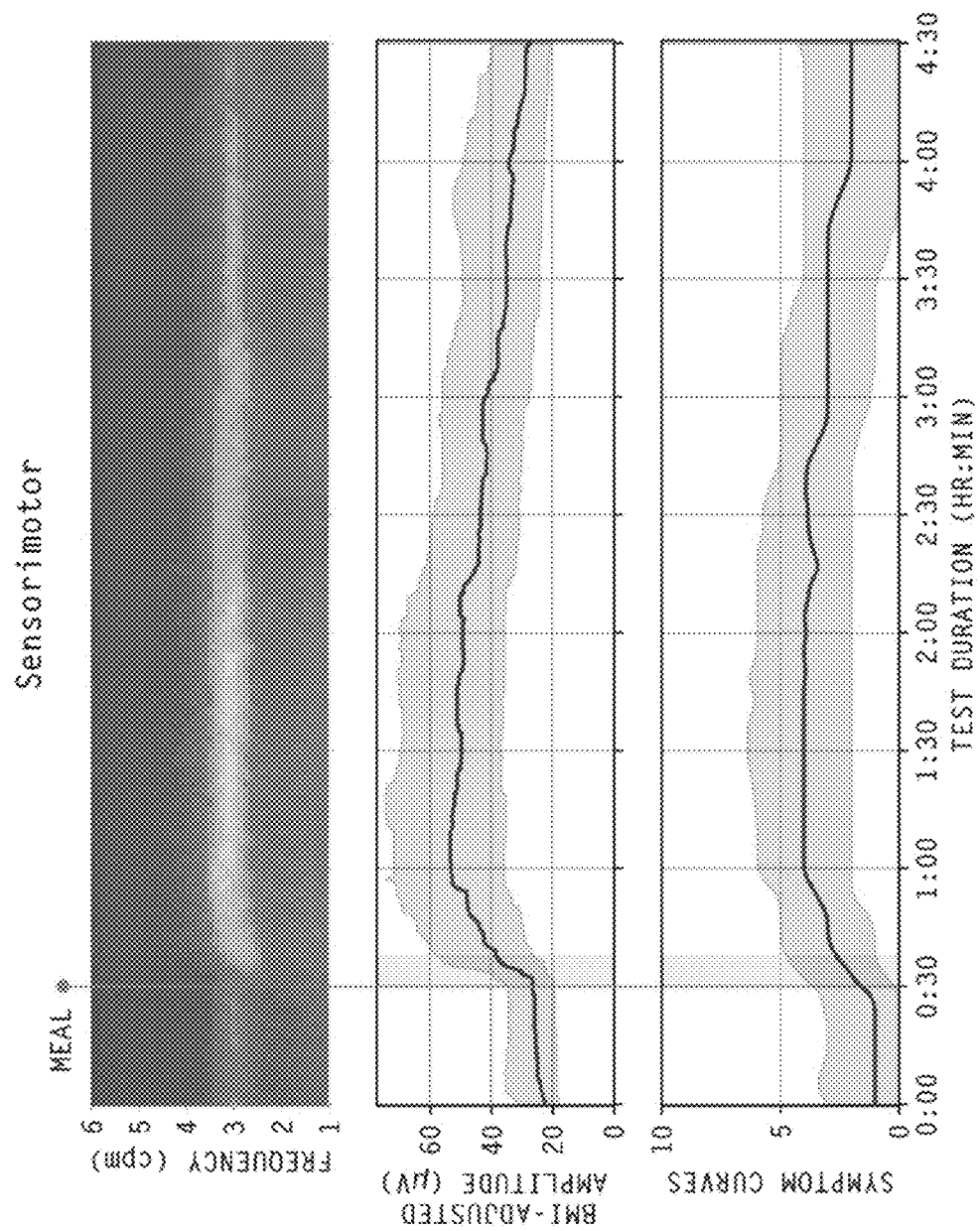
FIG. 6 is an output plot for a sensorimotor phenotype including a spectral plot, a plot of amplitude extracted from the raw electrode data, and a plot of overall symptom burden, in accordance with various embodiments of the present invention.

FIG. 6 is an output plot for a sensorimotor phenotype including a spectral plot, a plot of amplitude extracted from the raw electrode data, and a plot of overall symptom burden. In particular, FIG. 6 is a summary plot of multiple patients with a sensory phenotype combined into a single summary spectral map. A sensorimotor phenotype may be characterized by symptoms that are typically meal-responsive and correlate with gastric amplitude. Hypersensitivity and disordered accommodation are features of both FD and gastroparesis, which are captured together under the 'sensorimotor' symptom profile. Disordered accommodation may be increased when there is a normal spectral analysis in the presence of postprandial distress symptoms that are meal-responsive with a decay curve. Gastric hypersensitivity has a similar profile, although pain may be dominant. Hypersensitivity may coexist with neuromuscular disorders, and/or may be related to past enteric infections, immune activation, dysbiosis, hyperpermeability, and disorders of the gut-brain interaction. Mechanical stimuli including stretch and contractions then trigger hypersensitized pathways, such that symptoms are meal-responsive, correlate with gastric activity, and subside as the stomach empties.

Figure 7:
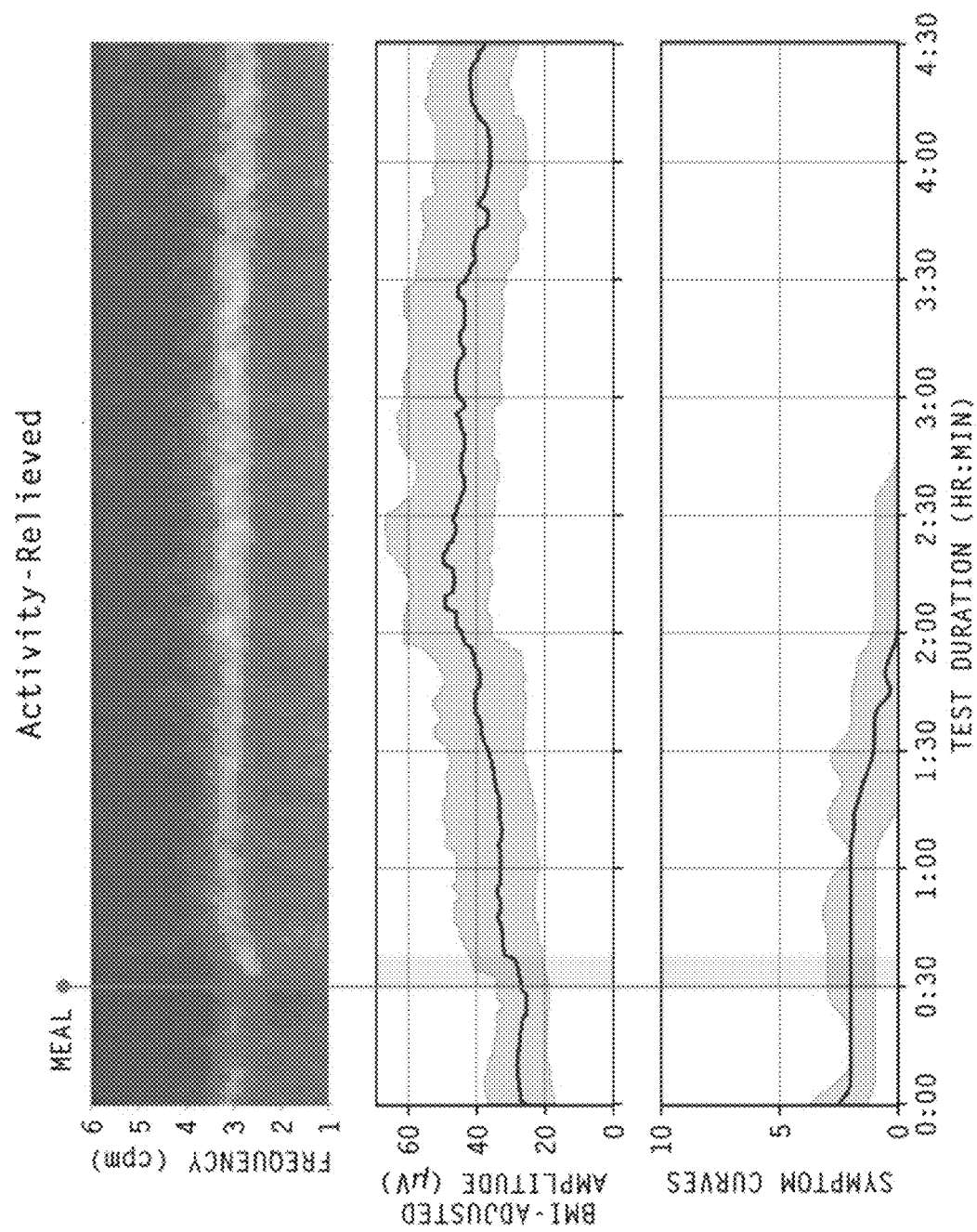
FIG. 7 is an output plot for an activity-relieved phenotype, including a spectral plot, a plot of amplitude extracted from the raw electrode data, and a plot of overall symptom burden, in accordance with various embodiments of the present invention.

FIG. 7 is an output plot for an activity-relieved phenotype, including a spectral plot, a plot of amplitude extracted from the raw electrode data, and a plot of overall symptom burden. In particular, FIG. 7 is a summary plot of multiple patients with the activity-relieved phenotype combined into a single summary spectral map. The symptom/amplitude time lag is thresholded to identify the activity-relieved phenotype (e.g. lag<−0.25).

Figure 8:
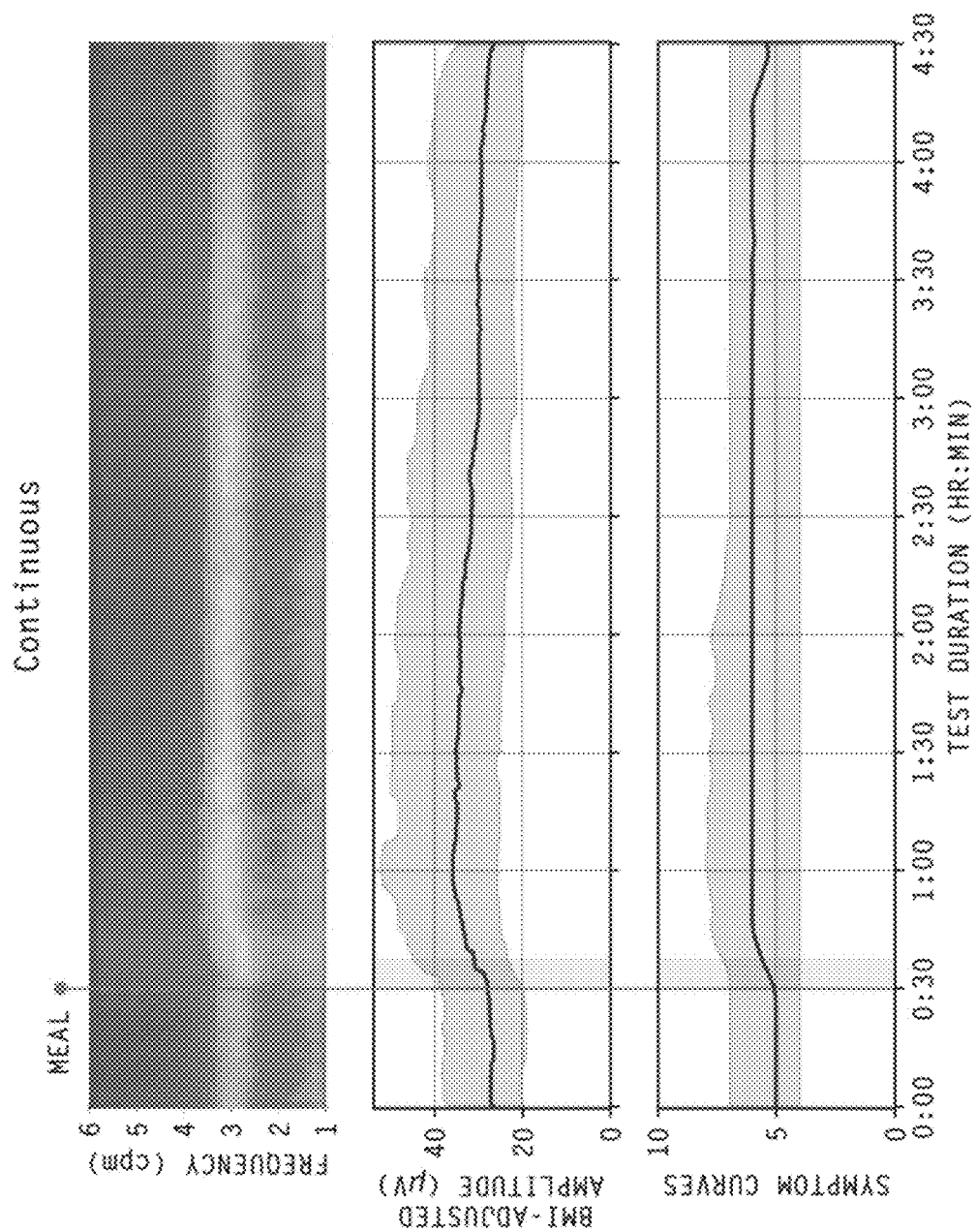
FIG. 8 is an output plot for a continuous phenotype, including a spectral plot, a plot of amplitude extracted from the raw electrode data, and a plot of overall symptom burden, in accordance with various embodiments of the present invention.

FIG. 8 is an output plot for a continuous phenotype, including a spectral plot, a plot of amplitude extracted from the raw electrode data, and a plot of overall symptom burden. In particular, FIG. 8 is a summary plot of multiple patients with the continuous phenotype combined into a single summary spectral map. A continuous phenotype may be characterized by symptoms that are not meal responsive or symptoms that are weakly responsive. Furthermore, symptoms are largely continuous and correlate poorly with gastric amplitude. This phenotype is common and includes near-continuous symptoms in the presence of normal spectral analysis. Importantly, symptoms do not correlate with gastric amplitude, meaning they do not subside as the gastric meal response wanes. This phenotype is observed in association with higher rates of anxiety and depression, indicating a disorder of gut-brain interaction (DGBI) in many patients ('centrally mediated'). In addition, continuous symptoms have also been seen in diabetic neuropathy or post-vagal injury on a neuropathic basis, and can arise due to non-gastric disorders, e.g., colonic, abdominal wall pain syndromes, or other abdominal diseases.

Figure 9:
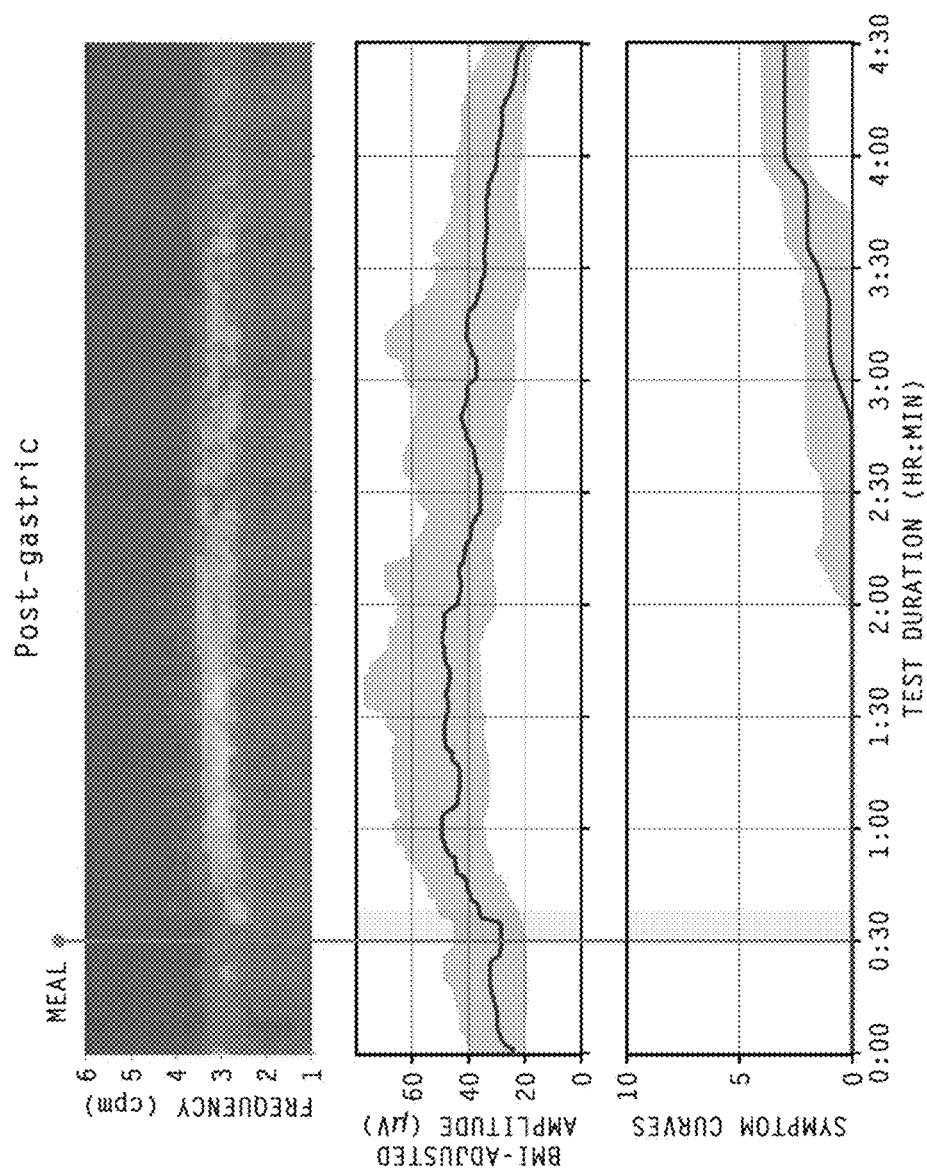
FIG. 9 is an output plot for a post-gastric phenotype including a spectral plot, a plot of amplitude extracted from the raw electrode data, and a plot of overall symptom burden, in accordance with various embodiments of the present invention.

FIG. 9 is an output plot for a post-gastric phenotype including a spectral plot, a plot of amplitude extracted from the raw electrode data, and a plot of overall symptom burden. In particular, FIG. 9 is a summary plot of multiple patients with the post-gastric phenotype combined into a single summary spectral map. A post-gastric phenotype may be characterized by symptoms that trend upwards late in the test and often after gastric amplitude decays. A post-gastric phenotype includes symptoms arising distal to the pylorus. Symptom curves arising from gastric disorders classically peak postprandially then decay; whereas post-gastric symptoms curves trend upward late in the test once gastric emptying proceeds. Comparing the amplitude curves and symptom profiles as described herein can therefore help in diagnosing post-gastric disorders. Related symptoms are more typically 'stomach burn' and bloating. Gastric and post-gastric symptoms may co-exist, indicating pathophysiology of both foregut and midgut. According to various embodiments, the post-gastric phenotype may be associated with a measure of temporal association greater than +0.25 over the predetermined pre-prandial and post-prandial time period.

It will be appreciated that many methods of statistically analysing such data are available to assess whether a correlation exists (or not) and the strength of any correlation (or not). Various mathematical techniques for assessing characteristics of a data stream, to provide a numerical measure of a correlation or characteristic, may be utilized. Data may be normalized to synchronize with the time a standard meal was ingested. Similarly, data may be normalized by applying an offset to allow 'like-with-like' comparison. Further still, normalizing may involve combining data from multiple channels (e.g., from multiple electrodes of the electrode patch 100) into a single curve (e.g., function) representative of the gastric activity during the test period (or at least a portion thereof). Further still, normalizing may include discarding data anomalies, such as dropping electrodes with low signal, or anomalies introduced by patient movement, etc. Further still, normalizing may involve the minimum value of the function (for example gastric amplitude) being subtracted from the whole function, and/or the function (for example the gastric amplitude) being divided by its sum. The effect of demographic parameters (age, sex, and ethnicity) on BSGM have also been evaluated, and while minor differences were found regarding sex, these differences were sufficiently trivial to allow a single common set of adult reference intervals.

Various embodiments of the present invention quantify and classify a specific set of patient symptom profiles, and their relationships to simultaneously recorded gastric activity. The embodiments disclosed herein may facilitate quantitative analyses of the role of symptoms in clinical assessment of gastroduodenal disorders at scale. Robust metrics are included to quantify physiological characteristics and symptom profiles into objective symptom phenotypes. Various characteristics, the associated metrics and phenotypes, and their clinical implications are further discussed below.

A standardized digital classification framework has been provided that is capable of separating patients into those with abnormal spectral analyses (e.g., suspected neuromuscular pathologies), normal spectral analyses with symptoms correlated to gastric amplitude (e.g., a sensorimotor phenotype, a post-gastric phenotype, or an activity-relieved phenotype) and symptoms independent of gastric amplitude (e.g., a continuous phenotype, a meal-relieved phenotype, or a meal-induced phenotype).

According to embodiments described herein, gastric activity resulting in spectral abnormalities is strongly associated with daily symptom severity and poor quality of life. Furthermore, patients having spectral analyses that are normal, and symptom patterns independent of gastric amplitude (e.g., a continuous phenotype, a meal-relieved phenotype, or a meal-induced phenotype) are more strongly correlated with depression and anxiety. Specifically, patients with a normal spectrogram, considered to indicate an intact gastric neuromuscular system, and a symptom profile unrelated to gastric activity (e.g., continuous, meal-induced, and meal-relieved) have the strongest correlations with depression and anxiety scores. Conversely, those with abnormal spectrograms had relatively low depression scores. The important clinical implication of this finding is that patients may be divided into primarily DGBI and neuromuscular subgroups. Accordingly, embodiments described herein provide improved patient selection for principally psychological therapies versus gastric-targeted therapies such as prokinetics and neuromodulation.

Embodiments of the present invention have determined that patients with chronic nausea and vomiting disorders but with normal spectral analyses tend to have worse anxiety and/or depression than patients whose symptoms may be explained by gastric neuromuscular abnormalities. Further, of patients with normal BSGM spectral analyses, pre-meal high symptom severity and persistence of high symptoms throughout the test, is a phenotype highly associated with anxiety and/or depression.

These results indicate that a high pre-meal symptom severity that persists through the test, may be suggestive of disorders linked to the gut-brain axis. This is typically observed with the symptoms that are high throughout the test and yet do not correlate with the gastric amplitude (see FIG. 8). For example, to quantify the symptom persistence, a range metric may be defined as the difference between the 95th and 5th percentile of severity for a particular symptom throughout the test. The continuous phenotype may be identified, for example, by thresholding the range (e.g., range<3) and the $5^{th}$ percentile of the severity (e.g., 5th percentile>2).

Methods may involve monitoring a patient's gastric activity over a test period by receiving data based on spectral gastric activity with an electrode array patch concurrently with patient symptom information (for a predetermined set of symptoms) as described herein. The degree of correlation between patient symptom information and gastric activity amplitude is assessed with a statistical technique. This may include treating for a gut-brain axis disorder if the measure indicates a correlation is absent, or optionally by not satisfying a predetermined correlation threshold. This may also include treating for gastric dysfunction if the measure of said correlation indicates a correlation exists, optionally by satisfying a predetermined correlation threshold. The patient may also be classified as having a continuous phenotype.

A subset of patients exhibit symptoms that are tightly time-synchronized with the gastric amplitude, indicating that these symptoms may have a sensorimotor component and may be suggestive of disorders linked to visceral hypersensitivity (see FIG. 6). According to some embodiments of the present invention, a symptom/amplitude clinical correlation may be used as the correlation coefficient between the symptom severity curve (see for example lowest graph in FIGS. 5-9) and gastric amplitude curve (see for example middle graph in FIGS. 5-9). The symptom/amplitude clinical correlation is thresholded to identify the sensorimotor (e.g., correlation>0.5) phenotype. In an embodiment, where the correlation coefficient is calculated for one or more or all symptom severity curve if a standard deviation is above a predetermined deviation threshold. The predetermined deviation threshold may be 0.05, 0.1, 0.15, 0.2, 0.25, 0.3, 0.35, 0.4, 0.45, 0.5, 0.55, 0.6, 0.65, 0.7, 0.75, 0.8 or more or any value or range of values therebetween in 0.01 increments.

Various embodiments include implementing a temporal correlation coefficient. For example, a maximum temporal correlation coefficient may be used to determine a phenotype for temporal associations between normalized gastric amplitude and normalized symptom severity. In an exemplary embodiment, a sensory motor phenotype is indicated when a maximum temporal correlation coefficient is greater than 0.5.

Accordingly, a method may involve monitoring a patient's gastric activity over a test period by receiving data based on spectral gastric activity with an electrode array patch concurrently with patient symptom information (for a predetermined set of symptoms) as described herein. The method may further include determining a degree of temporal association between the gastric amplitude and continuous symptom severity function(s). The symptoms may be selected from a predetermined set of symptoms and/or for an average symptom function for two or more symptoms selected from the predetermined set of symptoms. If a significant degree of temporal correlation is found, treatment may follow that is appropriate for visceral hypersensitivity, for example. The patient may be optionally classified as having a sensorimotor phenotype. In particular, a maximum temporal correlation coefficient may be used to determine a phenotype for temporal associations between normalized gastric amplitude and normalized symptom severity.

The method may include calculating a temporal correlation coefficient (for example Pearson's r), and based on the coefficient, assessing the temporal synchronization of the normalized gastric activity amplitude function and a normalized symptom severity function. Further, the temporal correlation coefficient may be calculated for each symptom severity curve (or an average symptom curve) if a standard deviation is above a predetermined standard deviation threshold. The temporal correlation coefficient (for example Pearson's r) may be calculated for time lags ranging from approximately −10 to +10 minutes, with approximately 1 minute steps, and the correlation may for example be taken as the maximum of these values.

Patients may exhibit symptoms that occur either before the onset or after the conclusion of a physiological gastric meal response, suggesting that symptoms may be related to delayed onset of gastric mixing or a pathology distal to the stomach, respectively (see FIG. 7 and FIG. 9). As a measure of the extent to which either of these patterns occur, the symptom/amplitude time lag may be defined by the average difference between the cumulative distribution functions of symptom and amplitude (−1 indicates all symptoms occurring before all gastric activity, and +1 all symptoms occurring after gastric activity). The symptom/amplitude time lag may be thresholded to identify the activity-relieved (e.g., lag<−0.25, see FIG. 7) or post-gastric (e.g., >0.25, see FIG. 9) phenotypes.

Based on the above scheme, the symptom metrics for the symptom severity curves profiled for nausea, bloating, upper gut pain, heartburn, and stomach burn may be based on tests performed on patients with chronic gastroduodenal symptoms. Symptom curves associated with each phenotype may be visualized using the median curve and the associated interquartile range (IQR). For phenotypes relating symptom severity to gastric amplitude, the median (IQR) amplitude curves and average spectrograms for the patients with one or more symptom matching the phenotype are shown at least in FIGS. 5-9 and 18-20.

Accordingly, a method may involve monitoring a patient's gastric activity over a test period by receiving data based on spectral gastric activity with an electrode array patch concurrently with patient symptom information (for a predetermined set of symptoms) as described herein. Further, methods may involve identifying a time lag between the gastric amplitude and one or more symptom severity functions, using statistical techniques, for example cumulative distribution functions (CDFs).

For example, an average difference between cumulative distribution functions (CDFs) may be used to assess the time lag between normalized gastric amplitude and a normalized continuous symptom severity function.

Further, a correlation coefficient may be calculated for one or more respective symptom severity curves (or an average of two or more symptom curves). In various embodiments, a correlation coefficient may be calculated if a standard deviation is above a predetermined deviation threshold. For example, for determining a sensorimotor phenotype, the predetermined deviation threshold may be approximately 0.5 for individual symptom curves, or for example may be 0.1 for an average of two or more symptom curves. According to some embodiments, less than 0.3 may be a weak correlation, between 0.3 and 0.7, inclusive, may be a moderate correlation and greater than 0.7 may be a strong correlation. Accordingly, 0.5 may therefore represent a significant correlation between gastric amplitude and a symptom. If this correlation is present, a patient may be diagnosed with hypersensitivity or accommodation disorder and a recommendation may include GI neuromodulator or fundic relaxant therapies, in contrast to other pathways such as central neuromodulators for DGBIs or promotility/prokinetic drugs which are suited for other types of disorders described herein.

According to at least some embodiments, a threshold correlation may be lowered when at least two symptoms are considered. According to some embodiments, this correlation is performed independently for every symptom. A higher number of symptoms correlating may point more strongly to the diagnosis of a sensorimotor disorder. Having a mixture of symptoms that do and do not correlate may point to a mixed or overlapping phenotype. Evaluating a number of symptom correlation plots together enables focused management of one or more causative factors.

In some embodiments, the time lag is quantified as the average difference between the CDF of the normalized gastric amplitude function and the CDF of the normalized symptom severity function. Accordingly, the time lag is thresholded to determine phenotypes associated with symptoms that either precede or follow gastric activity. A post-gastric phenotype of symptoms following gastric activity is indicated if said time lag is greater than 0.25, or an activity-alleviated phenotype if symptoms preceding gastric activity is indicated when said time lag is less than −0.25. According to some embodiments, the post-gastric phenotype may be treated as having small bowel/biliary causes and the activity-alleviated phenotype may be treated using a neuromodulator such as mirtazapine or a prokinetic such as erythromycin.

Various embodiments provide relationship(s) of symptom severity curves with concurrent myoelectrical activity of the stomach. Embodiments provide a standardized approach to quantifying and classifying symptom profiles for relating continuous real time-of-test symptoms to simultaneously recorded real time gastric activity.

In an exemplary embodiment, a method includes receiving data based on measured spectral gastric activity measured with a plurality of electrodes in signal communication with the electrical impulses of a patient. In an exemplary embodiment, the electrodes are part of an electrode array patch as described herein. In an exemplary embodiment, the measured spectral gastric activity is measured with the electrodes during a first temporal test period. In an exemplary embodiment, receiving data based on measured spectral gastric activity, may be executed by receiving a data package with data that is directly or indirectly based on the measurements utilizing the plurality of electrodes.

In an exemplary embodiment, this may be executed by a server that is remote from where the measurements are actually being taken. The data may be provided to a remote location from the clinic where the measurements are being taken (e.g., remote server or cloud server). In an exemplary embodiment, the data may be processed data that is rectified to remove extraneous data channels for example, with the data being weighted, etc. In an exemplary embodiment, the data package may be received in real time during the monitoring/measuring, or may be received after completion of measuring, such as one or two or three or more days after the measuring. In an exemplary embodiment, receiving data occurs no longer than 5, 10, 15, 20, 25, 30, 35, 40, 50, 60, 90, 120, 180, 250, 300, 350, 400, 500, 600, 700, 800, 900, 1000, 1500, 2000, 2500 or 3000 or any value or range of values therebetween in one increment seconds and/or minutes after the completion of the first temporal test. In an embodiment, some of the data may be acquired well before the end of the first temporal period, such as when the data is being received in real time with the measurements. Accordingly, in an exemplary embodiment, the received data includes data elements that correspond to data based on measurements at specific time frames, sometimes during the first temporal period, and the data elements may be received within any of the time frames such as, for example, within 4, 3, 2, 1, 0.75, 0.5, 0.25 or 0.1 seconds of the measurements upon which the data elements being taken are based.

In some embodiments, receiving the data may be executed by taking the measurements utilizing the patch detailed herein. In an exemplary embodiment, at least some of the embodiments of the method disclosed herein are executed by a health care professional utilizing a computer or a device adapted to implement one or more the teachings detailed herein, or otherwise have access to a device or a computer system, etc., or otherwise a system, whether directly or via a link, such as the Internet or the like, etc., which device etc. is configured to implement at least one of the actions detailed herein.

In an exemplary embodiment, the method includes receiving data based on patient symptom information for a predetermined set of symptoms. In this exemplary embodiment, the patient symptom information is received during at least a portion of the first temporal test. In an exemplary embodiment, the patient may provide output (or input, depending on the perspective) indicating the given sensation that he or she is feeling associated with a given symptom. This output may be scaled data according to various embodiments.

In some embodiments, receiving data based on patient symptom information may be executed by, for example, receiving a data package that is based directly or indirectly on the information received from the patient. Receiving data may be executed remote from the location where the patient is located. The data may be received by the same actor that is "managing" the patient. In an exemplary embodiment, the patient is in a clinic and a clinician who manages the patient (e.g., positions the patient in a given chair for example with a specific posture that is desired for example or provides the general set up for the patient, gives the general instruction for example to the patient, places the electrode patch on the patient, etc.) is co-located with the patient. In an exemplary embodiment, it is the person who manages the patient that obtains the data, and/or it is a local computer that obtains the data, such as for example a computer that has an input device configured to receive output from the recipient.

In an exemplary embodiment, the method includes determining data indicative of gastric activity amplitude from the measured gastric activity data. In an exemplary embodiment, the data indicative of gastric activity amplitude is normalized gastric activity amplitude. In an exemplary embodiment, normalizing is executed by the actor who is determining the data indicative of the gastric activity amplitude. In an exemplary embodiment, this may be implemented according to any of the teachings detailed herein. In an exemplary embodiment, this may be executed utilizing a computer and/or processor that is configured with software to execute various embodiments in an automated or semi-automated manner.

In an exemplary embodiment, the method includes correlating the patient symptom information with the data indicative of normalized gastric activity amplitude over the test period. In an exemplary embodiment, the correlations may correspond to those detailed above. An exemplary embodiment, this may be executed utilizing a computer program that is located on a computer, which computer program automatically takes the data detailed above and automatically correlates the data. This computer may execute evaluating the correlation. In an embodiment, this may be by determining a measure of the correlation.

In an embodiment, the correlation is executed for at least 25, 30, 35, 40, 45, 50, 55, 60, 65, 70, 75, 80, 85, 90, 95 or 100% or any value or range of values therebetween in 1% increments of the total test period. In an exemplary embodiment, correlation is contiguous. In an exemplary embodiment, separate parts of the test period are correlated. If movement or some other factor renders some of the data deviant or otherwise reduces the utility of the data, that data may be excluded from the correlation.

The method includes the identification of a treatment for a gut-brain axis disorder if the evaluation of the correlation indicates no clinical correlation exists. A clinical correlation may be based on predetermined thresholds. If the correlation that is determined falls outside a predetermined correlation threshold, in an exemplary embodiment, the method includes identifying the treatment for the gut-brain axis disorder based on such occurrence. Conversely, if the measure of the correlation falls within a predetermined correlation threshold, and identification of a treatment for gastric dysfunction may be executed based on such.

While the above embodiment(s) have often focused on executing the method where the actor need not be one of the parties receiving the measurements, in an alternate embodiment, the actor receiving the measurements does not do one or more of the actions, but instead receives results of the actions and acts based thereon. In an exemplary embodiment, there is a method where the actor obtains first data based on measured spectral gastric activity measured with an electrode array patch during a first temporal test period. This method may further include receiving second data based on patient symptom information for a predetermined set of symptoms, wherein the patient symptom information was received during at least a portion of the first temporal test period. In an exemplary embodiment, the clinician may do the data logging of the symptoms the patient is experiencing, while in other embodiments, the clinician or the clinic is operating a machine that receives the output from the patient, such as from an application that the patient is utilizing. In an exemplary embodiment, the clinician is in another room away from the patient. Here, the clinician is receiving electronic communication from the patient inputted into a computer co-located with the patient for example.

In an exemplary embodiment, this method further includes providing the first and second data. In an exemplary embodiment, this data is provided into a computer that is linked to a remote server that receives the first and second data. This method may be executed by the clinician coordinating data transfer from the system utilized to detect the electrical signals in the patient and/or the clinician coordinating data transfer from the system utilized to collect the symptoms experienced by the patient. This may be done by placing the hardware utilized to collect the data into signal communication, directly or indirectly, with a remote server.

In an exemplary embodiment, the method includes receiving third data, and prescribing a treatment based on the third data. This may be any one or more the treatments detailed above. In an exemplary embodiment, instead of or in addition to prescribing a treatment, based on receiving third data, a diagnosis is made about the medical condition afflicting the patient. In an exemplary embodiment, the third data is an evaluation of a correlation of the first data with data indicative of normalized gastric activity amplitude from the second data.

Various embodiments may include the utilization of a product of a trained neural network to execute one or more of the actions detailed herein. Correlating and/or evaluating the correlation may be executed by a product of the trained neural network. In an exemplary embodiment, this is a chip that results from training of the neural network. In an embodiment, the various method actions herein are executed a sufficient number of times to establish a baseline training for the neural network. Upon the training of the neural network, the product thereof is utilized to execute the evaluation including the correlation, the determination of the measure of normalized gastric activity, etc. Any disclosure herein of any analysis and/or determining and/or measuring action corresponds to an alternate disclosure of utilizing executing such with a trained neural network or more accurately, the product of a trained neural work, providing that the art enables such unless otherwise noted.

The proposed phenotypes may be linked to a physiological mechanism, enabling these phenotypes to guide further studies attempting to link symptom phenotypes with long-term outcomes to treatments and interventions. Also, embodiments establish a standardized and fully quantitative system for characterizing symptoms.

Additional phenotypes may be based on spectral (frequency and amplitude) analysis of gastric myoelectrical and neuromuscular function. These phenotypes include dysrhythmic (GA-RI<0.25), low-amplitude (BMI-adjusted amplitude<22 µV), high-amplitude (BMI-adjusted amplitude>70 µV), high-frequency (frequency>3.35 cpm) or low-frequency (frequency<2.65 cpm), to be described in further detail below.

Figure 10:
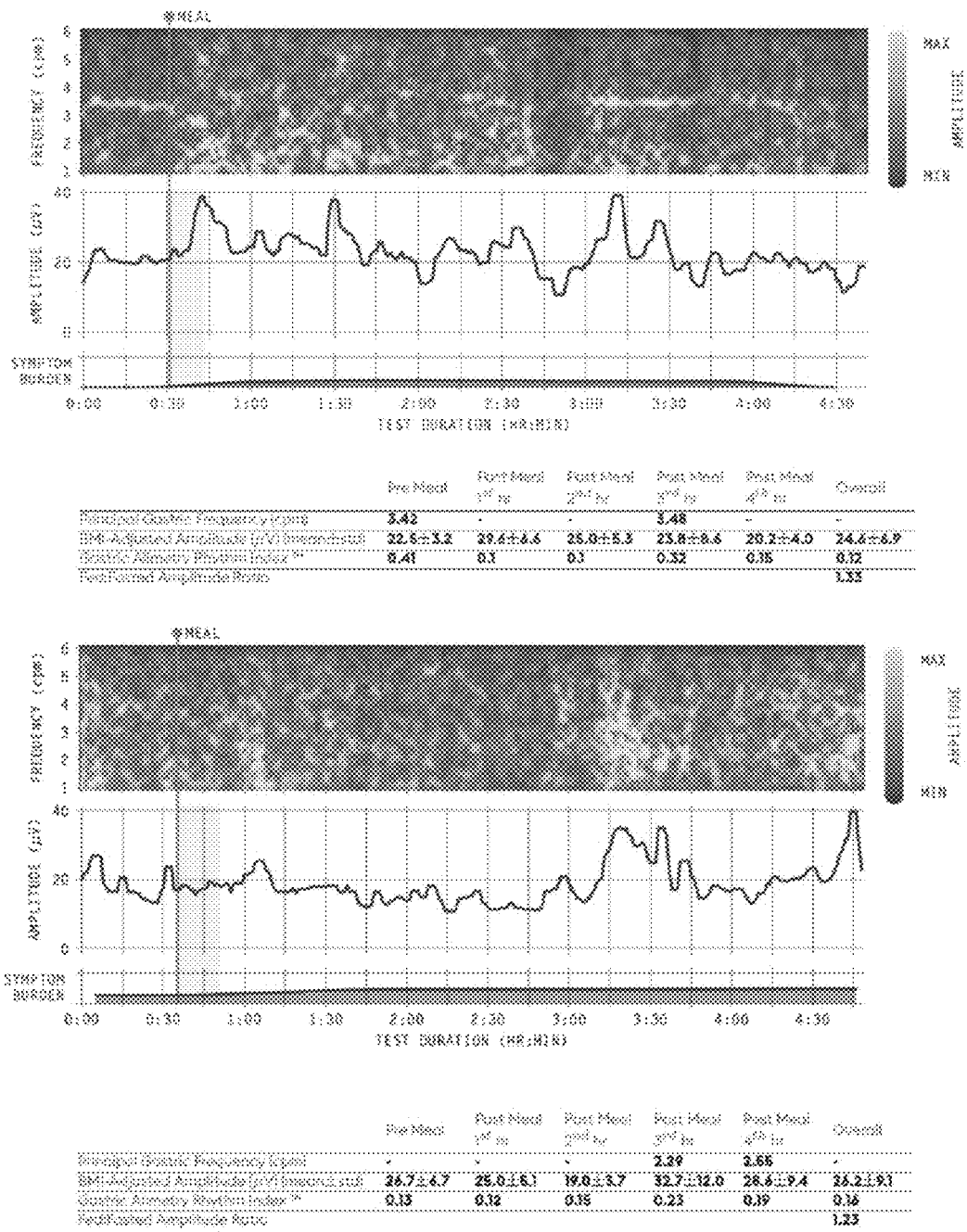
FIG. 10 is an output plot of a dysrhythmic phenotype, in accordance with various embodiments of the present invention.

FIG. 10 is an output plot of a dysrhythmic phenotype, in accordance with various embodiments of the present invention. In particular, FIG. 10 includes exemplary data from two separate patients. A dysrhythmic phenotype may be characterized by a low GA-RI (e.g., less than 0.25). The dysrhythmic phenotype may be further characterized by an absent principal gastric frequency, low BMI-adjusted amplitude, and a low fed: fasted amplitude ratio (ff-AR). Additionally, a patient having a dysrhythmic phenotype may output a variable symptom profile and/or symptoms may be meal responsive. The dysrhythmic phenotype may be indicative of neuromuscular dysfunction, which has been pathologically linked to subgroups within FD, CNVS, gastroparesis, and diabetic gastropathy. Rhythmic instabilities may reflect interstitial cell of Cajal (ICC) injury or dysfunction. Other factors that may also contribute to gastric dysrhythmias include motion sickness and drugs such as glucagon. Gastric emptying may be normal or delayed because emptying status correlates poorly with neuromuscular dysfunction. Symptom genesis may arise due to accompanying immune activation, enteric neuropathy, and hypersensitivity, with dysmotility contributing secondary symptom overlays.

Figure 11:
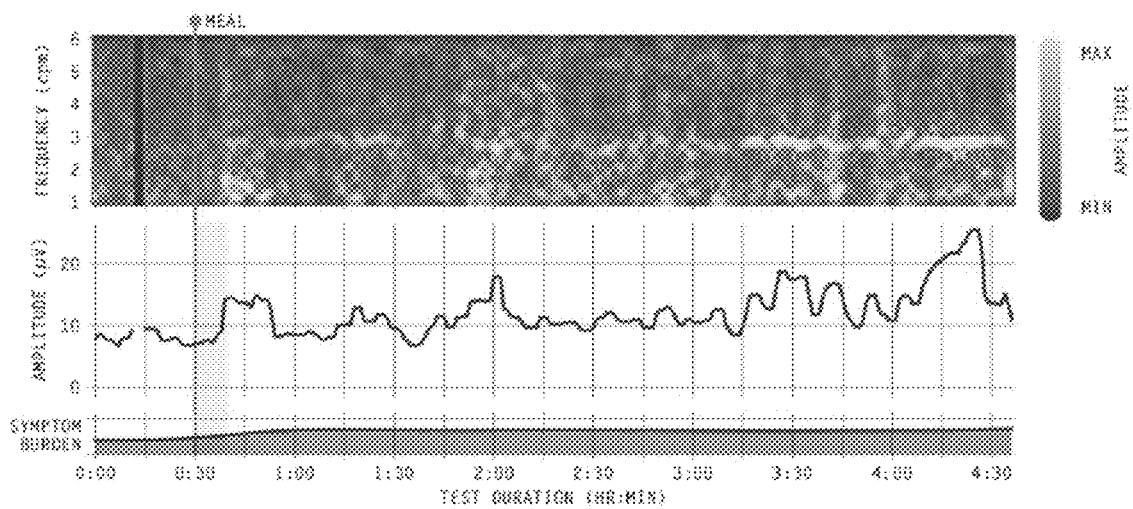
FIG. 11 is an output plot of a low amplitude phenotype, in accordance with various embodiments of the present invention.
Figure 11:
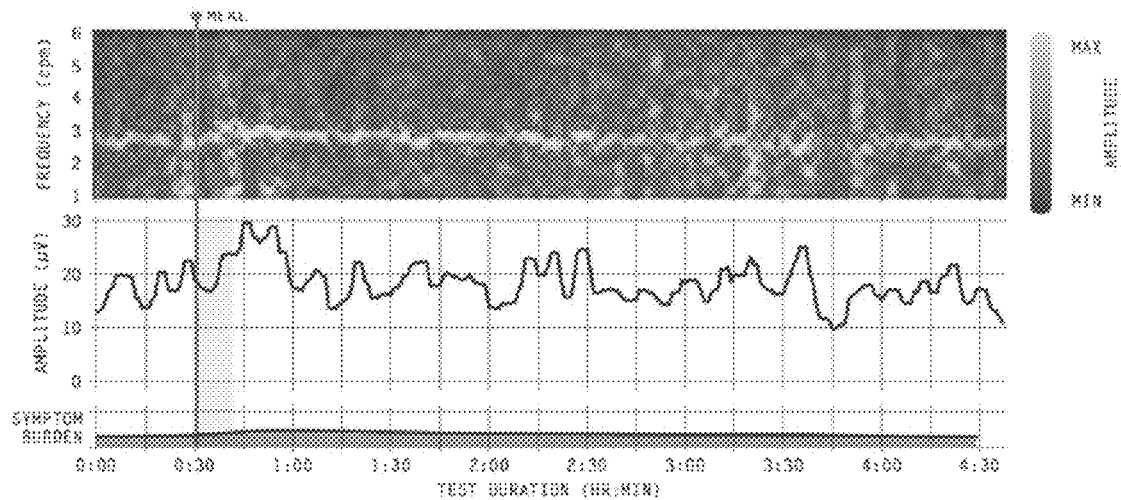

FIG. 11 is an output plot of a low amplitude phenotype, in accordance with various embodiments of the present invention. In particular, FIG. 11 includes exemplary data from two separate patients. A low amplitude phenotype may be characterized by a low BMI-adjusted amplitude (e.g., less than 22 µV) and a normal GA-RI. A low amplitude phenotype may be further characterized by a normal principal gastric frequency and/or a low ff-AR. Additionally, a patient having a low amplitude phenotype may output a variable symptom profile and/or symptoms may be meal-responsive. A low BMI-adjusted amplitude may be a type of neuromuscular abnormality, which may be associated with hypomotility. In isolation, low amplitude is anticipated in the context of a myopathy, or vagotomy, which impairs acetylcholine release and smooth muscle activation.

Figure 12:
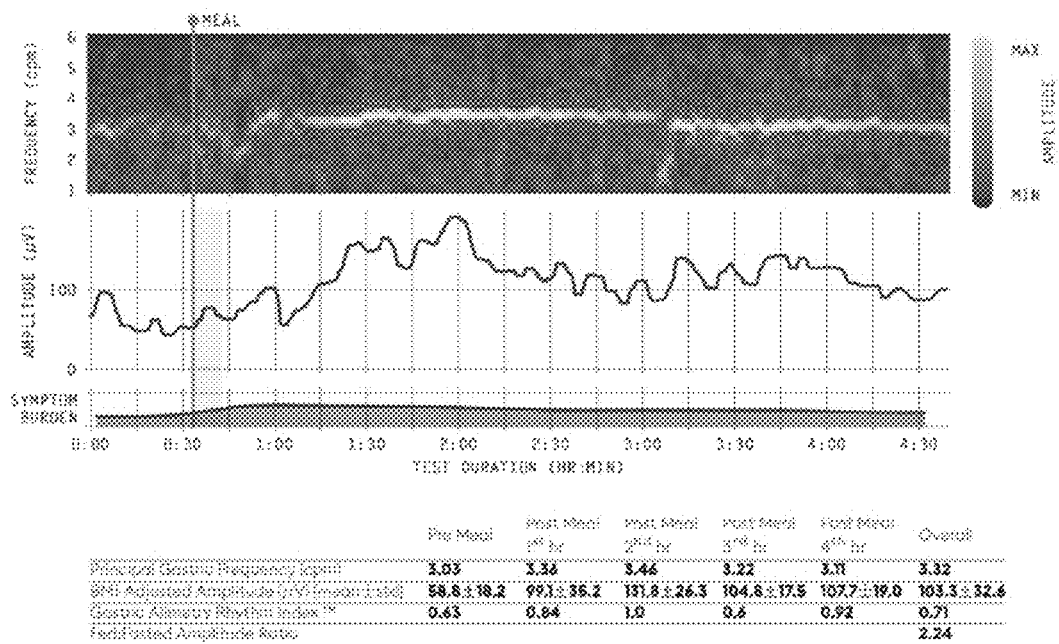
FIG. 12 is an output plot of a high amplitude phenotype, in accordance with various embodiments of the present invention.
Figure 12:
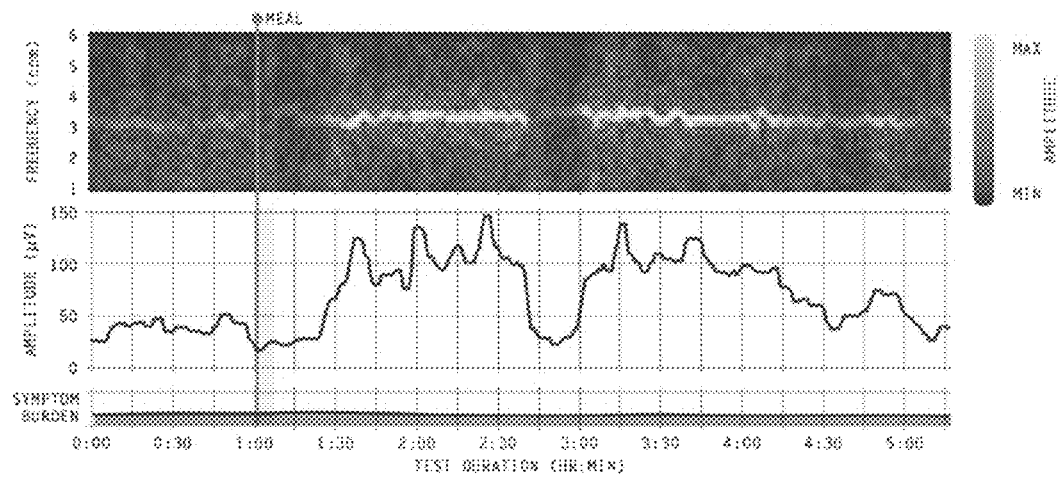

FIG. 12 is an output plot of a high amplitude phenotype, in accordance with various embodiments of the present invention. In particular, FIG. 12 includes exemplary data from two separate patients. A high amplitude phenotype may be characterized by a high sustained BMI-adjusted amplitude (e.g., greater than 70 µV). A high amplitude phenotype may be further characterized by a high-normal GA-RI. Additionally, a patient having a high amplitude phenotype may output a variable symptom profile and/or symptoms may be meal responsive. Gastric emptying may be delayed. Sustained regular or high-amplitude gastric activity has been associated with gastric outlet resistance in EGG studies, and identified in pyloric therapy responders with delayed emptying, and may indicate a relationship in some patients to outlet resistance.

Figure 13:
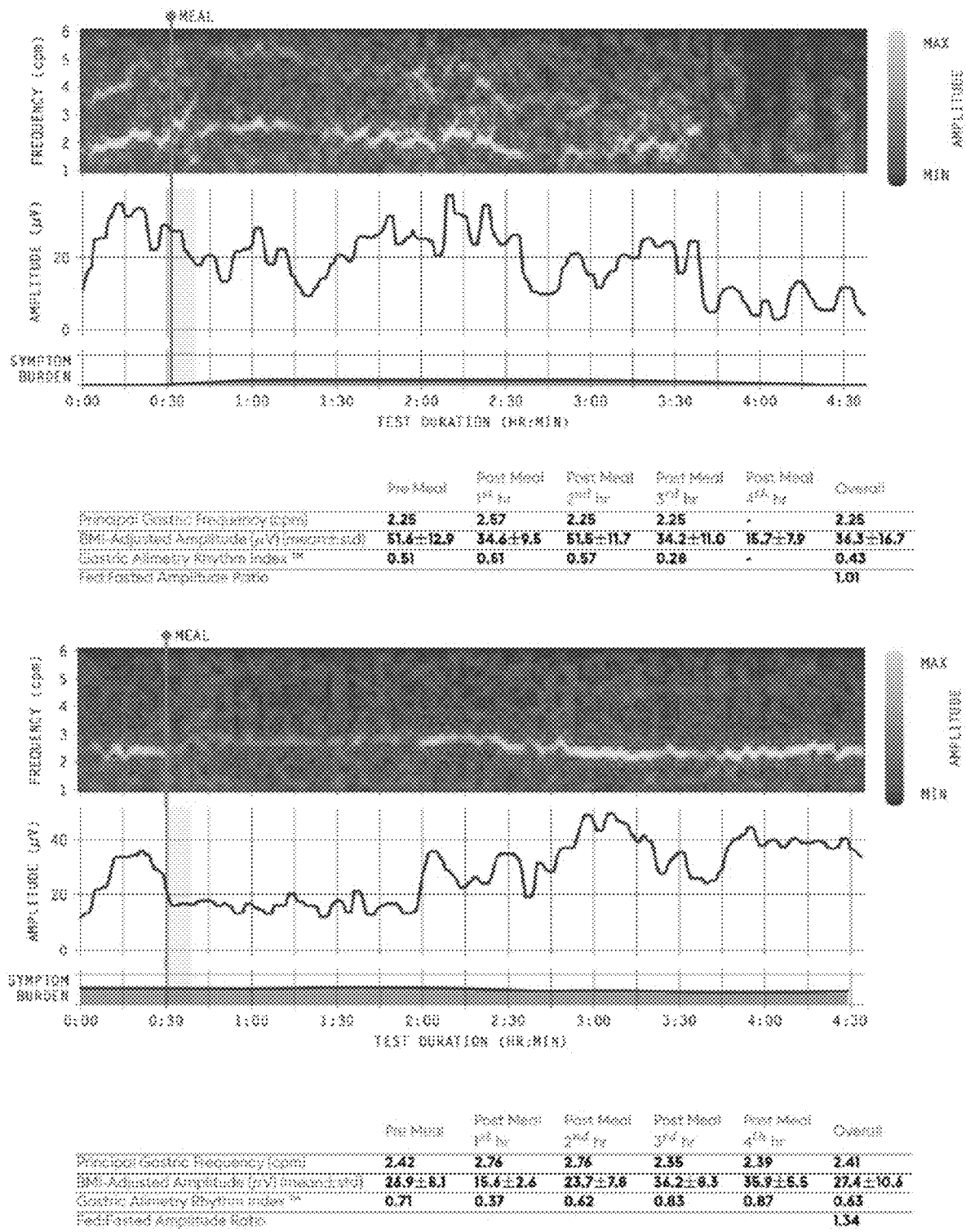
FIG. 13 is an output plot of a low frequency phenotype, in accordance with various embodiments of the present invention.

FIG. 13 is an output plot of a low frequency phenotype, in accordance with various embodiments of the present invention. In particular, FIG. 13 includes exemplary data from two separate patients. A low frequency phenotype may be characterized by low frequency activity (e.g., a principal gastric activity less than 2.65 cpm). Additionally, a patient having a low frequency phenotype may output a variable symptom profile and/or symptoms may be meal responsive. Low frequency activity can be seen in patients with primary motility disorders. The low frequency phenotype may be associated with a patient having the normal gastric pacemaker has been resected (e.g. sleeve gastrectomy or esophagectomy procedures), which may also be associated with frequency instability. In various embodiments, the low frequency phenotype is associated with a measure of temporal association less than −0.25 over the predetermined pre-prandial and post-prandial time period.

Figure 14:
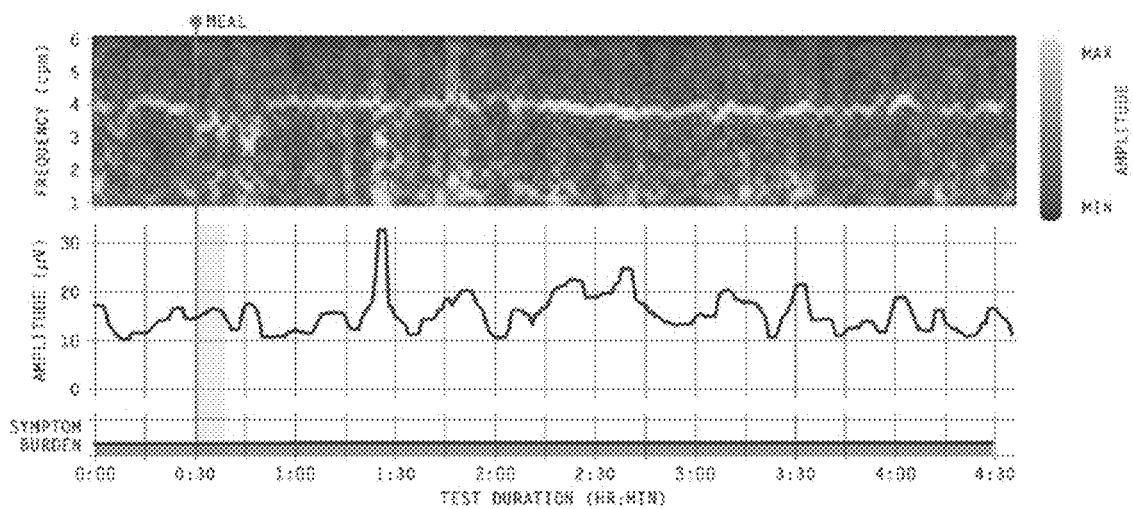
FIG. 14 is an output plot of a high frequency phenotype, in accordance with various embodiments of the present invention.
Figure 14:
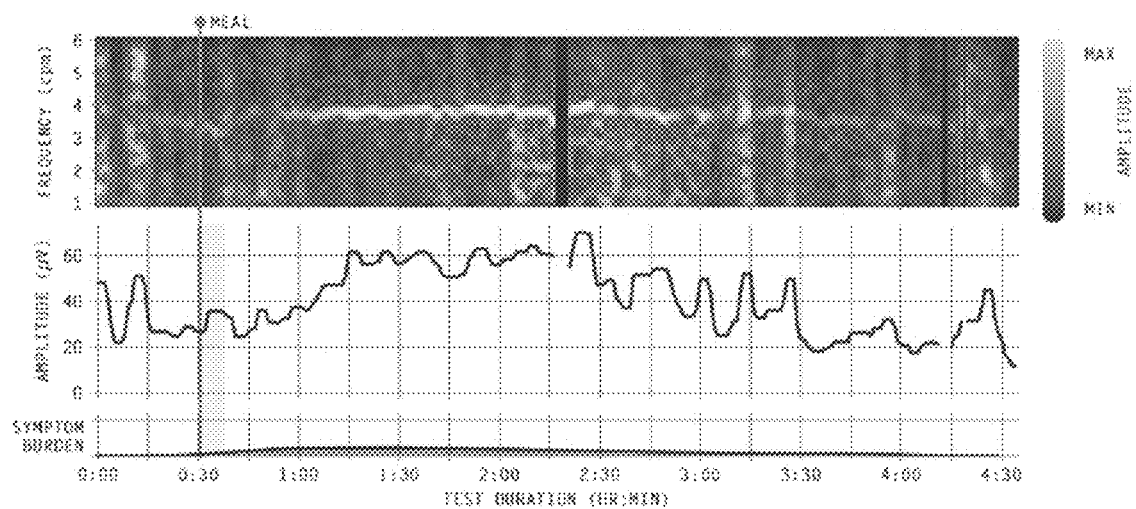

FIG. 14 is an output plot of a high frequency phenotype, in accordance with various embodiments of the present invention. In particular, FIG. 14 includes exemplary data from two separate patients. A high frequency phenotype may be characterized by elevated frequency activity (e.g., a principal gastric activity greater than 3.35 cpm). Additionally, a patient having a high frequency phenotype may output a variable symptom profile and/or symptoms may be meal responsive. High frequency activity may be associated with primary motility disorders. High frequency may be further associated with long-term diabetics in association with autonomic neuropathies and following vagal injuries. This is consistent with a known role for the vagus nerve in frequency modulation. Symptoms may be continuous when neuropathy is present; however, severe visceral neuropathy may lead to loss of GI symptom expression. In addition, patients with this phenotype may respond differently to invasive therapies such as 'GPOEM' which includes cutting the pyloric valve to drain the stomach. For example, their symptoms might not improve to the same degree as seen in other phenotypes. In various embodiments, a high frequency phenotype is associated with a measure of temporal association less than −0.25 over the predetermined pre-prandial and post-prandial time period.

Figure 15:
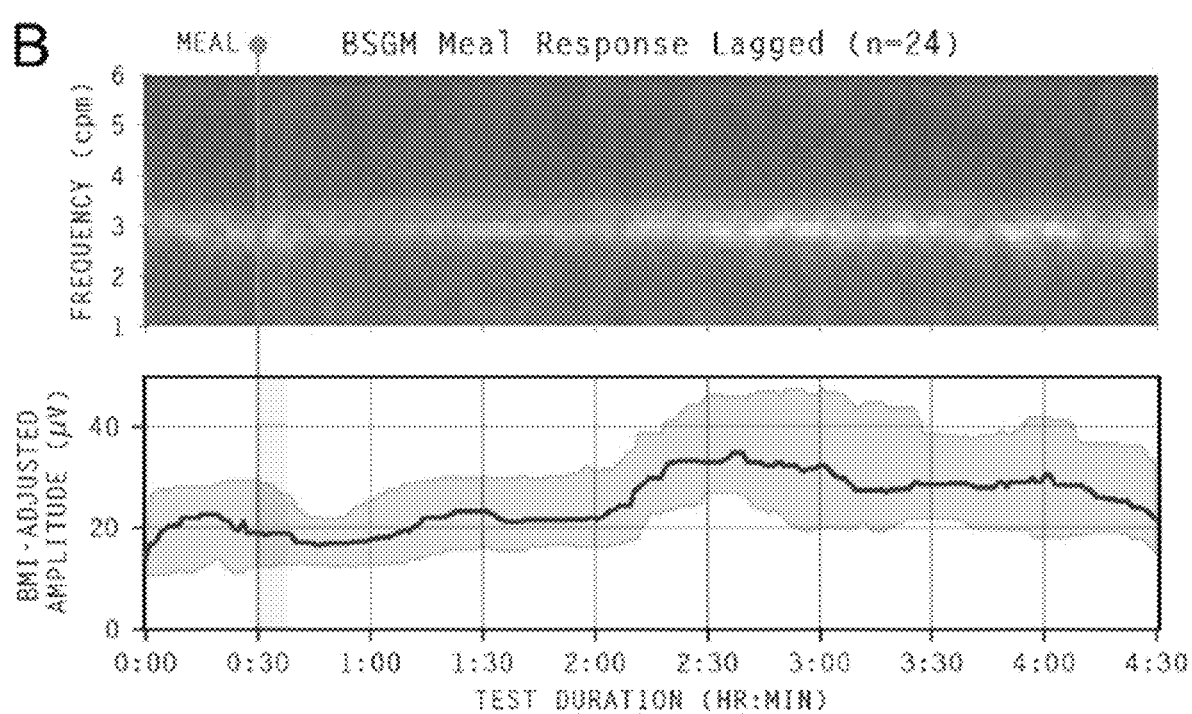
FIG. 15 is an output plot of a lagged meal response phenotype, in accordance with various embodiments of the present invention.

FIG. 15 is an output plot of a lagged meal response phenotype. An additional metric may be used to determine various phenotypes described herein. In particular, FIG. 15 is a summary plot of multiple patients with a lagged meal response phenotype combined into a single summary spectral map. A meal response ratio metric may be defined by dividing the amplitude in the first 2 hours postprandially by the last 2 hours. A normal 'meal response ratio' was empirically defined as greater than 1. Combined BSGM and gastric emptying testing provide subgrouping of patients with chronic gastroduodenal symptoms. In addition to revealing neuromuscular abnormalities, metrics as described herein define a 'delayed meal response' phenotype (e.g., interchangeably referred to herein as a "lagged meal response" phenotype). This 'delayed group' in adults have substantially slower gastric emptying rates and may be considered a new subgroup of gastroparesis. Accordingly, this phenotype may predict patients likely to have delayed emptying, such as to indicate who might benefit from an emptying test after performing various of the embodiments as described herein. Furthermore, these patients likely have an accommodation or hypomotility problem, enabling another separate personalized therapy approach. Patients associated with this phenotype are likely to respond differently to invasive therapies such as 'GPOEM' which includes cutting the pyloric valve to drain the stomach. For example, their symptoms might not improve to the same degree as seen in other phenotypes.

Figure 16A:
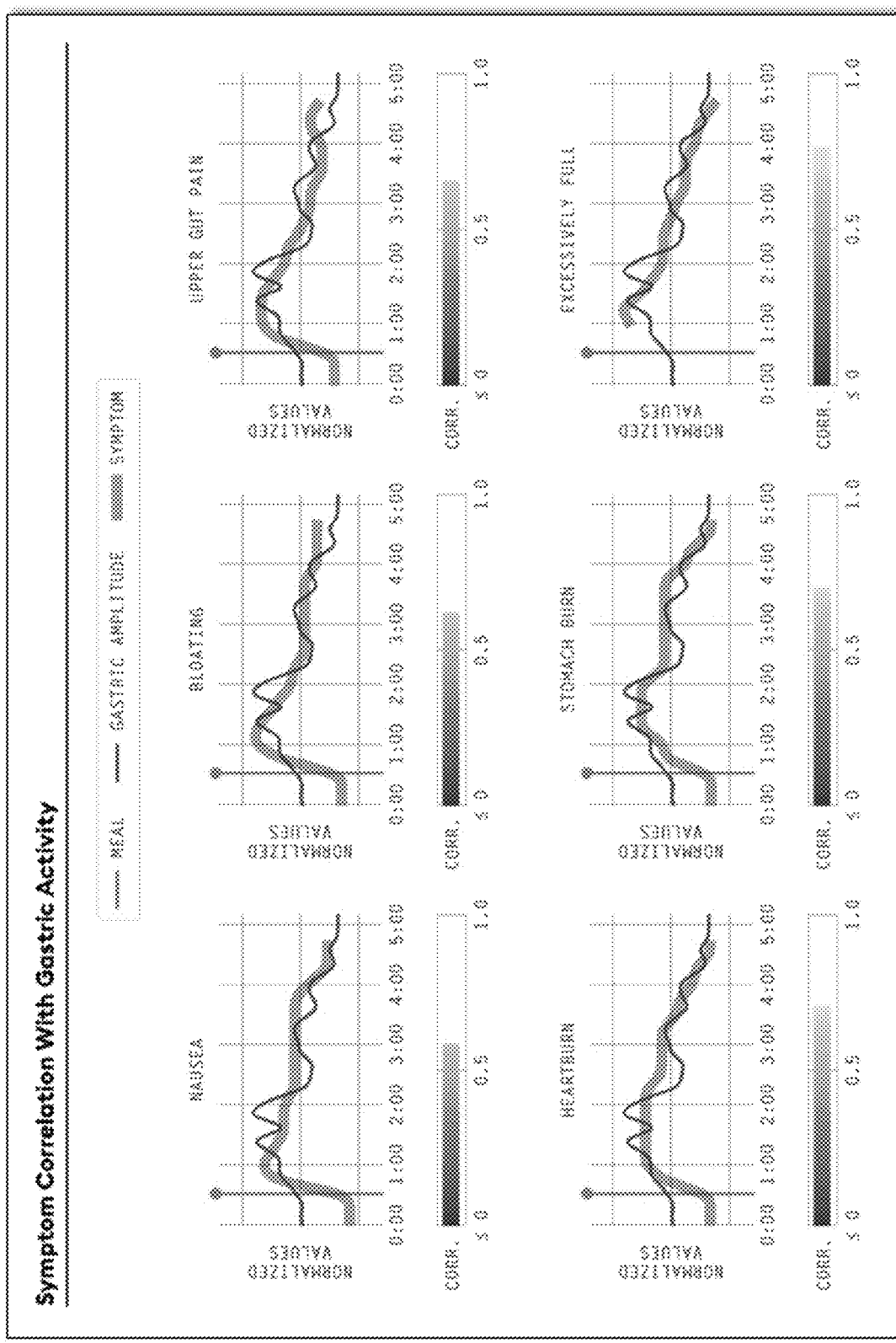
FIGS. 16A-16B are output plots of symptom correlation, in accordance with various embodiments of the present invention.
Figure 16B:
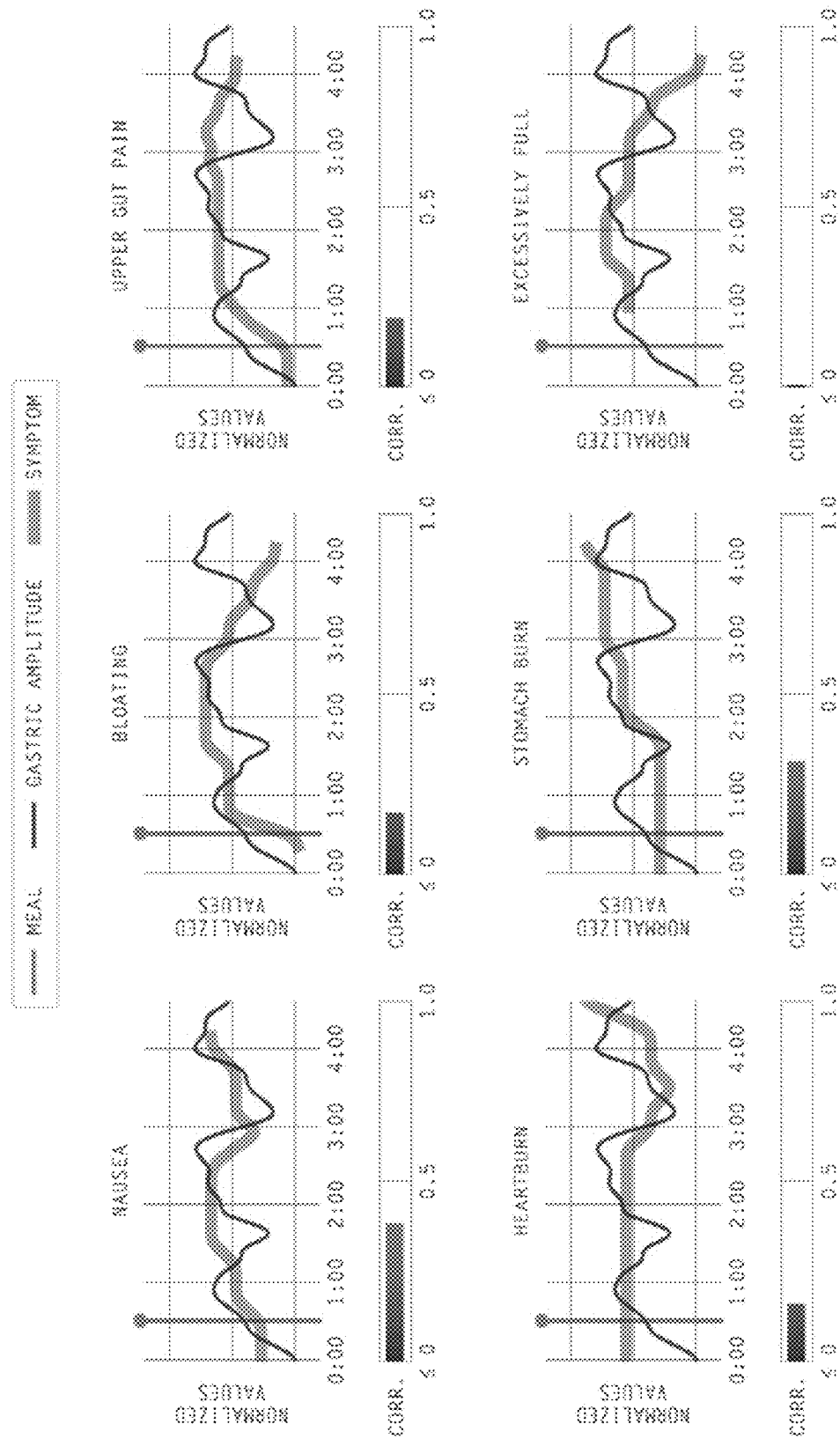

FIGS. 16A and 16B are output plots of symptom correlation. The symptom correlation plots define how symptoms correlate with gastric amplitude. In these plots, data is normalized (e.g., unitless) to visualize the association between the curves. Correlations may not be computed if the symptom does not change throughout the test. The strength of this correlation can aid in determining whether there is a sensorimotor component to symptoms (e.g., as seen in hypersensitivity disorders).

Figure 17:
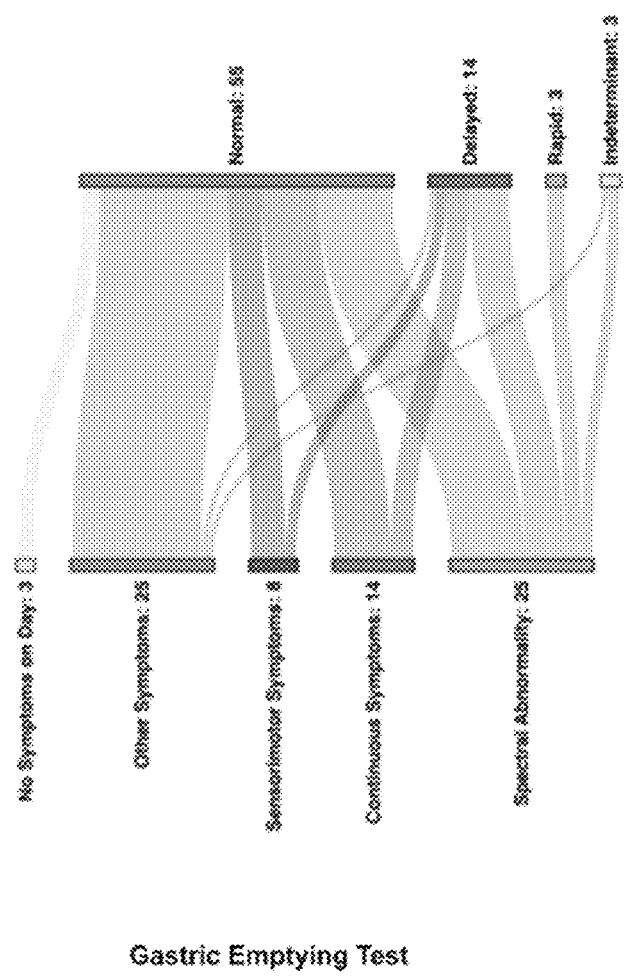
FIG. 17 includes Sankey plots of gastrointestinal phenotypes mapped to gastric emptying test results, in accordance with various embodiments of the present invention.
Figure 17:
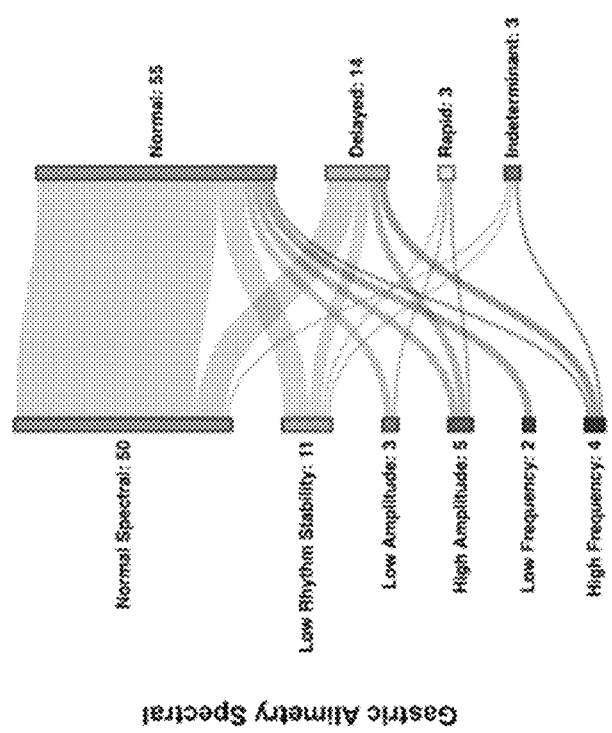

FIG. 17 includes Sankey plots of gastrointestinal phenotypes mapped to gastric emptying test results. In particular, FIG. 17 illustrates Sankey plot showing limited concordance between gastric myoelectrical abnormalities detected by embodiments of the present invention and gastric emptying testing (GET) abnormalities using conventional testing methods. Spectral analysis expanded the yield for gastric motility abnormalities vs GET alone (33.3% vs 22.7%; combined 42.7%). Accordingly, embodiments of the present invention enable further characterization of patients with normal motility through additional symptom phenotypes, specifically "sensorimotor" (where symptoms occurred simultaneously with gastric amplitude) and "continuous" (which correlates strongly with anxiety). Phenotyping as described herein correlated better with patients' chronic symptoms and anxiety levels than gastric emptying status. Including all data, embodiments of the present invention identified 2.73 more specific patient categories than GET, with limited overlap between each diagnostic modality, offering a valuable new option in the diagnostic work up of patients with chronic gastroduodenal symptoms.

Persistent upper gastroduodenal symptoms such as nausea, vomiting, bloating, and abdominal pain are prevalent in the pediatric population, impacting quality of life and leading to frequent healthcare presentations. The Rome IV pediatric criteria provide a diagnostic framework to support a positive diagnostic approach; however, overlapping symptoms and diagnostic criteria continue to pose challenges to personalized treatment. Per Rome IV, FD is subclassified into postprandial distress syndrome (PDS) and epigastric pain syndrome (EPS) which is not explicitly related to food intake. However, approximately 35% of FD patients experience both PDS and EPS. Patients with gastroparesis also commonly report epigastric pain and postprandial distress, in addition to nausea and vomiting, while demonstrating delayed gastric emptying. However, up to 25% of patients with FD also show delayed emptying, underscoring an overlapping pathophysiology. Gastric emptying as a diagnostic standard has also been challenged due to questions regarding reproducibility and symptom correlations.

Phenotyping in accordance with embodiments of the present disclosure may be expanded to pediatric applications. In particular, at least some embodiments of the following disclosure may be applied to adolescent patients (e.g., patients aged 12 to 21). Phenotypes associated with pediatric applications may include statistically different metrics and may be further differentiated by symptom severity (e.g., nausea, pain, total symptoms, etc.), functional disability scores, anxiety, and quality of life. Adolescent patients with FD and gastroparesis have overlapping clinical profiles, making individualized treatment challenging. None of these measures differed between gastroparesis and FD using conventional testing but overlap significantly according to the phenotypes described herein, indicating that gastric emptying cannot define these groups alone. Accordingly, separating patients by BSGM phenotypes identified meaningful clinical differences, with potential for personalized treatment approaches.

Various embodiments of the present invention describe phenotypes that are particularly suitable for pediatric applications. FIGS. 18-24 illustrate embodiments of pediatric gastrointestinal phenotypes which may be distinct from the adult gastrointestinal phenotypes described with respect to at least FIGS. 5-17, although some overlap may be present as described herein. For example, the pediatric phenotypes may include a high amplitude phenotype which is substantially similar or the same as the adult high amplitude phenotype described at least with respect to FIG. 12. Pediatric phenotypes may be based on analysis of similar biomarkers including GA-RI, BMI-adjusted amplitude, principle gastric frequency, fed: fasted AR, etc., though these biomarkers may have different reference values, thresholds, ranges, etc., as compared to the adult biomarkers described herein. The pediatric phenotypes, in addition to the adult phenotypes described herein, provide meaningful results (e.g., actionable biomarkers) that correlate with symptoms and inform clinical treatment and patient care.

Figure 18:
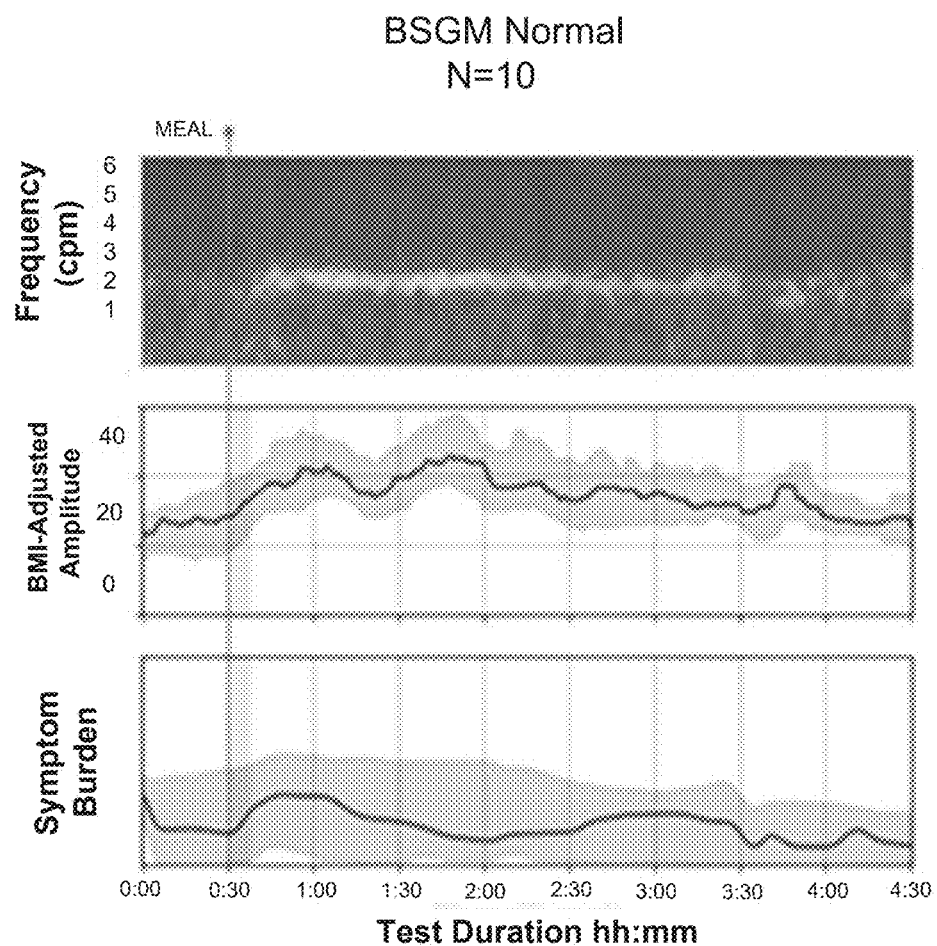
FIG. 18 is an output plot of a normal phenotype for pediatrics, in accordance with various embodiments of the present invention.

FIG. 18 is an output plot of a normal phenotype for pediatrics. In particular, FIG. 18 is a summary plot of ten patients with a normal phenotype combined into a single summary spectral map. A normal phenotype for pediatrics may include a high symptom burden that is present preprandially and continues post-prandially, being moderately meal-responsive and with no correlation between the gastric amplitude and symptom curves (Spearman's correlation r=0.11 p=0.72 (95% CI −0.53-0.68)).

Figure 19:
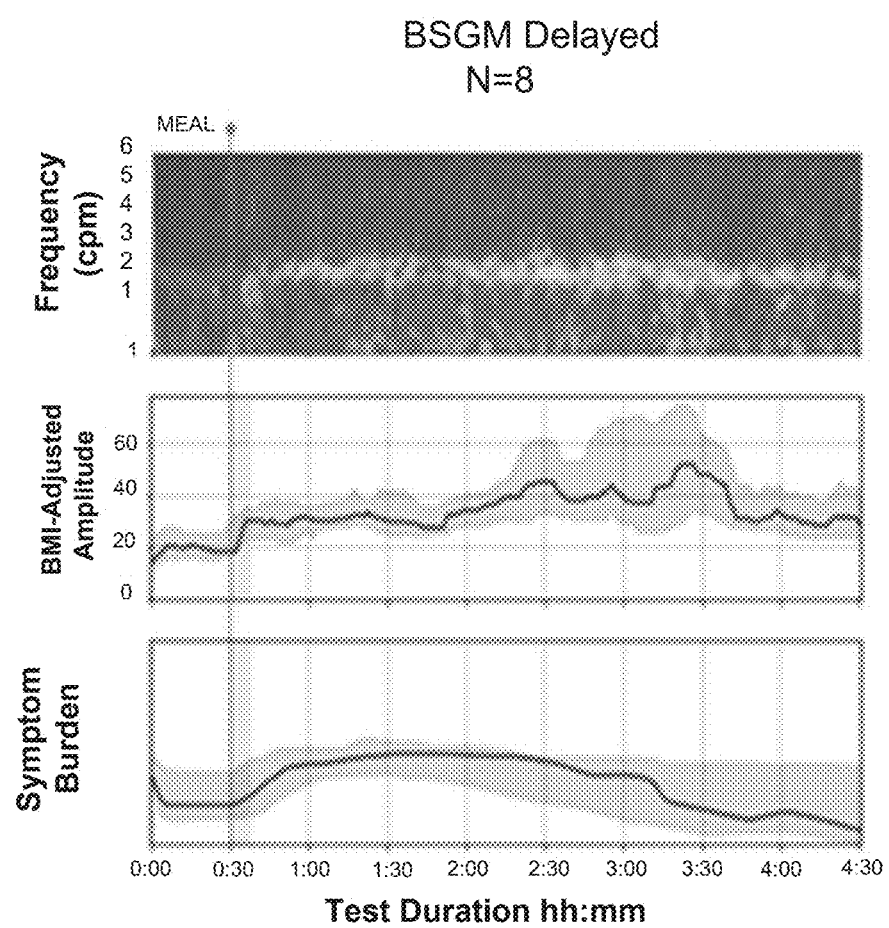
FIG. 19 is an output plot of a delayed phenotype for pediatrics, in accordance with various embodiments of the present invention.

FIG. 19 is an output plot of a delayed phenotype for pediatrics. In particular, FIG. 19 is a summary plot of eight patients with a delayed phenotype combined into a single summary spectral map. A delayed phenotype may include an increase in symptoms postprandially, which decreases as gastric amplitude increases (Spearman's correlation r=−0.26, p=0.065, 95% CI −0.18-0.54), resulting in an inverse correlation.

Figure 20:
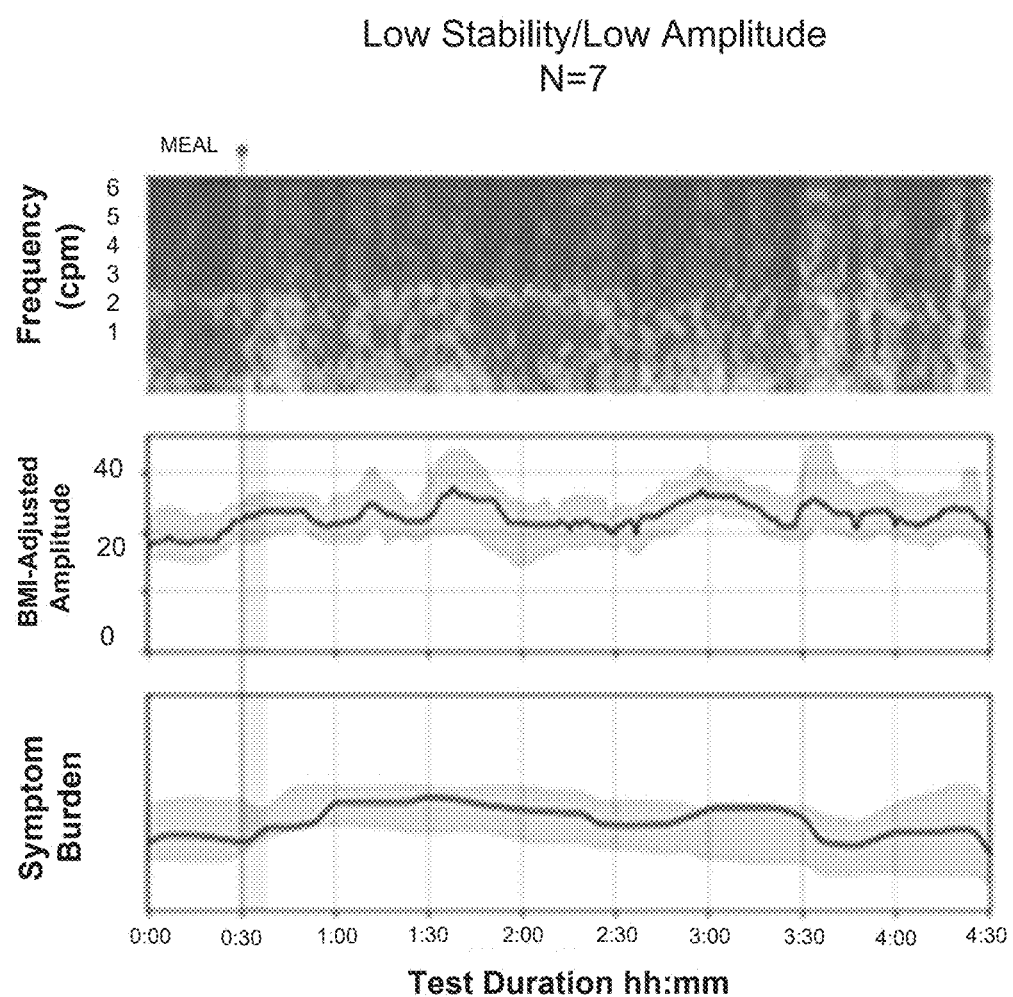
FIG. 20 is an output plot of a low stability and/or low amplitude phenotype for pediatrics, in accordance with various embodiments of the present invention.

FIG. 20 is an output plot of a low stability and/or low amplitude phenotype for pediatrics. In particular, FIG. 20 is a summary plot of seven patients with a delayed phenotype combined into a single summary spectral map. The low stability and/or low amplitude phenotype may include a relatively high symptom burden pre-prandially, which remains continuous throughout the test and with symptom curves uncorrelated with gastric amplitude (Spearman's correlation r=0.21, p=0.65 (95% CI −0.78-0.55)). Nausea and upper abdominal pain were highest in the low stability and/or low amplitude phenotype. Anxiety scores were the worst for the low stability and/or low amplitude phenotype. A similar pattern emerged with functional disability scores with the low stability and/or low amplitude phenotype reporting a higher impact on functional ability compared to the other phenotypes. This pattern was repeated for trends in abdominal pain severity index scores and quality of life scores.

Figure 21:
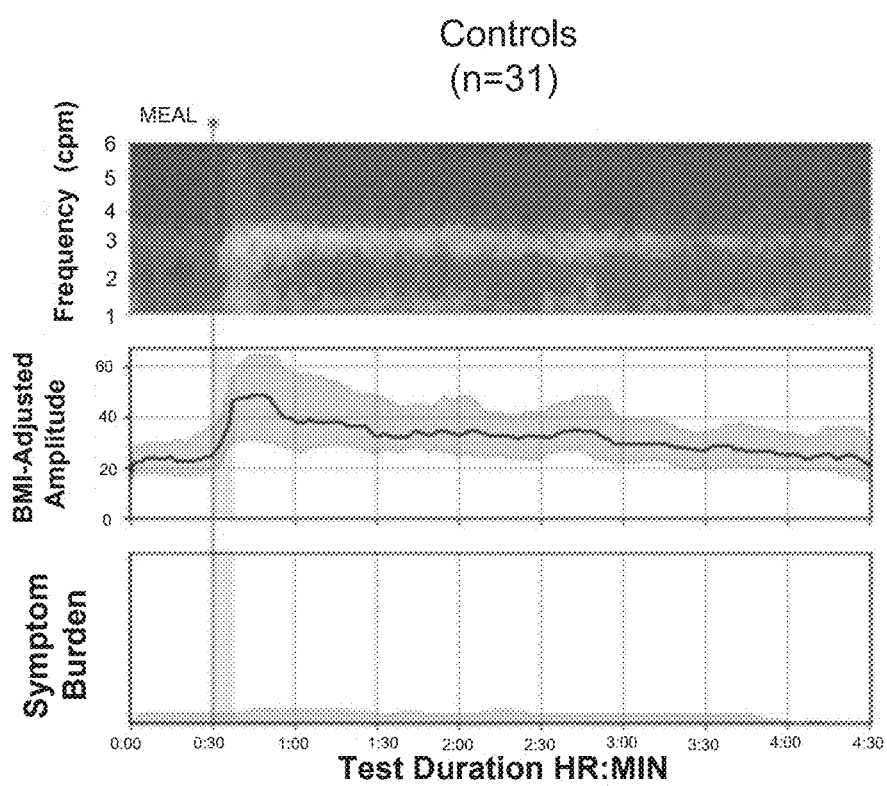
FIG. 21 is an output plot of gastric activity for a control group for pediatrics, in accordance with various embodiments of the present invention.

FIG. 21 is an output plot of gastric activity for a control group for pediatrics. In particular, FIG. 21 is a summary plot of 31 patients in the control group combined into a single summary spectral map. The reference intervals for the metrics described herein were compared to a healthy control group of adolescents aged 12-18 years to verify reference interval acceptability in adolescents. Pediatric controls showed a moderately lower average GA-RI than adults (0.35 (0.22-0.43) versus 0.50 (0.39-0.64), p<0.001); however, the spectral metrics for control subjects overall fell within the established normative reference intervals, thus, providing confidence that the spectral profiles identified in this cohort could differentiate pediatric patients into corresponding phenotypes.

Figure 22:
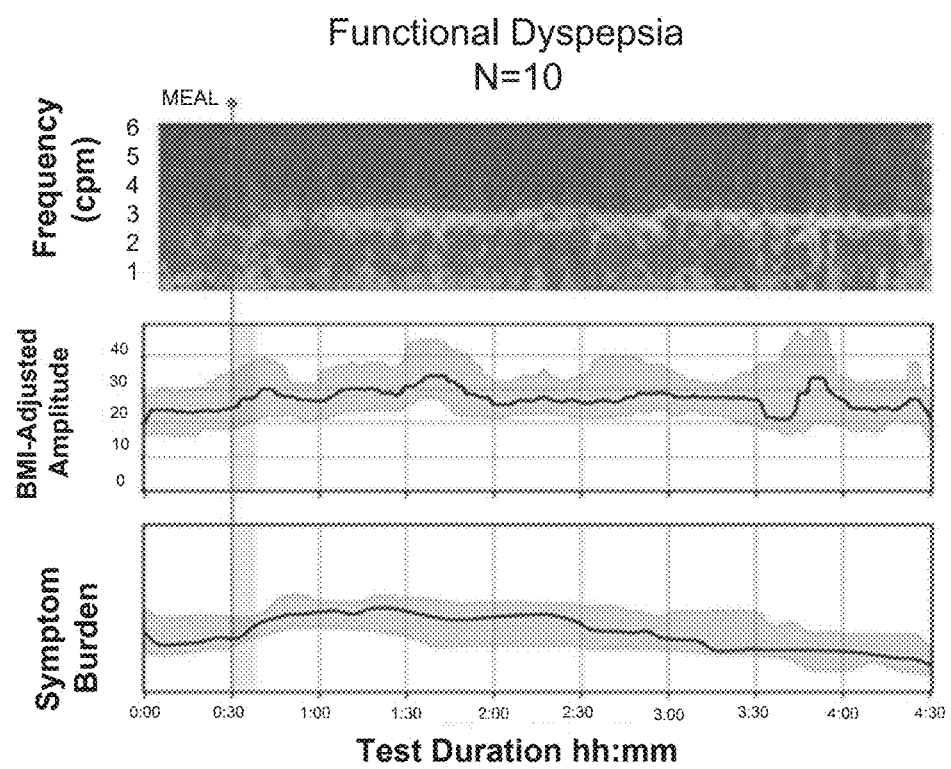
FIG. 22 is an output plot of gastric activity for a diagnosed functional dyspepsia group for pediatrics, in accordance with various embodiments of the present invention.
Figure 23:
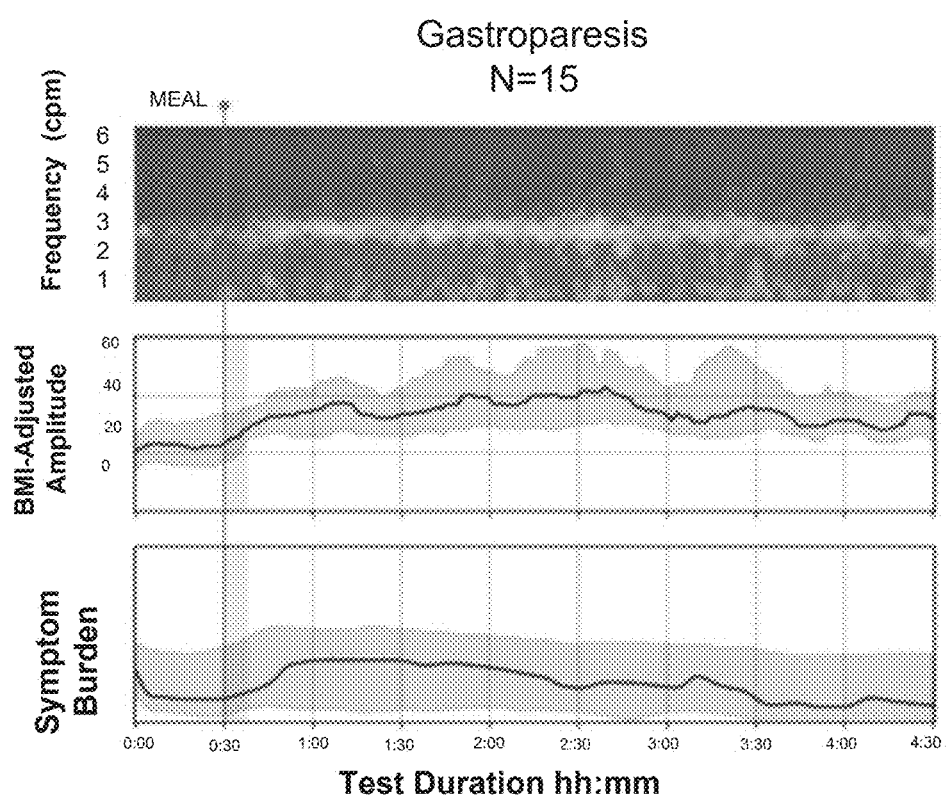
FIG. 23 is an output plot of gastric activity for a diagnosed gastroparesis group for pediatrics, in accordance with various embodiments of the present invention.

FIG. 22 is an output plot of gastric activity for a diagnosed functional dyspepsia group for pediatrics. FIG. 23 is an output plot of gastric activity for a diagnosed gastroparesis group for pediatrics, in accordance with various embodiments of the present invention. All 26 patients had documented GET results, with 15 having gastroparesis, 10 having normal GET (defined as FD; n=5 with PDS, n=5 EPS), and one patient had rapid emptying. There were no differences in TSBS between FD and gastroparesis patients (median (IQR) 27.5 (15.7-33.2) v 22.8 (5.0-39.4), p=0.95). The severity of individual symptoms also did not differ between gastroparesis, FD, or the FD sub-types, and the total symptom burden between PPD/EPS sub-types was similar (mean (SD): 26.9 (7.7) vs. 15.7 (9.2), p=0.26). Clinical symptoms, quality of life, functional disability, and mental wellbeing also showed no differences between gastroparesis and FD groups. These plots reveal no differences in BSGM spectral metrics between FD and gastroparesis patients. Spectral metrics were also similar between FD subtypes with no significant differences between PDS and EPS in terms of PGF (mean 2.84±0.17 vs 3.01±1.6; p=0.71); BMI-adjusted amplitude (27.3±6.9 vs 31.2±9.2; p=0.38); GA-RI 0.30±0.18 vs 0.38±0.28; p=0.26, or ff-AR (1.5±0.37 v 1.4±0.94; p=0.62). Gastroparesis and FD patients were therefore clinically indistinguishable across symptom severity, functional disability, psychometric profiles, and BSGM spectral metrics.

Figure 24:
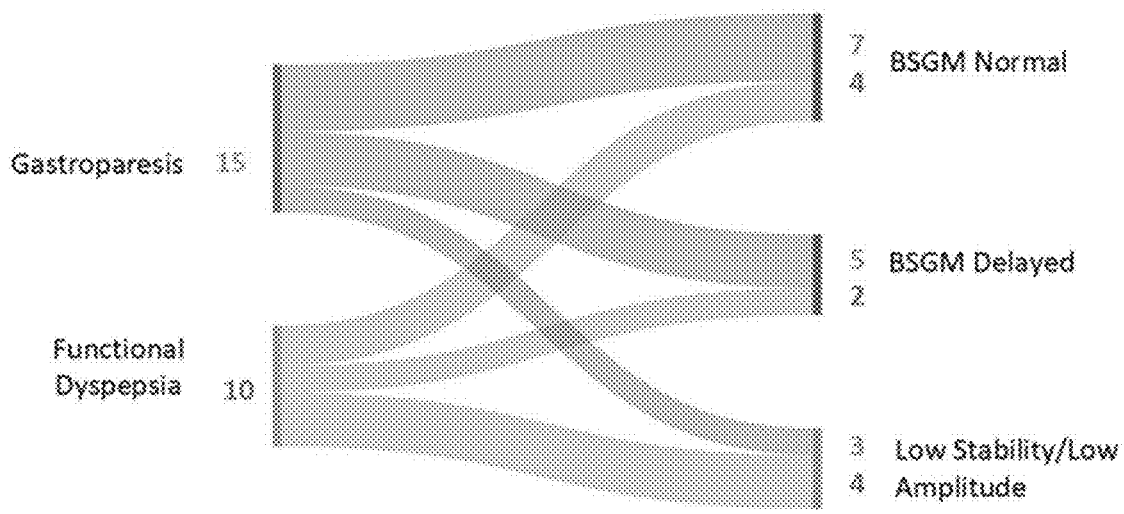
FIG. 24 is a Sankey plot of the diagnosed functional dyspepsia group and the diagnosed gastroparesis group mapped to gastrointestinal phenotypes for pediatrics, in accordance with various embodiments of the present invention.

FIG. 24 is a Sankey plot of the diagnosed functional dyspepsia group and the diagnosed gastroparesis group mapped to gastrointestinal phenotypes for pediatrics. As shown in FIG. 24, there was no relationship between the clinical diagnoses of FD, gastroparesis, and the gastrointestinal the phenotypes described herein, thereby further illustrating the overlap in diagnoses that exacerbates diagnostic and treatment complications.

Gastric emptying testing (GET) is used to differentiate FD and gastroparesis patients, yet these disorders show overlapping clinical characteristics. BSGM combines a non-invasive gastric electrophysiological mapping test with validated symptom profiling to improve patient subgroup phenotyping. Adolescent FD and gastroparesis patients defined by GET and Rome IV were indistinguishable by symptoms, quality of life and health psychology. In contrast, BSGM differentiated FD and gastroparesis patients into three distinct phenotypes with meaningful clinical differences. BSGM improves patient differentiation by identifying discrete subgroups of patients with specific dysmotility profiles, with superior symptom and biopsychosocial correlations. These subgroups have implications for diagnoses and tailoring of treatment and management decisions.

Figure 25:
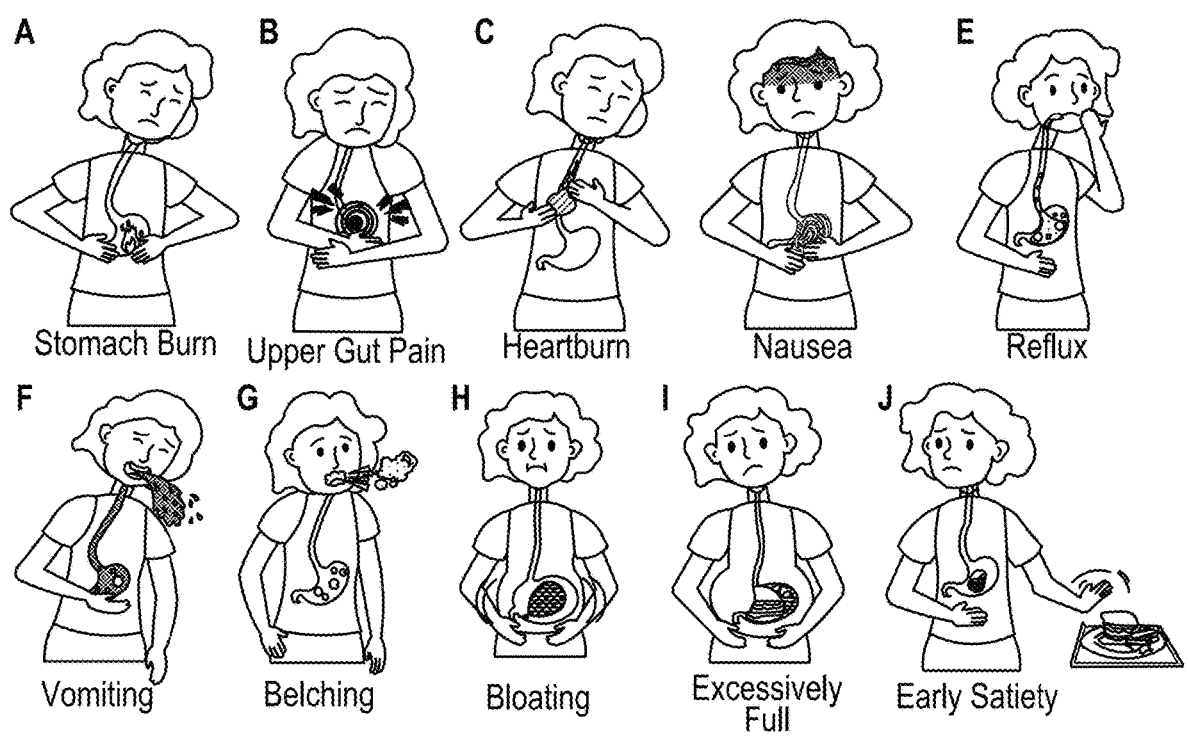
FIG. 25 illustrates exemplary pictograms for receiving patient symptom information, in accordance with various embodiments of the present invention.

Various embodiments illustrated by the following figures including FIGS. 25-29 may be applied to both adult and pediatric applications unless otherwise noted herein. For example, any of the reports and portion thereof may be provided in adult and pediatric applications without limitation. FIG. 25 illustrates exemplary pictograms for receiving patient symptom information. FIG. 25 illustrates a series of pictograms developed for pediatric usage, although the series of pictograms shown in FIG. 25 has been shown to also improve adult symptom information input. Patients often find it very difficult to describe their GI symptoms, as they overlap and can seem similar. Therefore, these exemplary pictograms enable an accurate, standardized, and reproducible symptom definition. These pictograms employ pantomime-like demonstrations of each symptom rather than just static body outlines. As illustrated in FIG. 25, reference A refers to stomach burn, reference B refers to upper gut pain, reference C refers to heartburn, reference D refers to nausea, reference E refers to reflux, reference F refers to vomiting, reference G refers to belching, reference H refers to bloating, reference I refers to excessive fullness, and reference J refers to early satiation. Symptom reporting is significantly improved particularly for symptoms such as early satiation and excessive fullness.

Figure 26:
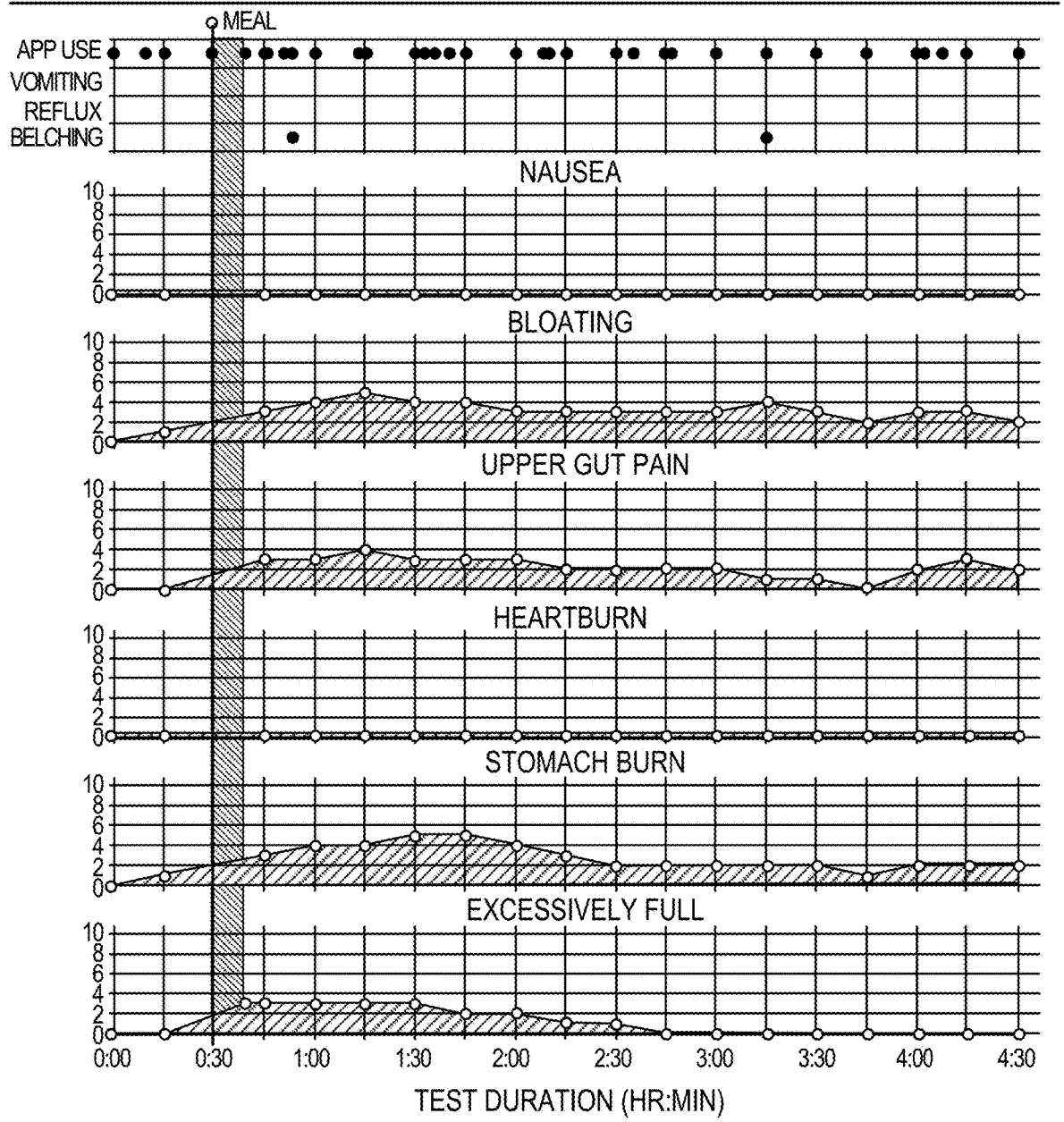
FIG. 26 illustrates an exemplary symptom graph, in accordance with various embodiments of the present invention.

FIG. 26 illustrates an exemplary symptom graph. Timing of symptoms and gastric amplitude may be positively correlated, uncorrelated, or negatively correlated according to various phenotypes described herein. When spectral analysis is abnormal, the symptom analysis provides complementary data. When the spectral analysis is normal, specific symptom phenotypes may be identifiable in over half of cases which link to gastric activity patterns. It should be noted whether symptoms are present before the meal (including type and severity), followed by an assessment of how the symptoms changed in relation to the meal. The presence of early satiation should be noted as a marker of post-prandial distress which is assessed as a single time-point symptom immediately after the meal, for example.

Meal-responsive symptoms either increase after the meal and decline over time or increase with the meal and then remain constant. A symptom curve that increases then decreases in profile is associated with gastric emptying decay curves, with symptoms abating as food transitions to the small intestine, therefore being a strong indicator that the relevant symptoms have a gastric origin. Alternatively, symptoms may remain relatively continuous throughout the test and may be associated with a higher frequency of gut-brain axis (centrally mediated) disorders and vagal neuropathy. If symptoms trend upwards late into the test, this may suggest a 'post-gastric' (small intestine) symptom origin, with symptom burden progressively increasing as a greater volume of contents progress beyond the pylorus. The timing, type, and number of symptom events (vomiting, reflux and/or belching) may be correlated with the gastric amplitude.

Figure 27:
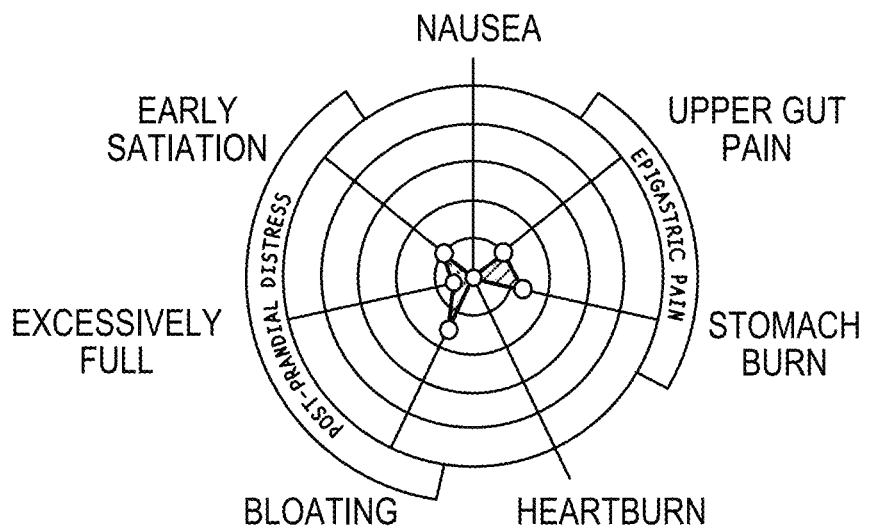
FIG. 27 illustrates exemplary symptom radar plots, in accordance with various embodiments of the present invention.
Figure 27:
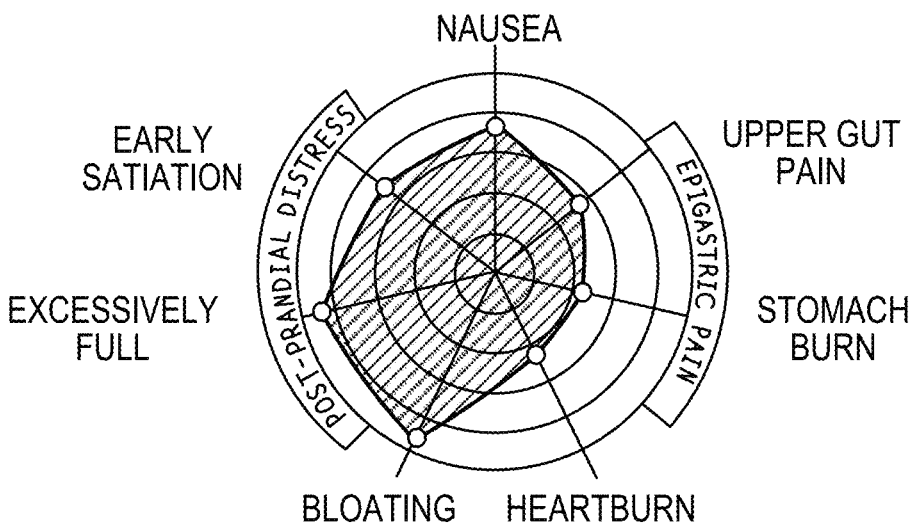

FIG. 27 illustrates exemplary symptom radar plots. Symptom radar plots may be output as part of a report, according to various embodiments. A health care professional may use such a symptom radar plot to observe if symptom severity is associated more with post-prandial distress (left axis) or epigastric pain (right axis) disorder subtypes.

Figure 28:
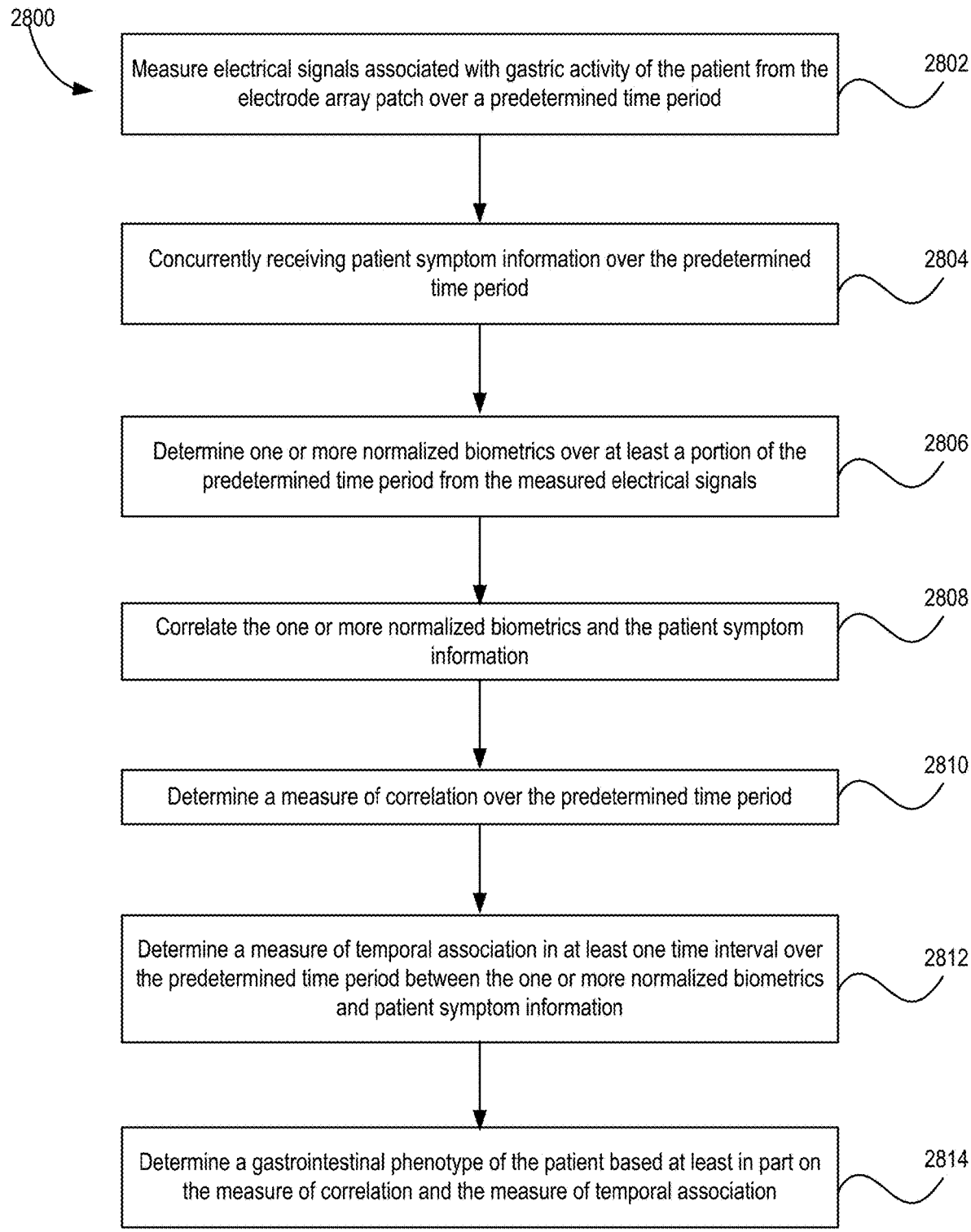
FIG. 28 is a flowchart of mapping gastric activity, in accordance with various embodiments of the present invention.

FIG. 28 is a flowchart of mapping gastric activity. Method 2800 may include any of the embodiments described herein. In various embodiments, method 2800 may include using a gastrointestinal electrode array patch as described herein. The method 2800 may be performed in combination with a standardized meal in a test environment, such as those described in detail above. Various steps of the present method may be performed in other configurations than those explicitly described herein, as would be appreciated by one having ordinary skill in the art upon reading the present disclosure.

Method 2800 may be a method for mapping gastric activity with an electrode array patch disposed over an abdomen skin surface of a patient. In various embodiments, the electrode array patch is disposed over an area of the stomach of the patient for mapping gastric activity. In other embodiments, method 2800 as described herein may be applied to other sections of the GI tract including the small bowel, the colon, etc. Method 2800 includes step 2802 measuring electrical signals associated with gastric activity of the patient from the electrode array patch over a predetermined time period. In various embodiments, the predetermined time period is between 2 hours and 6 hours, inclusive. In exemplary embodiments, the predetermined time period is 4 hours. Measuring electrical signals from the electrode array patch over the predetermined time period includes generating spatial information associated with gastric activity of the patient.

Various embodiments further include providing the patient a predetermined standardized meal prior to or during the predetermined time period. For example, the predetermined time period may include when the patient starts ingesting the predetermined standardized meal including post-prandially monitoring for a time period after the meal is at least partially consumed.

Step 2804 includes concurrently receiving patient symptom information over the predetermined time period. Patient symptom information may be received via patient input to a mobile application on a mobile device, otherwise recorded verbally or orally, etc. In various embodiments, the patient symptom information is received at predetermined intervals over the predetermined time period. In exemplary embodiments, the predetermined interval is 15 minutes. In at least some embodiments, symptoms may be received as symptoms occur. For example, symptoms may be received at predetermined intervals in addition to when the symptoms occur including discrete symptom events (e.g., episodic symptoms) such as vomiting, belching, reflux, or the like.

In various embodiments, step 2804 may further include receiving patient symptom information including psychological symptoms. For example, patient symptom information may be received for a set of psychological symptoms including depression, excessive fatigue, cognitive difficulty, or anxiety. For example, a patient may provide responses a gut-brain well-being survey. In exemplary embodiments, the well-being survey includes questions that have been validated to be associated with a patient's mental health and quality of life. For example, a Gut-Brain Wellbeing Survey asks patients to rate how often they have felt or behaved in a certain way over the last two weeks on a scale from 'None of the time' to 'All of the time.'

In an exemplary embodiment, the following ten questions are asked during the test:
1. Over the last 2 weeks, how often have you felt a reduced interest in things that usually bring you enjoyment?
2. Over the last 2 weeks, how often have you felt sad, depressed, or unhappy?
3. Over the last 2 weeks, how often have you felt tired, fatigued, or lacking in energy, for no good reason?
4. Over the last 2 weeks, how often have you found thinking, staying focused, or making decisions difficult?
5. Over the last 2 weeks, how often have you felt like you could cope with the challenges in your life?
6. Over the last 2 weeks, how often have you felt like the important things in your life were out of your control?
7. Over the last 2 weeks, how often have you felt like things were going well for you?
8. Over the last 2 weeks, how often have you felt anxious, nervous, or unable to relax?
9. Over the last 2 weeks, how often have you found it hard to stop worrying about things?

10. Over the last 2 weeks, how often have you felt scared or afraid as if something bad might happen, for no good reason?

According to at least some embodiments, patients may also add comments to further explain their survey responses or to add more information about their wellbeing. These comments may be presented exactly as written by the patient below the question answers. All wellbeing questions may be optional, and a patient may decline to answer. If this is the case, this section of the report may state that they declined to answer the survey and may provide the patient's own comments about why they chose to decline, if provided.

Method 2800 includes step 2806 including determining one or more normalized biometrics over at least a portion of the predetermined time period from the measured electrical signals. The normalized biometrics may include any of the metrics described above based on the measured electrical signals. The normalized biometrics may include at least one of a principal gastric frequency (PGF), a body mass index (BMI)-adjusted amplitude, Gastric Alimetry Rhythm Index (GA-RI), fed-fasted amplitude ratio (ff-AR), and meal response ratio.

Step 2808 includes correlating the one or more normalized biometrics and the patient symptom information. For example, the patient symptom information may form a symptom curve (such as that shown in FIG. 16) that correlates with one or more normalized biometrics. A correlation coefficient or measurement of correlation may be determined for each symptom or for one or more of the symptoms.

Step 2810 includes determining a measure of correlation over the predetermined time period. According to various embodiments, step 2810 may include determining a measure of correlation over the predetermined time period or one or more portions of the predetermined time period. For example, it may be advantageous to determine a measure of correlation during certain portions of the predetermined time period (e.g., pre-prandially, post-prandially, etc.) in addition to determining a measure of correlation over the entire predetermined time period.

Step 2812 includes determining a measure of temporal association in at least one time interval over the predetermined time period between the one or more normalized biometrics and patient symptom information. Similarly, according to various embodiments, step 2812 may include determining a measure of temporal association over the predetermined time period or one or more time intervals of the predetermined time period. For example, it may be advantageous to determine a measure of temporal association during certain portions of the predetermined time period (e.g., pre-prandially, post-prandially, etc.) in addition to determining a measure of temporal association over the entire predetermined time period.

Step 2814 includes determining a gastrointestinal phenotype of the patient based at least in part on the measure of correlation and the measure of temporal association. The gastrointestinal phenotype may include at least one of a normal Body Surface Gastric Mapping (BSGM) phenotype, a delayed onset phenotype, a low stability and/or low amplitude phenotype, or a high amplitude phenotype, as described in detail above. For example, the normal BSGM phenotype is associated with no measure of correlation and a measure of temporal association between $-0.25$ and $+0.25$ over the predetermined pre-prandial and post-prandial time period. In another example, the delayed onset phenotype is associated with a measure of temporal association less than $-0.25$ over the predetermined pre-prandial and post-prandial time period. In yet another example, the low stability and/or low amplitude phenotype is associated with no measure of correlation and a measure of temporal association between $-0.25$ and $+0.25$ over the predetermined pre-prandial and post-prandial time period.

According to various embodiments, method 2800 may include outputting a recommendation based at least in part on the phenotype associated with the patient. According to various embodiments described in detail above, phenotypes may be associated with different diseases, disorders, or the like, that may benefit from distinct types of treatment. For example, the low stability and/or low amplitude phenotype may be associated with neuromuscular disorders including at least one of gastric dysrhythmias, interstitial cell of Cajal disorders, antral hypomotility, smooth muscle disorders, or gastroparesis. The normal BSGM phenotype may be associated with a gut-brain axis disorder including irritable bowel syndrome, reflux hypersensitivity, or functional dyspepsia. For example, the normal BSGM phenotype may be associated with a gut-brain axis disorder when the symptoms are independent of (not correlated to) the gastric amplitude. This may also include the continuous and meal responsive symptom phenotypes. Functional dyspepsia may include post-prandial distress syndrome, epigastric pain syndrome, chronic nausea and vomiting syndrome, etc. The delayed onset phenotype may be associated with gastroparesis. A report may accordingly output a recommendation for treatment based at least in part on the phenotype and any associated disease, disorder, or the like. According to various embodiments of the present disclosure, visceral hypersensitivity and impaired accommodation (a type of fundic dysfunction) may be considered sensorimotor disorders. Fundic disorders may include excessive relaxation of the fundus, which may be associated with the long lag phenotype. Alternatively, the long lag phenotype may be associated with inadequate vagal drive and/or failure of timely or sufficient vagal impulses arriving at the stomach.

A report may include the recommendation and any associated data described herein. The report may include the patient symptom information including time indications of when the symptoms occurred, and any correlations associated therewith. The report may include any out the output plots shown in exemplary figures, in particular, FIGS. 17-20 and FIGS. 26-27.

Figure 29:
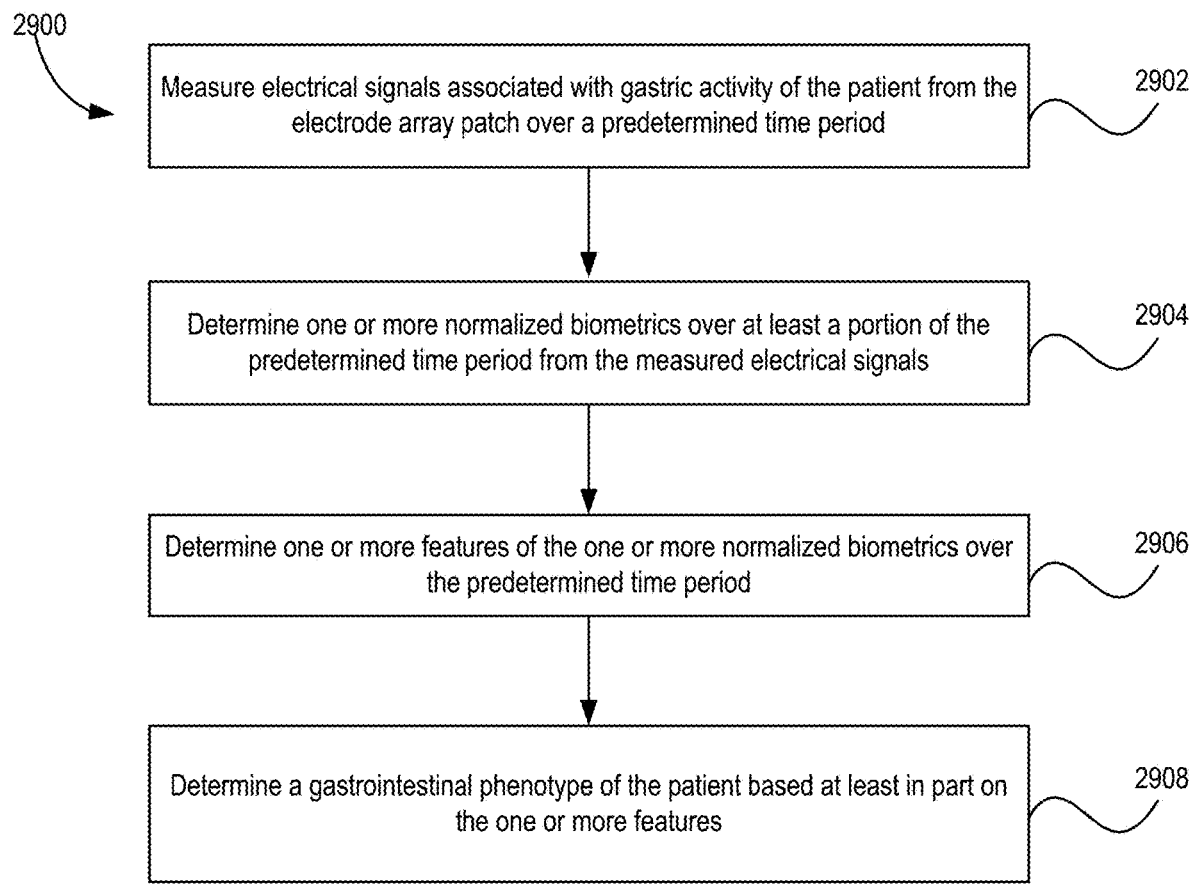
FIG. 29 is a flowchart of mapping gastric activity, in accordance with various embodiments of the present invention.

FIG. 29 is a flowchart of mapping gastric activity. According to various embodiments, at least some phenotypes may be determined based at least in part on one or more features of the one or more normalize biometrics over the predetermined time period. In various embodiments, method 2900 may include using a gastrointestinal electrode array patch as described above. The method 2900 may be performed in combination with a standardized meal in a test environment, such as those described in detail above. Various steps of the present method may be performed in other configurations than those explicitly described herein, as would be appreciated by one having ordinary skill in the art upon reading the present disclosure.

Method 2900 includes step 2902 including measuring electrical signals associated with gastric activity of the patient from the electrode array patch over a predetermined time period. Step 2902 is substantially similar to step 2802 described above with respect to method 2800 of FIG. 28 and may include any of the embodiments described with respect to step 2802. Step 2904 includes determining one or more normalized biometrics over at least a portion of the predetermined time period from the measured electrical signals. Step 2904 is substantially similar to step 2804 described above with respect to method 2800 of FIG. 28 and may include any of the embodiments described with respect to step 2804.

Method 2900 includes step 2906 including determining one or more features of the one or more normalized biometrics over the predetermined time period. One or more features may include determining that one or more normalized biometrics includes a sustained high frequency over a predetermined time period or, in contrast, a sustained low frequency over the predetermined time period. In other embodiments, one or more features may include a temporal association with the meal response. For example, a high frequency post-prandially. The one or more features may include any of the embodiments described herein that are descriptive of the phenotypes above.

Step 2908 includes determining a gastrointestinal phenotype of the patient based at least in part on the one or more features. The gastrointestinal phenotype may include at least one of a sensorimotor phenotype, a neuromuscular phenotype, a post-gastric phenotype, an activity-alleviated phenotype, and a continuous phenotype. Method 2900 may include outputting a recommendation based on the determined phenotype according to any of the embodiments described in detail above.

Gastroparesis is a heterogeneous disorder with several contributing pathophysiologies. According to various embodiments, simultaneous body surface gastric mapping (BSGM) and gastric emptying breath testing (GEBT) may be used to subgroup patients with gastroparesis based on dynamic spectral meal response profiles and emptying rate. Gastroparesis is defined on the basis of delayed gastric emptying in the absence of mechanical obstruction, with characteristic symptoms of nausea, vomiting, postprandial fullness, early satiety. Up to 1.8% of the population have symptoms characteristic of gastroparesis although fewer than 0.2% are diagnosed with confirmatory transit testing. Defining and managing gastroparesis remains challenging owing to labile gastric emptying results, poor correlations with symptoms, and overlap with functional dyspepsia and chronic nausea and vomiting syndromes.

Gastric emptying breath testing (GEBT) is an alternative to scintigraphic assessment that avoids radiation exposure and has the capacity to be done outside of specialist centers. Body surface gastric mapping (BSGM) using the Gastric Alimetry® system (Alimetry, New Zealand) is a non-invasive test of gastric function that offers a multimodal assessment of gastric function, incorporating high-resolution electrophysiology together with symptom profiles and offering complementary information to dynamic profiles determined using transit testing.

The clinical utility of confirming the degree of gastric emptying delay in gastroparesis is controversial, and defining more specific underlying mechanisms for delayed transit through BSGM has been proposed to enhance diagnostic clarity. A multimodal assessment involving an expanded set of physiological biomarkers from both tests may could therefore be advantageous in order to better target care towards specific disease mechanisms, while also enabling more specificity in clinical trial enrollment.

Patients with chronic gastroduodenal symptoms and negative gastroscopy underwent simultaneous BSGM and GEBT with 30 minutes fasting and 4 hours postprandial recording. In addition to standard metrics, the BSGM 'Meal Response Ratio' (MRR) divides the amplitude in the first 2 hours postprandially by the subsequent 2 hours (lagged meal response defined as ≤1). 143 patients underwent simultaneous BSGM and GEBT (79% female, median age 31 years, median BMI 23 kg/m$^2$). Delayed emptying occurred in 25.2% (n=36). Those with a lagged meal response had longer $T_{1/2}$ (median 98.5 [IQR 59-373] vs median 78.5 [IQR 31-288], p<0.001) and higher rates of delayed emptying (43.2% vs 17.2% p=0.006). BSGM phenotypes identified in patients with delayed emptying were: lagged meal response (25%), low gastric amplitude/rhythm stability (30.6%), elevated gastric frequencies (11.1%), and normal BSGM spectral analysis (33.3%). $T_{1/2}$ weakly correlated with worse total symptom burden score (r=0.18, p=0.03).

Solid gastric emptying was measured using a 4-hour C octanoic acid emptying breath test. All subjects were fasted overnight for at least 8 hours ahead of GEBT. Patients were asked to stop medications affecting gastric emptying, such as opioids, prokinetics, anticholinergics, and/or calcium channel blockers at least two days ahead of the GEBT. The test meals used for.

GEBT was either a pancake with 180 ml of water (11.2 g fat, 31.7 g carbohydrate, 8.4 g protein; 261 kcal total) or an egg with two slices of white toast and 180 ml of water (9.4 g fat, 34 g carbohydrate, 11.5 g protein; 268 kcal total). Breath samples were taken before starting the test meal and at 15 min intervals for 4 h. The gastric half emptying time ($T_{1/2}$) was calculated as previously described. Delayed gastric emptying was defined as $T_{1/2}$>109 min for solids.

BSGM was performed using the Gastric Alimetry system, which includes a high-resolution stretchable electrode array (8×8 electrodes; 20 mm inter-electrode spacing; 196 cm$^2$), a wearable Reader, an iPadOS App and concurrent validated symptom logging during the test. Array placement was preceded by shaving if necessary, and skin preparation (NuPrep; Weaver & Co, CO, USA). Recordings were performed simultaneously with GEBT encompassing 30 min fasting baseline, 10 min meal, and 4 h postprandial recording. Participants are asked to sit reclined in a chair and were asked to limit movement, talking, and sleeping, but were able to read, watch media, work on a mobile device, and mobilize for comfort breaks, although some movement was accepted to deliver breath samples at 15 min intervals in this protocol. Symptom capture included early satiation after meal completion, and symptoms of nausea, bloating, upper gut pain, heartburn, stomach burn, and excessive fullness were measured during continuously testing at 15-minute intervals using 0-10 visual analog scales (0 indicating no symptoms; 10 indicating the worst imaginable extent of symptoms) and combined to form a 'Total Symptom Burden Score'.

Standardized metrics were analyzed for both tests. GEBT was assessed using $T_{1/2}$ emptying time, with delay considered $T_{1/2}$>109 min. BSGM spectral analysis included Principal Gastric Frequency (PGF; reference intervals: 2.65-3.35 cycles per minute), BMI-adjusted amplitude (reference intervals: 22-70 µV), and Gastric Alimetry Rhythm Index (GA-RI; reference intervals: ≥0.25) for BSGM. In addition, a novel BSGM metric was introduced for this study called 'Meal Response Ratio' (MRR) to assess meal response timing, calculated as the ratio of the average amplitude in the first 2 hours postprandially to that of the last 2 hours. MRR was not calculated if postprandial recording duration was <4 h. A normal MRR was empirically defined as >1 based on previous studies, meaning that the dominant gastric motor response occurred within the first two hours after a meal.

An alternative method for determining the meal response timing involves identifying the continuous window of time in which the average amplitude of gastric motor response is maximized. This window of time could either be set to a fixed length, between 15 minutes to 2 hours, or dynamically adjusted to maximize the average amplitude over a subset of possible window lengths within this range. By focusing on the period with the highest sustained amplitude, this method aims to capture the peak meal response in a more targeted and flexible manner, complementing the Meal Response Ratio (MRR) by allowing for different window sizes or a more dynamic approach to identifying the meal response window.

This metric could also be paired with a measure of 'meal response prominence,' which is calculated by comparing the amplitude during the identified meal response period to the average amplitude of the remainder of the test. This prominence metric serves to quantify the relative significance of the meal response, helping to assess whether a prominent, discernible response to the meal stimulus is present. When used together, the meal response timing metric and the meal response prominence metric offer a more comprehensive assessment of both the presence and the magnitude of the meal response, thus aiding in distinguishing between normal and abnormal gastric activity.

All analyses were performed in Python v3.9.7 and R v.4.0.3 (R Foundation for Statistical Computing, Vienna, Austria). Numerical data were summarized as mean (standard deviation) or median (interquartile range) based on visual and statistical evaluation for normality, with appropriate tests for parametric or non-parametric data performed. Categorical data were cross-tabulated, and differences tested using $\chi 2$ or Fisher's exact tests. Bonferroni corrections were applied for post-hoc corrections.

Overall, 151 consecutive subjects (118, [78.1%] females, median age 31 [range 18-80] years, BMI median 22 [18.5-35] kg/m2) were enrolled and underwent simultaneous BSGM and GEBT. Complete data was available for 143 subjects after excluding 8 (5%) participants due to inadequate test quality. The large majority of patients (87%) successfully completed 100% of the test meal (mean 96±14% meal completion).

Overall (n=143), the median $T_{1/2}$ was 85 minutes (IQR 31-373), with 25.2% (n=36/143) classified as having delayed gastric emptying on GEBT. On BSGM testing, 28 (19.6%) had a low GA-RI, 23 (16.1%) had a low BMI-adjusted amplitude, 1 (0.7%) had a low Principal Gastric Frequency, and 12 (8.4%) had a high Principal Gastric Frequency. The MRR metric was applied to those with normal spectrograms (n=90); median MRR was 1.21 (IQR 0.58-4.21) with 20 (22.2%) participants classified as having a lagged meal response (i.e. greater gastric amplitude across the latter 2 hours of testing vs first 2 hours of the postprandial period).

Symptom comparisons across the whole cohort showed no differences in any symptoms between BSGM phenotypes (all comparisons p>0.05). Participants with delayed gastric emptying had worse symptoms (p=0.003), with significant differences observed for nausea, upper gut pain, excessive fullness, and early satiety. However, correlations between delayed transit and 'Total Symptom Burden Score' were weak (r=0.18, p=0.03). Patients with delayed emptying and normal BSGM had higher early satiety scores (p=0.01). There were no other differences in symptom severity between those with delayed and normal emptying across phenotypes (all comparisons p>0.05).

This study aimed to define specific gastroparesis subgroups on the basis of simultaneous BSGM and GEBT testing. Various embodiments provide a 'meal response ratio' (MRR) metric to quantify the dynamic post-prandial motor function of the stomach, and found a lagged meal response (MRR≤1) was correlated with delayed emptying.

Using BSGM metrics of gastric function, four specific subgroups of gastroparesis were identified: firstly, a normal spectrogram group with appropriately timed postprandial gastric motor activity (33%); secondly, a lagged meal response with a delayed onset to gastric motor activity (25%); thirdly, an unstable spectrogram group with low rhythm stability (30%); finally, an elevated gastric frequency group (11%). Whereas symptoms alone fail to separate mechanistic groups, the addition of BSGM testing allowed mechanistic phenotyping with potential to facilitate targeted disease management.

Gastric emptying scintigraphy testing alters clinical management in <50% of cases, and clinicians are often required to make treatment decisions based on symptoms alone. It is well established that symptoms alone poorly differentiate chronic gastroduodenal disorders, owing to significant overlap between diagnostic categories and multiple disease mechanisms contributing to individual symptoms. Given that symptoms and transit testing have pitfalls and are limited in informing management in gastroparesis, more specific tests of gastric function characterizing underlying pathophysiology are desirable.

Gastric transit is a higher order function that can result from several possible derangements of gastric function. Antral hypomotility may arise secondary to discoordinated motor activity and/or damage to ICC networks, as has been shown in patients with gastroparesis with dysrhythmic myoelectrical activity. In addition, autonomic dysfunction has been separately implicated in impaired accommodation and delayed emptying. Reduced accommodation may be evidenced by low intragastric meal distribution (i.e, antral retention), which has been correlated with symptom burden in gastroparesis. Decreased gastric tone may additionally result in inadequate gastroduodenal pressure gradients to facilitate transit. Alternatively, excessive accommodation in response to a meal could also result in delayed emptying through fundic retention. Finally, pylorospasm, or increased pyloric tone, could also be contributory as suggested by favorable results of endoscopic pyloromyotomy in patients with refractory gastroparesis.

The phenotypes identified with the aid of BSGM in this study likely relate to the various underlying gastroparesis pathophysiologies discussed above. This includes characterization of those patients with a neuromuscular phenotype through a low GA-RI, and those with vagal neuropathies through an elevated PGF. Additionally, a MRR≤1 implies a relative delay to onset of gastric activity of more than 2 h, which may indicate a disorder of postprandial accommodation accompanied by a delayed onset of antral activity. This pattern frequently results in symptoms correlating to the lagged meal response period, with symptoms then improving following the onset of gastric activity. Alternatively, when MRR is >1 but transit is delayed, this suggests an intact neuromuscular apparatus likely generating effective antral contractions, plausibly implicating antropyloric discoordination or a functional pyloric obstruction, which has previously been shown in the electrogastrography literature in association with sustained myoelectrical amplitudes.

Combined BSGM and gastric emptying testing defines subgroups of gastroparesis based on contributing disease mechanisms, including a novel group with delayed postprandial onset of gastric motor activity. Improved patient phenotyping in gastroparesis may enable improved therapeutic targeting through these biomarkers of disease processes.

Figure 30:
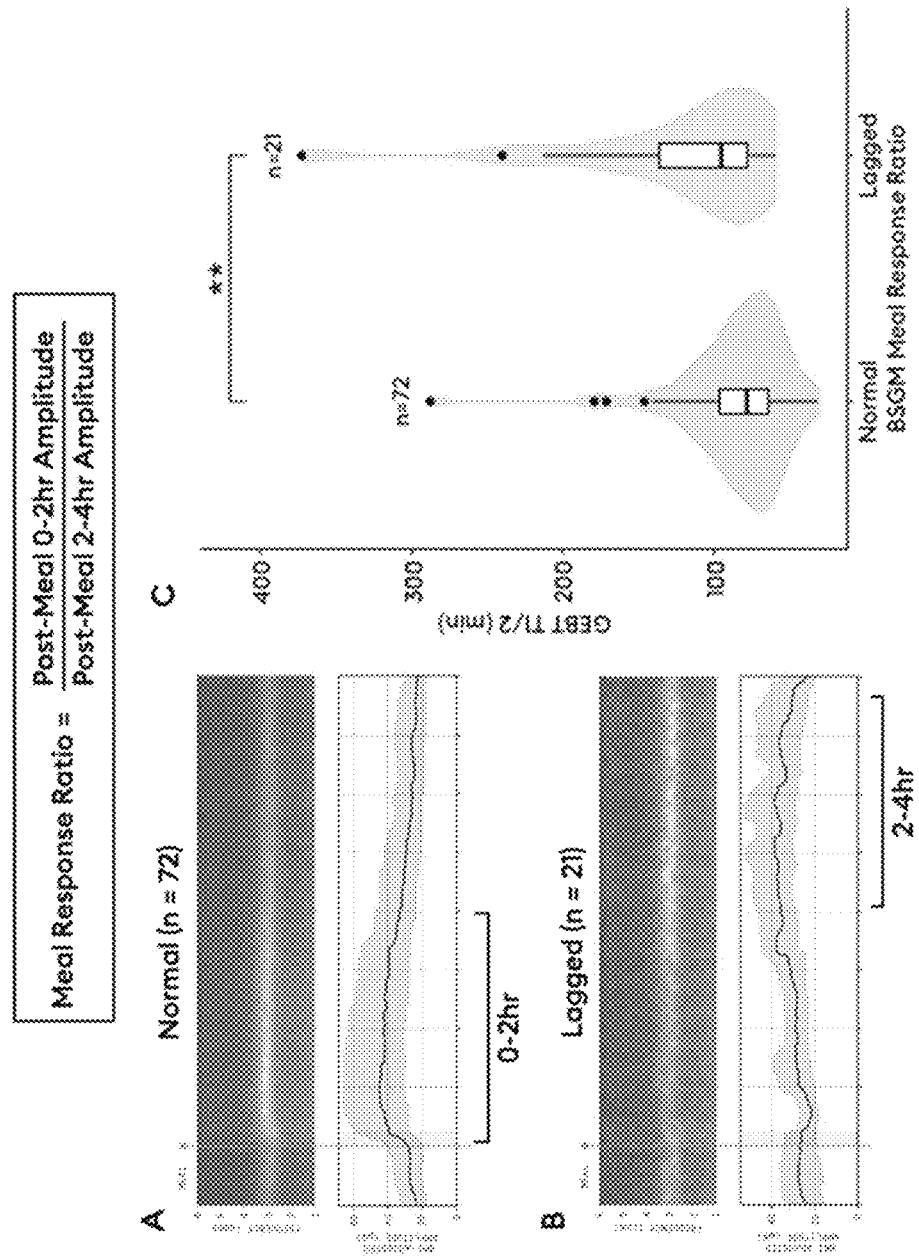
FIG. 30 illustrates an average spectrogram of patients with normal BSGM meal response, an average spectrogram of patients with lagged BSGM meal response, and associated box plots, in accordance with various embodiments of the present invention.

FIG. 30 illustrates an average spectrogram of patients with normal BSGM meal response, an average spectrogram of patients with lagged BSGM meal response, and associated box plots. Those with this lagged meal response phenotype on BSGM had a significantly longer $T_{1/2}$ on GEBT (median 98.5 [IQR 59-373] vs median 78.5 [IQR 31-288], p<0.001) and a higher rate of delayed emptying (52.8% [19/36] vs 23.4% [25/107], p=0.002).

Figure 31:
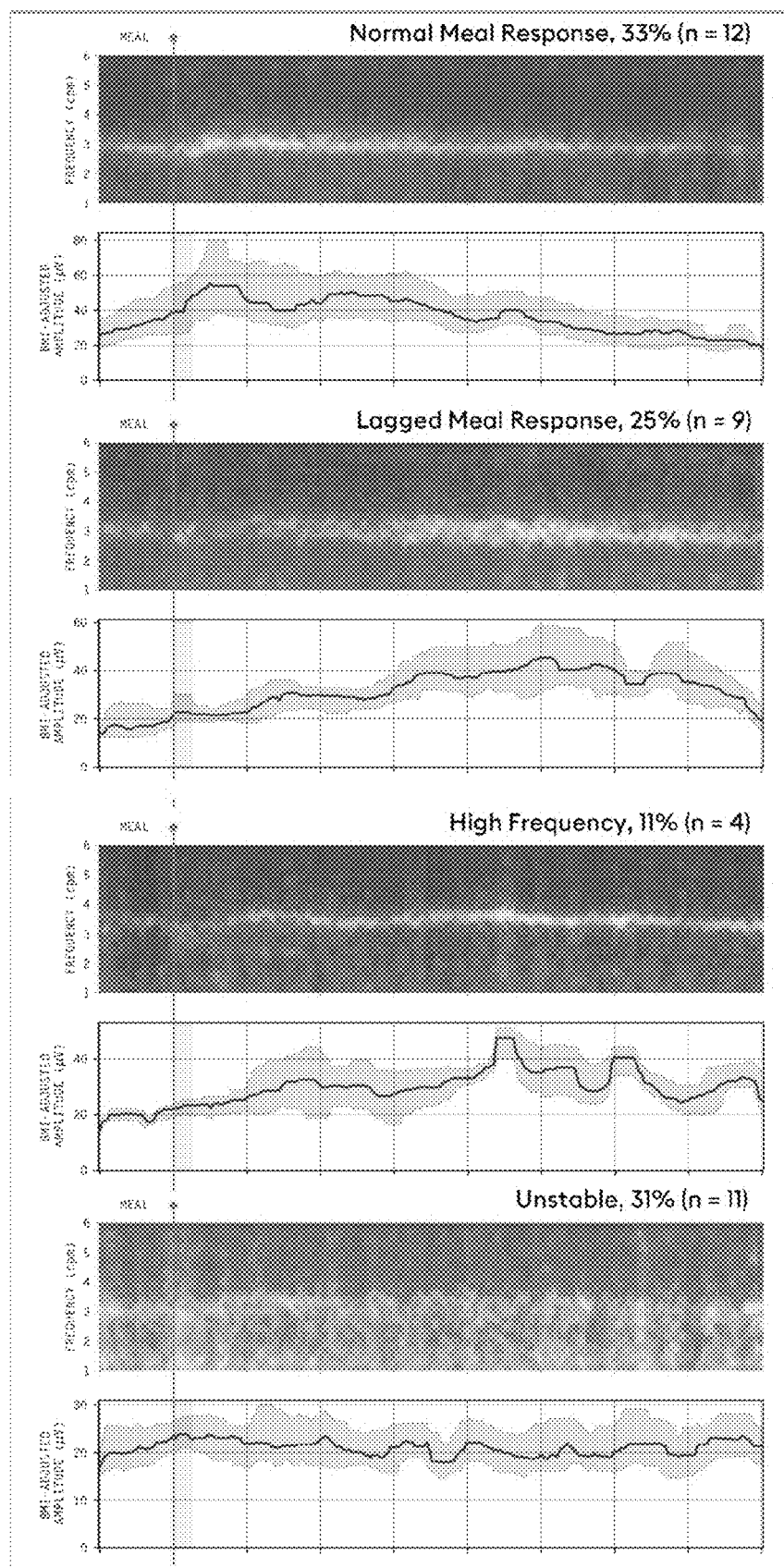
FIG. 31 illustrates phenotypes of delayed gastric emptying, in accordance with various embodiments of the present invention.

FIG. 31 illustrates phenotypes of delayed gastric emptying. Delayed gastric emptying may be characterized by phenotypes including normal meal response, lagged meal response, high frequency, unstable, etc. Among those with delayed gastric emptying on GEBT (n=36/143, 25%), the following BSGM phenotypes were identified: 12 (33.3%) had a normal spectral analysis, 9 (25.0%) had a lagged meal response phenotype (MRR≤1), 11 (30.6%) had a low amplitude or GA-RI, and 4 (11.1%) had a high PGF.

Figure 32:
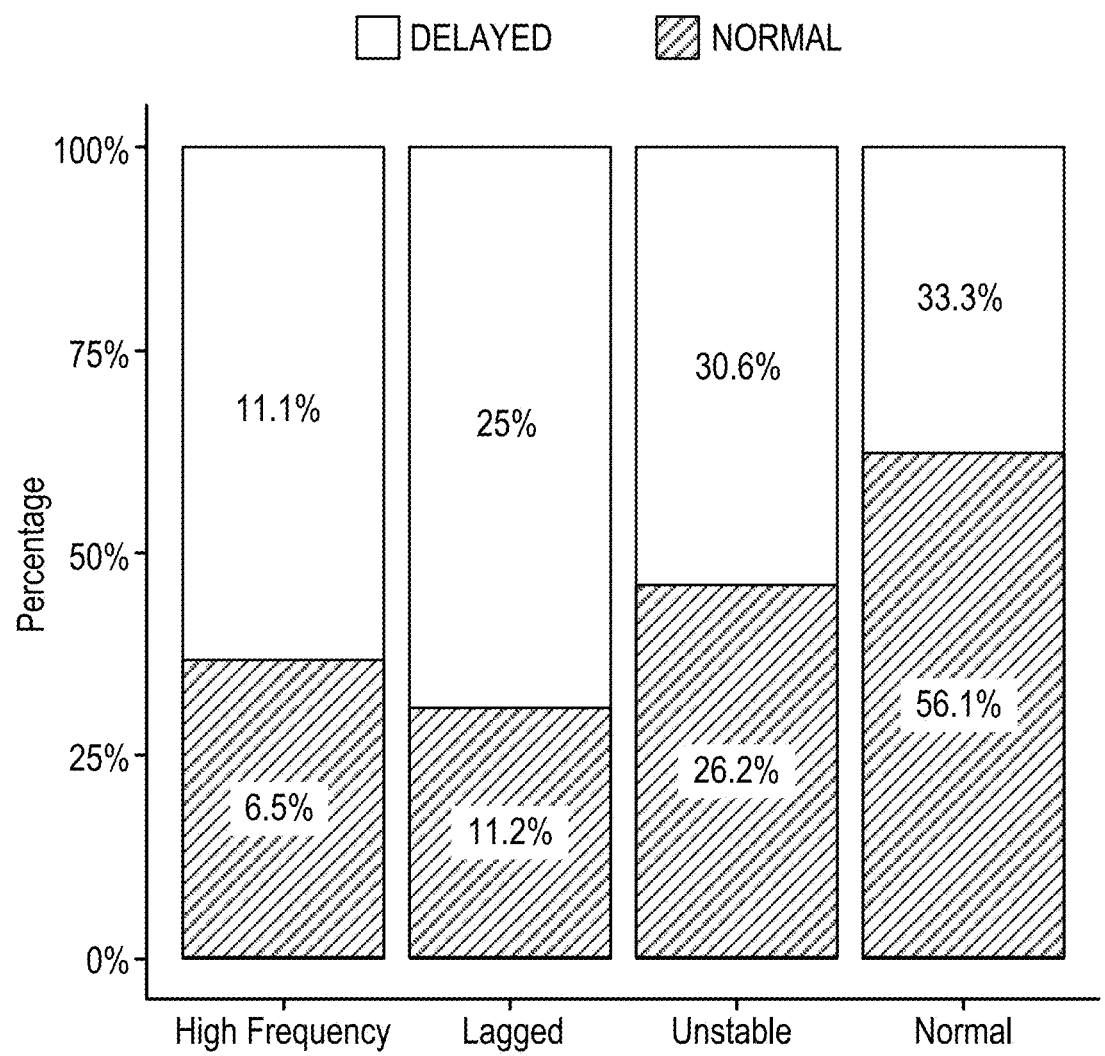
FIG. 32 illustrates proportions of each body surface gastric mapping phenotype with delayed and normal gastric emptying breath test results, in accordance with various embodiments of the present invention.

FIG. 32 illustrates proportions of each body surface gastric mapping phenotype with delayed and normal gastric emptying breath test results. In particular, FIG. 32 illustrates the proportion of each body surface gastric mapping phenotype with delayed and normal gastric emptying breath test results. The percentages reflect the proportion of each phenotype within their respective emptying classification. When emptying was normal, 28 (26.2%) had a low amplitude or GA-RI, 7 (6.5%) had a high PGF, 12 (11.2%) had a lagged meal response phenotype, and 60 (56.1%) had a normal BSGM. Notably the lagged meal response phenotype was more frequent in those with delayed emptying, (52.8% [19/36] vs 23.4% [25/107], p=0.002) and a normal BSGM was more common when in those with normal emptying (76% vs 47%, p=0.002).

Figure 33:
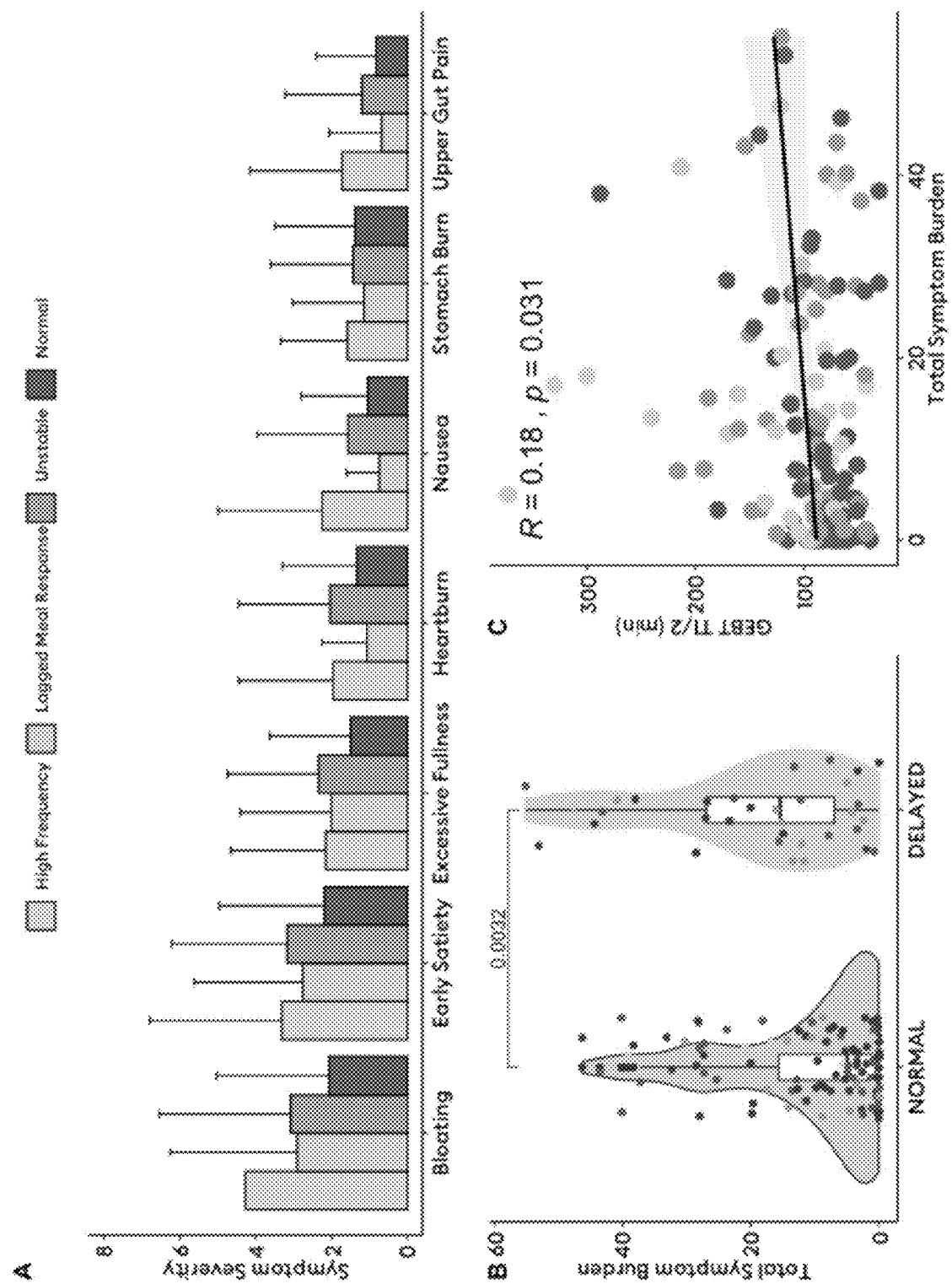
FIG. 33 illustrates symptom variation across BSGM phenotypes, in accordance with various embodiments of the present invention.

FIG. 33 illustrates symptom variation across BSGM phenotypes. Symptoms may vary across BSGM phenotypes. Section A) illustrates a mean and upper boundary of the standard deviation plotted across each symptom stratified by BSGM phenotype. There may be no statistically significant differences in symptom severity across body surface gastric mapping phenotypes (p>0.05). Section B) illustrates total symptom burden (0-70) between those with delayed and normal gastric emptying on GEBT. Participants with delayed gastric emptying tended to have worse symptoms with significant differences observed for nausea, upper gut pain, excessive fullness, and early satiety. Section C) illustrates a weak correlation between slower gastric emptying as measured by the $T_{1/2}$ on GEBT was shown with dots shaped by BSGM phenotype.

Correlations between delayed transit and 'Total Symptom Burden Score' were weak (r=0.18, p=0.03). Patients with delayed emptying and normal BSGM had higher early satiety scores (p=0.01) as shown in Table 1. There were no other differences in symptom severity between those with delayed and normal emptying across phenotypes (all comparisons p>0.05) as further shown in Table 1.

TABLE 1

Time-of-test symptom severity by delayed gastric emptying status based on gastric emptying breath testing after post-hoc correction.

| Symptom | Delayed GEBT | Normal GEBT | p |
|---|---|---|---|
| Nausea | 2.4 (2.6) | 1.0 (1.7) | 0.001 |
| Bloating | 2.8 (2.6) | 1.5 (2.1) | 0.004 |
| Upper Gut Pain | 2.4 (2.3) | 1.2 (1.9) | 0.004 |
| Heartburn | 1.2 (2.0) | 0.9 (1.7) | 0.325 |
| Stomach Burn | 1.6 (2.2) | 1.1 (1.9) | 0.202 |
| Excessive Fullness | 4.2 (3.2) | 2.1 (2.6) | <0.001 |
| Early Satiety | 4.3 (3.5) | 2.1 (3.0) | <0.001 |

Figure 34:
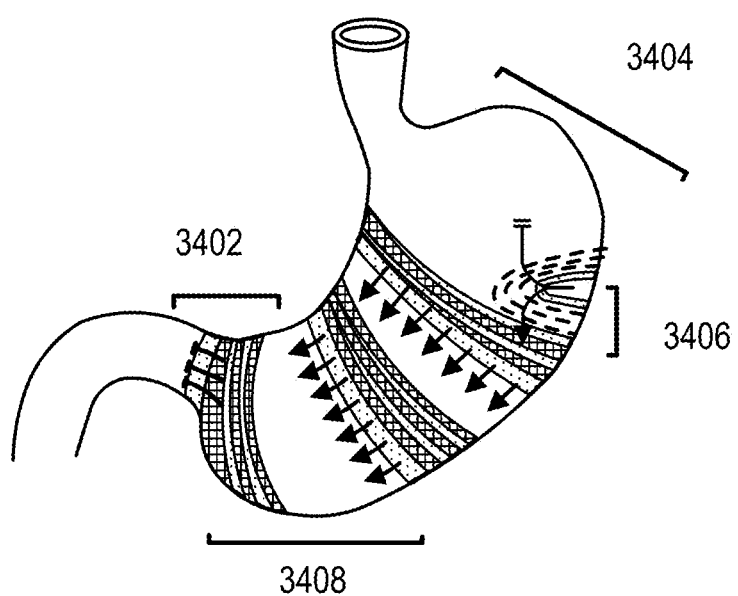
FIG. 34 illustrates mechanisms for gastroparesis mapped to each body surface gastric mapping phenotype, in accordance with various embodiments of the present invention.

FIG. 34 illustrates various putative mechanisms for gastroparesis mapped to each body surface gastric mapping phenotype. A normal meal response phenotype 3402 may be associated with normal spectral metrics and a MRR>1. A normal meal response phenotype 3402 may suggest sufficient stimulus to initiate antral contractile activity and a mechanism for delayed transit may include increased pyloric tone or antro-pyloric discoordination. A lagged meal response phenotype 3404 may be associated with a long lag to onset of gastric activity and a MRR≤1. A lagged meal response phenotype 3404 suggests inadequate stimulus to initiate antral contractile activity and a mechanism for delayed transit may include disordered accommodation or impaired gastroduodenal pressure gradients. A high frequency phenotype 3406 may be associated with an elevated entrained slow wave frequency (PGF≥3.35). Tachygastria and elevated slow wave frequencies may be associated with patients with long-term diabetes with end-organ damage and/or vagal nerve injury. A high frequency phenotype 3406 may suggest vagally mediated impairments in gastric function. An unstable phenotype 3408 may be associated with having irregular gastric electrical activity and a GA-RI<0.25. An unstable phenotype 3408 may be indicative of an impaired neuromuscular function as a cause for delayed transit such as antral hypomotility. Accordingly, various embodiments provide that the MRR may be used to differentiate proximal and distal gastric causes to delayed transit.

Various embodiments of the present invention may be used for monitoring and mapping gastric activity for a variety of applications. In one exemplary embodiment, any of the methods described above may be used for mapping gastric activity of a patient post-gastrointestinal surgery such as fundoplication. An electrode array patch disposed over an abdomen skin surface of the patient and the method may include measuring electrical signals associated with gastric activity after the gastrointestinal surgery of the patient from the electrode array patch over a predetermined time period. A gastrointestinal phenotype associated with post-gastrointestinal surgery may include at least one of a low rhythm stability phenotype or a high frequency phenotype, as described in detail above. In some embodiments, a high frequency phenotype is associated with vagal injury.

While exemplary embodiments have been illustrated and described, it will be appreciated that various changes can be made therein without departing from the spirit and scope of the disclosure.

The systems, apparatus, and methods described herein should not be construed as limiting in any way. Instead, the present disclosure is directed toward all novel and non-obvious features and aspects of the various disclosed embodiments, alone and in various combinations and sub-combinations with one another. The disclosed systems, methods, and apparatus are not limited to any specific aspect or feature or combinations thereof, nor do the disclosed systems, methods, and apparatus require that any one or more specific advantages be present, or problems be solved. Any theories of operation are to facilitate explanation, but the disclosed systems, methods, and apparatus are not limited to such theories of operation.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed systems, methods, and apparatus can be used in conjunction with other systems, methods, and apparatus. Additionally, the description sometimes uses terms like "produce" and "provide" to describe the disclosed methods. These terms are high-level abstractions of the actual operations that are performed. The actual operations that correspond to these terms will vary depending on the particular implementation and are readily discernible by one of ordinary skill in the art.

In some examples, values, procedures, or apparatuses are referred to as "lowest", "best", "minimum," or the like. It will be appreciated that such descriptions are intended to indicate that a selection among many used functional alternatives can be made, and such selections need not be better, smaller, or otherwise preferable to other selections.

What is claimed is:

1. A system for mapping gastric activity of a patient, the system comprising:
    an electrode array patch having a plurality of electrodes configured to measure electrical signals associated with gastric activity of the patient; and
    a processor configured to:
        receive the measured electrical signals from the electrode array patch over a continuous time period of at least 2 hours;
        concurrently receive patient symptom information over the entire continuous time period with the measured electrical signals;
        determine one or more normalized biometrics over at least a portion of the continuous time period from the measured electrical signals;
        correlating the one or more normalized biometrics and a symptom burden from the patient symptom information over the entire continuous time period;
        determine a measure of correlation over the continuous time period;
        determine a measure of temporal association in at least one time interval over the continuous time period between a gastric amplitude and at least one patient symptom information; and
        determine a gastrointestinal phenotype of the patient based at least in part on the measure of correlation and the measure of temporal association; and
        generate a report comprising at least the determination of the gastrointestinal phenotype.

2. The system of claim 1, further comprising a connector device coupled to the electrode array patch and wirelessly coupled to the processor.

3. The system of claim 2, wherein the connector device is configured for transmission of the measured electrical signals to the processor.

4. The system of claim 1, further comprising a patient mobile device for patient symptom information input, wherein the patient mobile device is in wireless communication with the processor for transmission of patient symptom information.

5. The system of claim 1, further comprising a display for displaying the generated report.

6. The system of claim 1, wherein the gastrointestinal phenotype comprises at least one of a normal Body Surface Gastric Mapping (BSGM) phenotype, a delayed onset phenotype, a low stability and/or low amplitude phenotype, or a high amplitude phenotype.

7. The system of claim 6, wherein the normal BSGM phenotype is associated with no measure of correlation and the measure of temporal association between −0.25 and +0.25 over a predetermined pre-prandial and post-prandial time period.

8. The system of claim 6, wherein the delayed onset phenotype is associated with the measure of temporal association less than −0.25 over a predetermined pre-prandial and post-prandial time period.

9. The system of claim 6, wherein the low stability and/or low amplitude phenotype is associated with the measure of temporal association between −0.25 and +0.25 over a predetermined pre-prandial and post-prandial time period.

10. The system of claim 6, wherein the low stability and/or low amplitude phenotype is associated with neuromuscular disorders.

11. The system of claim 10, wherein the neuromuscular disorder comprises at least one of gastric dysrhythmias, interstitial cell of Cajal disorders, antral hypomotility, smooth muscle disorders, or gastroparesis.

12. The system of claim 6, wherein the normal BSGM phenotype is associated with a gut-brain axis disorder.

13. The system of claim 12, wherein the gut-brain axis disorder comprises at least one of irritable bowel syndrome, reflux hypersensitivity, or functional dyspepsia.

14. The system of claim 6, wherein the delayed onset phenotype is associated with gastroparesis.

15. The system of claim 6, wherein the gastrointestinal phenotype comprises at least one of a sensorimotor phenotype, a neuromuscular phenotype, a post-gastric phenotype, an activity-alleviated phenotype, or a continuous phenotype.

16. The system of claim 1, wherein the one or more normalized biometrics comprises at least one of a principal gastric frequency (PGF), a body mass index (BMI)-adjusted amplitude, Gastric Alimetry Rhythm Index (GA-RI), fed-fasted amplitude ratio (ff-AR), and meal response ratio.

17. The system of claim 1, wherein the measured electrical signals and patient symptom information are received over a pre-prandial and post-prandial time period.

18. The system of claim of claim 1, wherein the patient symptom information comprises nausea, vomiting, bloating, upper gut pain, heartburn, stomach burn, or excessive fullness.

19. The system of claim of claim 18, wherein the symptom burden comprises a scaled rating or symptom curve.

20. The system of claim of claim 1, wherein determining a measure of temporal association comprises calculating a temporal correlation coefficient.

21. A system for mapping gastric activity of a patient, the system comprising:
    an electrode array patch having a plurality of electrodes configured to measure electrical signals associated with gastric activity of the patient; and
    a processor configured to:
        receive the measured electrical signals from the electrode array patch over a continuous time period of at least 2 hours;
        concurrently receive patient symptom information over the entire continuous time period with the measured electrical signals;
        determine one or more normalized biometrics over at least a portion of the continuous time period from the measured electrical signals;
        correlating the one or more normalized biometrics and a symptom burden from the patient symptom information;
        determine a measure of correlation over the continuous time period;

determine a measure of temporal association in at least one time interval over the continuous time period between one or more normalized biometrics and at least two symptoms from the patient symptom information; and determine a gastrointestinal phenotype of the patient based at least in part on the measure of correlation and the measure of temporal association, wherein the phenotype comprises at least one of a sensorimotor phenotype, a neuromuscular phenotype, a post-gastric phenotype, an activity-alleviated phenotype, or a continuous phenotype; and generate a report comprising at least the determination of the gastrointestinal phenotype.

22. The system of claim of claim 21, wherein the patient symptom information comprises nausea, vomiting, bloating, upper gut pain, heartburn, stomach burn, or excessive fullness.

23. The system of claim of claim 22, wherein the symptom burden comprises a scaled rating or symptom curve.

24. The system of claim of claim 21, wherein the one or more normalized biometrics comprises at least one of a principal gastric frequency (PGF), a body mass index (BMI)-adjusted amplitude, Gastric Alimetry Rhythm Index (GA-RI), fed-fasted amplitude ratio (ff-AR), and meal response ratio.

25. The system of claim of claim 21, wherein determining a measure of temporal association comprises calculating a temporal correlation coefficient.

\* \* \* \* \*